US012667714B2

(12) United States Patent
　　Stotz et al.

(10) Patent No.:　US 12,667,714 B2
(45) Date of Patent:　Jun. 30, 2026

(54) LINE DEVICE FOR CONDUCTING A BLOOD FLOW FOR A HEART SUPPORT SYSTEM, AND PRODUCTION AND ASSEMBLY METHOD

(71) Applicant: KARDION GMBH, Stuttgart (DE)

(72) Inventors: Ingo Stotz, Ditzingen (DE); Hardy Baumbach, Stuttgart (DE); Inga Schellenberg, Stuttgart (DE); David Minzenmay, Stuttgart (DE)

(73) Assignee: KARDION GMBH, Stuttgart (DE)

( * ) Notice: Subject to any disclaimer, the term of this patent is extended or adjusted under 35 U.S.C. 154(b) by 761 days.

(21) Appl. No.: 17/057,355

(22) PCT Filed: May 30, 2019

(86) PCT No.: PCT/EP2019/064136
　　§ 371 (c)(1),
　　(2) Date: May 18, 2021

(87) PCT Pub. No.: WO2019/229210
　　PCT Pub. Date: Dec. 5, 2019

(65) Prior Publication Data
　　US 2021/0268264 A1　　Sep. 2, 2021

(30) Foreign Application Priority Data

May 30, 2018　(DE) ..................... 10 2018 208 536.6

(51) Int. Cl.
　　*A61M 60/859*　　(2021.01)
　　*A61M 60/139*　　(2021.01)
　　　　(Continued)
(52) U.S. Cl.
　　CPC ........ *A61M 60/859* (2021.01); *A61M 60/139* (2021.01); *A61M 60/148* (2021.01); *A61M 60/178* (2021.01); *A61M 60/216* (2021.01)

(58) Field of Classification Search
　　CPC .............. A61M 60/859; A61M 60/139; A61M 60/148; A61M 60/178; A61M 60/216;
　　　　(Continued)

(56) References Cited

U.S. PATENT DOCUMENTS 2,254,698　A　　9/1941　Hansen, Jr.
2,310,923　A　　2/1943　Bean
　　　　(Continued)

FOREIGN PATENT DOCUMENTS

AU　　　7993698　　　2/1999
AU　　2002308409　　12/2005
　　　　(Continued)

OTHER PUBLICATIONS

Hertz Ph.D. et al, "Ultrasonic Engineering in Heart Diagnosis", The American Journal of Cardiology, Jan. 1967, vol. 19, No. 1, pp. 6-17.
　　　　(Continued)

*Primary Examiner* — Jennifer Pitrak McDonald
*Assistant Examiner* — Christopher J Mutchler
(74) *Attorney, Agent, or Firm* — Knobbe, Martens, Olson & Bear, LLP

(57) ABSTRACT

The invention relates to a line device (105) for conducting a blood flow for a heart support system. The line device (105) has a main part (205), and the main part (205) has a first attachment section (210) at a first end for attaching the line device (105) to a head unit of the heart support system and a second attachment section (215) at a second end for attaching the line device (105) to an outlet unit of the heart support system (100). The attachment sections (210, 215) are shaped so as to be connectable in a form-fitting and/or force-fitting manner. The main part (205) has a structured section (220) with at least one stiffening recess (225) between the attachment sections (210, 215), the at least one
　　　　(Continued)

stiffening recess (225) being shaped so as to change the stiffness of the main part (205).

30 Claims, 11 Drawing Sheets

(51) Int. Cl.
    *A61M 60/148*      (2021.01)
    *A61M 60/178*      (2021.01)
    *A61M 60/216*      (2021.01)

(58) Field of Classification Search
    CPC .............. A61M 60/221; A61M 60/857; A61M
                 60/865; A61M 60/13; A61M 60/01
    See application file for complete search history.

(56) References Cited

U.S. PATENT DOCUMENTS

| | | | |
|---|---|---|---|
| 3,085,407 | A | 4/1963 | Tomlinson |
| 3,088,323 | A | 5/1963 | Welkowitz et al. |
| 3,505,987 | A | 4/1970 | Heilman |
| 3,568,659 | A | 3/1971 | Karnegis |
| 3,614,181 | A | 10/1971 | Meeks |
| 3,747,998 | A | 7/1973 | Klein et al. |
| 3,807,813 | A | 4/1974 | Milligan |
| 3,995,617 | A | 12/1976 | Watkins et al. |
| 4,023,562 | A | 5/1977 | Hynecek et al. |
| 4,115,040 | A | 9/1978 | Knorr |
| 4,245,622 | A | 1/1981 | Hutchins, IV |
| 4,471,252 | A | 9/1984 | West |
| 4,522,194 | A | 6/1985 | Normann |
| 4,559,952 | A | 12/1985 | Angelsen et al. |
| 4,625,712 | A | 12/1986 | Wampler |
| 4,643,641 | A | 2/1987 | Clausen et al. |
| 4,680,730 | A | 7/1987 | Omoda |
| 4,753,221 | A | 6/1988 | Kensey et al. |
| 4,779,614 | A | 10/1988 | Moise |
| 4,781,525 | A | 11/1988 | Hubbard et al. |
| 4,785,795 | A | 11/1988 | Singh et al. |
| 4,817,586 | A | 4/1989 | Wampler |
| 4,846,152 | A | 7/1989 | Wampler et al. |
| 4,888,011 | A | 12/1989 | Kung et al. |
| 4,889,131 | A | 12/1989 | Salem et al. |
| 4,895,557 | A | 1/1990 | Moise et al. |
| 4,896,754 | A | 1/1990 | Carlson et al. |
| 4,902,272 | A | 2/1990 | Milder et al. |
| 4,908,012 | A | 3/1990 | Moise et al. |
| 4,927,407 | A | 5/1990 | Dorman |
| 4,943,275 | A | 7/1990 | Stricker |
| 4,944,722 | A | 7/1990 | Carriker et al. |
| 4,968,300 | A | 11/1990 | Moutafis et al. |
| 4,971,768 | A | 11/1990 | Ealba |
| 4,985,014 | A | 1/1991 | Orejola |
| 5,044,897 | A | 9/1991 | Dorman |
| 5,045,051 | A | 9/1991 | Milder et al. |
| 5,061,256 | A | 10/1991 | Wampler |
| 5,089,016 | A | 2/1992 | Millner et al. |
| 5,090,957 | A | 2/1992 | Moutafis et al. |
| 5,112,292 | A | 5/1992 | Hwang et al. |
| 5,112,349 | A | 5/1992 | Summers et al. |
| 5,116,305 | A | 5/1992 | Milder et al. |
| 5,195,877 | A | 3/1993 | Kletschka |
| 5,269,811 | A | 12/1993 | Hayes |
| 5,289,821 | A | 3/1994 | Swartz |
| 5,290,227 | A | 3/1994 | Pasque |
| 5,297,940 | A | 3/1994 | Buse |
| 5,313,765 | A | 5/1994 | Martin |
| 5,344,443 | A | 9/1994 | Palma et al. |
| 5,354,271 | A | 10/1994 | Voda |
| 5,376,114 | A | 12/1994 | Jarvik |
| 5,399,145 | A | 3/1995 | Ito et al. |
| 5,405,383 | A | 4/1995 | Barr |
| 5,443,503 | A | 8/1995 | Yamane |
| 5,456,715 | A | 10/1995 | Liotta |
| 5,527,159 | A | 6/1996 | Bozeman, Jr. et al. |
| 5,581,038 | A | 12/1996 | Lampropoulos |
| 5,599,173 | A | 2/1997 | Chen et al. |
| 5,606,972 | A | 3/1997 | Routh |
| 5,613,935 | A | 3/1997 | Jarvik |
| 5,662,115 | A | 9/1997 | Torp |
| 5,676,651 | A | 10/1997 | Larson, Jr. et al. |
| 5,695,471 | A | 12/1997 | Wampler |
| 5,702,430 | A | 12/1997 | Larson, Jr. et al. |
| 5,720,771 | A | 2/1998 | Snell |
| 5,746,709 | A | 5/1998 | Rom et al. |
| 5,749,855 | A | 5/1998 | Reitan |
| 5,752,976 | A | 5/1998 | Duffin et al. |
| 5,766,207 | A | 6/1998 | Potter et al. |
| 5,827,203 | A | 10/1998 | Nita |
| 5,831,365 | A | 11/1998 | Keim et al. |
| 5,865,759 | A | 2/1999 | Koblanski |
| 5,888,241 | A | 3/1999 | Jarvik |
| 5,888,242 | A | 3/1999 | Antaki et al. |
| 5,904,646 | A | 5/1999 | Jarvik |
| 5,904,708 | A | 5/1999 | Goedeke |
| 5,911,685 | A | 6/1999 | Siess et al. |
| 5,921,913 | A | 7/1999 | Siess |
| 5,964,694 | A | 10/1999 | Siess et al. |
| 5,980,465 | A | 11/1999 | Elgas |
| 6,001,056 | A | 12/1999 | Jassawalla et al. |
| 6,007,478 | A | 12/1999 | Siess et al. |
| 6,018,208 | A | 1/2000 | Maher et al. |
| 6,024,704 | A | 2/2000 | Meador et al. |
| 6,050,975 | A | 4/2000 | Poirier |
| 6,053,873 | A | 4/2000 | Govari et al. |
| 6,071,093 | A | 6/2000 | Hart |
| 6,116,862 | A | 9/2000 | Rau et al. |
| 6,123,659 | A | 9/2000 | le Blanc et al. |
| 6,135,710 | A | 10/2000 | Araki et al. |
| 6,149,405 | A | 11/2000 | Abe et al. |
| 6,155,969 | A | 12/2000 | Schima et al. |
| 6,158,984 | A | 12/2000 | Cao et al. |
| 6,161,838 | A | 12/2000 | Balsells |
| 6,167,765 | B1 | 1/2001 | Weitzel |
| 6,176,822 | B1 | 1/2001 | Nix et al. |
| 6,176,848 | B1 | 1/2001 | Rau et al. |
| 6,183,412 | B1 | 2/2001 | Benkowsi et al. |
| 6,185,460 | B1 | 2/2001 | Thompson |
| 6,186,665 | B1 | 2/2001 | Maher et al. |
| 6,190,324 | B1 | 2/2001 | Kieval et al. |
| 6,210,318 | B1 | 4/2001 | Lederman |
| 6,217,541 | B1 | 4/2001 | Yu |
| 6,220,832 | B1 | 4/2001 | Schob |
| 6,227,820 | B1 | 5/2001 | Jarvik |
| 6,231,498 | B1 | 5/2001 | Pfeiffer et al. |
| 6,245,007 | B1 | 6/2001 | Bedingham et al. |
| 6,254,359 | B1 | 7/2001 | Aber |
| 6,264,205 | B1 | 7/2001 | Balsells |
| 6,264,601 | B1 | 7/2001 | Jassawalla et al. |
| 6,264,645 | B1 | 7/2001 | Jonkman |
| 6,293,752 | B1 | 9/2001 | Clague et al. |
| 6,314,322 | B1 | 11/2001 | Rosenberg |
| 6,351,048 | B1 | 2/2002 | Schob et al. |
| 6,361,292 | B1 | 3/2002 | Chang et al. |
| 6,398,734 | B1 | 6/2002 | Cimochowski et al. |
| 6,432,136 | B1 | 8/2002 | Weiss et al. |
| 6,438,409 | B1 | 8/2002 | Malik et al. |
| 6,445,956 | B1 | 9/2002 | Laird et al. |
| 6,447,266 | B2 | 9/2002 | Antaki et al. |
| 6,512,949 | B1 | 1/2003 | Combs et al. |
| 6,527,698 | B1 | 3/2003 | Kung et al. |
| 6,530,876 | B1 | 3/2003 | Spence |
| 6,533,716 | B1 | 3/2003 | Schmitz-Rode et al. |
| 6,540,658 | B1 | 4/2003 | Fasciano et al. |
| 6,540,659 | B1 | 4/2003 | Milbocker |
| 6,544,216 | B1 | 4/2003 | Sammler et al. |
| 6,561,975 | B1 | 5/2003 | Pool et al. |
| 6,579,257 | B1 | 6/2003 | Elgas et al. |
| 6,592,620 | B1 | 7/2003 | Lancisi et al. |
| 6,595,743 | B1 | 7/2003 | Kazatchkov et al. |
| 6,602,182 | B1 | 8/2003 | Milbocker |
| 6,605,032 | B2 | 8/2003 | Benkowsi et al. |
| 6,607,368 | B1 | 8/2003 | Ross et al. |

(56)                References Cited

U.S. PATENT DOCUMENTS

| | | | |
|---|---|---|---|
| 6,623,475 | B1 | 9/2003 | Siess |
| 6,652,447 | B2 | 11/2003 | Benkowsi et al. |
| 6,719,791 | B1 | 4/2004 | Nüsser et al. |
| 6,731,976 | B2 | 5/2004 | Penn et al. |
| 6,794,789 | B2 | 9/2004 | Siess et al. |
| 6,841,910 | B2 | 1/2005 | Gery |
| 6,879,126 | B2 | 4/2005 | Paden et al. |
| 6,912,423 | B2 | 6/2005 | Ley et al. |
| 6,942,611 | B2 | 9/2005 | Siess |
| 6,949,066 | B2 | 9/2005 | Bearnson et al. |
| 6,969,345 | B2 | 11/2005 | Jassawalla et al. |
| 6,984,201 | B2 | 1/2006 | Khaghani et al. |
| 7,010,954 | B2 | 3/2006 | Siess |
| 7,011,620 | B1 | 3/2006 | Siess |
| 7,014,620 | B2 | 3/2006 | Kim |
| 7,022,100 | B1 * | 4/2006 | Aboul-Hosn ....... A61M 60/865 |
| | | | 604/6.11 |
| 7,024,244 | B2 | 4/2006 | Muhlenberg et al. |
| 7,027,875 | B2 | 4/2006 | Siess et al. |
| 7,070,398 | B2 | 7/2006 | Olsen et al. |
| 7,070,555 | B2 | 7/2006 | Siess |
| 7,083,588 | B1 | 8/2006 | Shmulewitz et al. |
| 7,138,776 | B1 | 11/2006 | Gauthier et al. |
| 7,144,364 | B2 | 12/2006 | Barbut et al. |
| 7,160,243 | B2 | 1/2007 | Medvedev |
| 7,175,588 | B2 | 2/2007 | Morello |
| 7,177,681 | B2 | 2/2007 | Xhu |
| 7,238,151 | B2 | 7/2007 | Frazier |
| 7,241,257 | B1 | 7/2007 | Ainsworth et al. |
| 7,264,606 | B2 | 9/2007 | Jarvik et al. |
| 7,393,181 | B2 | 7/2008 | McBride et al. |
| 7,396,327 | B2 | 7/2008 | Morello |
| 7,462,019 | B1 | 12/2008 | Allarie et al. |
| 7,479,102 | B2 | 1/2009 | Jarvik |
| 7,502,648 | B2 | 3/2009 | Okubo et al. |
| 7,513,864 | B2 | 4/2009 | Kantrowitz et al. |
| 7,520,850 | B2 | 4/2009 | Brockway |
| 7,526,338 | B1 | 4/2009 | Gill |
| 7,527,599 | B2 | 5/2009 | Hickey |
| 7,591,777 | B2 | 9/2009 | LaRose |
| 7,736,296 | B2 | 6/2010 | Siess et al. |
| 7,744,560 | B2 | 6/2010 | Struble |
| 7,762,941 | B2 | 7/2010 | Jarvik |
| 7,794,384 | B2 | 9/2010 | Sugiura et al. |
| 7,798,952 | B2 | 9/2010 | Tansley et al. |
| 7,819,916 | B2 | 10/2010 | Yaegashi |
| 7,841,976 | B2 | 11/2010 | McBride et al. |
| 7,850,593 | B2 | 12/2010 | Vincent et al. |
| 7,850,594 | B2 | 12/2010 | Sutton et al. |
| 7,856,335 | B2 | 12/2010 | Morello et al. |
| 7,862,501 | B2 | 1/2011 | Woodward et al. |
| 7,878,967 | B1 | 2/2011 | Khanal |
| 7,914,436 | B1 | 3/2011 | Kung |
| 7,934,909 | B2 | 5/2011 | Nuesser et al. |
| 7,951,062 | B2 | 5/2011 | Morello |
| 7,951,129 | B2 | 5/2011 | Chinchoy |
| 7,959,551 | B2 | 6/2011 | Jarvik |
| 7,963,905 | B2 | 6/2011 | Salmonsen et al. |
| 7,988,728 | B2 | 8/2011 | Ayre |
| 7,998,190 | B2 | 8/2011 | Gharib et al. |
| 8,012,079 | B2 | 9/2011 | Delgado, III |
| 8,075,472 | B2 | 12/2011 | Zilbershlag et al. |
| 8,088,059 | B2 | 1/2012 | Jarvik |
| 8,114,008 | B2 | 2/2012 | Hidaka et al. |
| 8,123,669 | B2 | 2/2012 | Siess et al. |
| RE43,299 | E | 4/2012 | Siess |
| 8,152,845 | B2 | 4/2012 | Bourque |
| 8,177,703 | B2 | 5/2012 | Smith et al. |
| 8,190,390 | B2 | 5/2012 | Morello et al. |
| 8,211,028 | B2 | 7/2012 | Karamanoglu et al. |
| 8,216,122 | B2 | 7/2012 | Kung |
| 8,303,482 | B2 | 11/2012 | Schima et al. |
| 8,323,173 | B2 | 12/2012 | Benkowsi et al. |
| 8,371,997 | B2 | 2/2013 | Shifflette |
| 8,376,926 | B2 | 2/2013 | Benkowsi et al. |
| 8,382,695 | B1 | 2/2013 | Patel |
| 8,388,565 | B2 | 3/2013 | Shifflette |
| 8,419,609 | B2 | 4/2013 | Shambaugh, Jr. et al. |
| 8,435,182 | B1 | 5/2013 | Tamura |
| 8,449,443 | B2 | 5/2013 | Rodefeld et al. |
| 8,449,444 | B2 | 5/2013 | Poirier |
| 8,480,555 | B2 | 7/2013 | Kung |
| 8,485,961 | B2 | 7/2013 | Campbell et al. |
| 8,512,012 | B2 | 8/2013 | Akdis et al. |
| 8,535,211 | B2 | 9/2013 | Campbell et al. |
| 8,545,380 | B2 | 10/2013 | Farnan et al. |
| 8,562,508 | B2 | 10/2013 | Dague et al. |
| 8,585,572 | B2 | 11/2013 | Mehmanesh |
| 8,591,393 | B2 * | 11/2013 | Walters ............... A61M 60/554 |
| | | | 600/16 |
| 8,591,538 | B2 | 11/2013 | Gellman |
| 8,591,539 | B2 | 11/2013 | Gellman |
| 8,594,790 | B2 | 11/2013 | Kjellstrom et al. |
| 8,597,170 | B2 | 12/2013 | Walters et al. |
| 8,617,239 | B2 | 12/2013 | Reitan |
| 8,622,949 | B2 | 1/2014 | Zafirelis et al. |
| 8,641,594 | B2 | 2/2014 | LaRose et al. |
| 8,657,733 | B2 | 2/2014 | Ayre et al. |
| 8,657,875 | B2 | 2/2014 | Kung et al. |
| 8,684,362 | B2 | 4/2014 | Balsells et al. |
| 8,684,904 | B2 | 4/2014 | Campbell et al. |
| 8,690,749 | B1 | 4/2014 | Nunez |
| 8,715,151 | B2 | 5/2014 | Poirier |
| 8,721,517 | B2 | 5/2014 | Zeng et al. |
| 8,727,959 | B2 | 5/2014 | Reitan et al. |
| 8,731,664 | B2 | 5/2014 | Foster et al. |
| 8,734,331 | B2 | 5/2014 | Evans et al. |
| 8,747,293 | B2 | 6/2014 | Arndt et al. |
| 8,814,933 | B2 | 8/2014 | Siess |
| 8,849,398 | B2 | 9/2014 | Evans |
| 8,864,642 | B2 | 10/2014 | Scheckel |
| 8,864,643 | B2 | 10/2014 | Reichenbach et al. |
| 8,864,644 | B2 | 10/2014 | Yomtov |
| 8,876,685 | B2 | 11/2014 | Crosby et al. |
| 8,882,477 | B2 | 11/2014 | Fritz, IV et al. |
| 8,888,728 | B2 | 11/2014 | Aboul-Hosn et al. |
| 8,894,387 | B2 | 11/2014 | White |
| 8,897,873 | B2 | 11/2014 | Schima et al. |
| 8,900,060 | B2 | 12/2014 | Liebing |
| 8,900,115 | B2 | 12/2014 | Bolling et al. |
| 8,903,492 | B2 | 12/2014 | Soykan et al. |
| 8,932,246 | B2 | 1/2015 | Ferrari |
| 8,992,406 | B2 | 3/2015 | Corbett |
| 8,992,407 | B2 | 3/2015 | Smith et al. |
| 9,028,216 | B2 | 5/2015 | Schumacher et al. |
| 9,028,392 | B2 | 5/2015 | Shifflette |
| 9,033,863 | B2 | 5/2015 | Jarvik |
| 9,091,271 | B2 | 7/2015 | Bourque |
| 9,138,518 | B2 | 9/2015 | Campbell et al. |
| 9,144,638 | B2 | 9/2015 | Zimmermann et al. |
| 9,162,017 | B2 | 10/2015 | Evans et al. |
| 9,192,705 | B2 | 11/2015 | Yanai et al. |
| 9,199,020 | B2 | 12/2015 | Siess |
| 9,265,870 | B2 | 2/2016 | Reichenbach et al. |
| 9,297,735 | B2 | 3/2016 | Graichen et al. |
| 9,308,305 | B2 | 4/2016 | Chen et al. |
| 9,314,556 | B2 | 4/2016 | Tuseth |
| 9,327,067 | B2 | 5/2016 | Zeng et al. |
| 9,327,068 | B2 | 5/2016 | Aboul-Hosn et al. |
| 9,345,824 | B2 | 5/2016 | Mohl et al. |
| 9,370,613 | B2 | 6/2016 | Hsu et al. |
| 9,371,826 | B2 | 6/2016 | Yanai et al. |
| 9,381,286 | B2 | 7/2016 | Spence et al. |
| 9,421,311 | B2 | 8/2016 | Tanner et al. |
| 9,427,508 | B2 | 8/2016 | Reyes et al. |
| 9,427,509 | B2 | 8/2016 | Vodermayer |
| 9,433,713 | B2 | 9/2016 | Corbett et al. |
| 9,440,013 | B2 | 9/2016 | Dowling et al. |
| 9,474,840 | B2 * | 10/2016 | Siess ................... A61M 60/857 |
| 9,486,566 | B2 | 11/2016 | Siess |
| 9,492,601 | B2 | 11/2016 | Casas et al. |
| 9,511,179 | B2 | 12/2016 | Casas et al. |
| 9,533,084 | B2 | 1/2017 | Siess et al. |
| 9,539,378 | B2 | 1/2017 | Tuseth |

(56) References Cited

U.S. PATENT DOCUMENTS

| | | | |
|---|---|---|---|
| 9,550,017 B2 | 1/2017 | Spanier et al. |
| 9,555,173 B2 | 1/2017 | Spanier |
| 9,555,175 B2 | 1/2017 | Bulent et al. |
| 9,556,873 B2 | 1/2017 | Yanai et al. |
| 9,561,313 B2 | 2/2017 | Taskin |
| 9,561,314 B2 | 2/2017 | Aboul-Hosn et al. |
| 9,566,374 B2 | 2/2017 | Spence et al. |
| 9,579,433 B2 | 2/2017 | LaRose et al. |
| 9,585,991 B2 | 3/2017 | Spence |
| 9,592,397 B2 | 3/2017 | Hansen et al. |
| 9,616,157 B2 | 4/2017 | Akdis |
| 9,623,162 B2 | 4/2017 | Graham et al. |
| 9,623,163 B1 | 4/2017 | Fischi |
| 9,636,442 B2 | 5/2017 | Karmon et al. |
| 9,656,010 B2 | 5/2017 | Burke |
| 9,669,142 B2 | 6/2017 | Spanier et al. |
| 9,669,144 B2 | 6/2017 | Spanier et al. |
| 9,675,738 B2 | 6/2017 | Tanner et al. |
| 9,675,739 B2 | 6/2017 | Tanner et al. |
| 9,675,740 B2 | 6/2017 | Zeng et al. |
| 9,682,180 B2 | 6/2017 | Hoarau et al. |
| 9,694,123 B2 | 7/2017 | Bourque et al. |
| 9,713,701 B2 | 7/2017 | Sarkar et al. |
| 9,717,833 B2 | 8/2017 | McBride et al. |
| 9,731,058 B2 | 8/2017 | Siebenhaar et al. |
| 9,744,282 B2 | 8/2017 | Rosenberg et al. |
| 9,759,222 B2 | 9/2017 | Zimmermann et al. |
| 9,770,543 B2 | 9/2017 | Tanner et al. |
| 9,789,236 B2 | 10/2017 | Bonde |
| 9,789,238 B2 | 10/2017 | Aboul-Hosn et al. |
| 9,801,990 B2 | 10/2017 | Lynch |
| 9,814,813 B2 | 11/2017 | Corbett |
| 9,821,100 B2 | 11/2017 | Corbett et al. |
| 9,833,550 B2 | 12/2017 | Siess |
| 9,848,899 B2 | 12/2017 | Sliwa et al. |
| 9,849,223 B2 | 12/2017 | LaRose |
| 9,849,224 B2 | 12/2017 | Angwin et al. |
| 9,872,948 B2 | 1/2018 | Siess |
| 9,878,087 B2 | 1/2018 | Richardson et al. |
| 9,907,890 B2 | 3/2018 | Muller |
| 9,919,087 B2 | 3/2018 | Pfeffer et al. |
| 9,943,236 B2 | 4/2018 | Bennett et al. |
| 9,950,101 B2 | 4/2018 | Smith et al. |
| 9,950,102 B2 | 4/2018 | Spence et al. |
| 9,968,719 B2 | 5/2018 | Colella |
| 9,974,894 B2 | 5/2018 | Morello |
| 9,999,714 B2 | 6/2018 | Spanier et al. |
| 10,010,662 B2 | 7/2018 | Wiesener et al. |
| 10,022,480 B2 | 7/2018 | Greatrex et al. |
| 10,029,037 B2 | 7/2018 | Muller et al. |
| 10,052,420 B2 | 8/2018 | Medvedev et al. |
| 10,123,875 B2 | 11/2018 | Wildhirt et al. |
| 10,124,102 B2 | 11/2018 | Bulent et al. |
| 10,130,742 B2 | 11/2018 | Tuseth |
| 10,149,932 B2 | 12/2018 | McBride et al. |
| 10,179,197 B2 | 1/2019 | Kaiser et al. |
| 10,201,645 B2 | 2/2019 | Muller |
| 10,207,038 B2 | 2/2019 | Neumann |
| 10,220,129 B2 | 3/2019 | Ayre et al. |
| 10,232,099 B2 | 3/2019 | Peters et al. |
| 10,238,782 B2 | 3/2019 | Barry |
| 10,238,783 B2 | 3/2019 | Aboul-Hosn et al. |
| 10,251,986 B2 | 4/2019 | Larose et al. |
| 10,279,093 B2 | 5/2019 | Reichenbach et al. |
| 10,293,090 B2 | 5/2019 | Bonde et al. |
| 10,300,185 B2 | 5/2019 | Aboul-Hosn et al. |
| 10,300,249 B2 | 5/2019 | Tao et al. |
| 10,322,217 B2 | 6/2019 | Spence |
| 10,342,906 B2 | 7/2019 | D'Ambrosio et al. |
| 10,350,342 B2 | 7/2019 | Thomas et al. |
| 10,357,598 B2 | 7/2019 | Aboul-Hosn et al. |
| 10,361,617 B2 | 7/2019 | Mueller et al. |
| 10,371,150 B2 | 8/2019 | Wu et al. |
| 10,376,162 B2 | 8/2019 | Edelman et al. |
| 10,413,651 B2 | 9/2019 | Yomtov et al. |
| 10,420,869 B2 | 9/2019 | Cornen |
| 10,426,879 B2 | 10/2019 | Farnan |
| 10,434,232 B2 | 10/2019 | Wu et al. |
| 10,449,275 B2 | 10/2019 | Corbett |
| 10,449,279 B2 | 10/2019 | Muller |
| 10,478,538 B2 | 11/2019 | Scheckel et al. |
| 10,478,539 B2 | 11/2019 | Pfeffer et al. |
| 10,478,542 B2 | 11/2019 | Jahangir |
| 10,500,322 B2 | 12/2019 | Karch |
| 10,500,323 B2 | 12/2019 | Heuring et al. |
| 10,512,537 B2 | 12/2019 | Corbett et al. |
| 10,525,178 B2 | 1/2020 | Zeng |
| 10,537,670 B2 | 1/2020 | Tuseth et al. |
| 10,537,672 B2 | 1/2020 | Tuseth et al. |
| 10,549,020 B2 | 2/2020 | Spence et al. |
| 10,557,475 B2 | 2/2020 | Roehn |
| 10,561,771 B2 | 2/2020 | Heilman et al. |
| 10,561,772 B2 | 2/2020 | Schumacher |
| 10,561,773 B2 | 2/2020 | Ferrari et al. |
| 10,576,191 B2 | 3/2020 | LaRose |
| 10,584,589 B2 | 3/2020 | Schumacher et al. |
| 10,589,012 B2 | 3/2020 | Toellner et al. |
| 10,589,013 B2 | 3/2020 | Bourque |
| 10,610,626 B2 | 4/2020 | Spanier et al. |
| 10,617,808 B2 | 4/2020 | Hastie et al. |
| 10,632,241 B2 | 4/2020 | Schenck et al. |
| 10,660,998 B2 | 5/2020 | Hodges |
| 10,662,967 B2 | 5/2020 | Scheckel |
| 10,668,195 B2 | 6/2020 | Flores |
| 10,669,855 B2 | 6/2020 | Toellner et al. |
| 10,722,631 B2 | 7/2020 | Salahieh et al. |
| 10,732,583 B2 | 8/2020 | Rudser |
| 10,773,002 B2 | 9/2020 | Siess et al. |
| 10,780,208 B2 | 9/2020 | Siess et al. |
| 10,814,053 B2 | 10/2020 | Throckmorton et al. |
| 10,857,273 B2 | 12/2020 | Hodges et al. |
| 10,857,274 B2 | 12/2020 | Alexander et al. |
| 10,857,275 B2 | 12/2020 | Granegger |
| 10,864,308 B2 | 12/2020 | Muller et al. |
| 11,027,114 B2 | 6/2021 | D'Ambrosio et al. |
| 11,033,729 B2 | 6/2021 | Scheckel et al. |
| 11,045,638 B2 | 6/2021 | Keenan et al. |
| RE48,649 E | 7/2021 | Siess |
| 11,058,863 B2 | 7/2021 | Demou |
| 11,058,865 B2 | 7/2021 | Fitzgerald et al. |
| 11,065,434 B2 | 7/2021 | Egler et al. |
| 11,067,085 B2 | 7/2021 | Granegger et al. |
| 11,092,158 B2 | 8/2021 | Siess et al. |
| 11,097,092 B2 | 8/2021 | Siess et al. |
| 11,103,689 B2 | 8/2021 | Siess et al. |
| 11,103,690 B2 | 8/2021 | Epple |
| 11,107,626 B2 | 8/2021 | Siess et al. |
| 11,116,959 B2 | 9/2021 | Alexander et al. |
| 11,120,908 B2 | 9/2021 | Agnello et al. |
| 11,123,538 B2 | 9/2021 | Epple et al. |
| 11,123,539 B2 | 9/2021 | Pfeffer et al. |
| 11,123,541 B2 | 9/2021 | Corbett et al. |
| 11,129,978 B2 | 9/2021 | Pfeffer et al. |
| 11,131,968 B2 | 9/2021 | Rudser |
| 11,141,579 B2 | 10/2021 | Steingräber |
| 11,147,960 B2 | 10/2021 | Spanier et al. |
| 11,154,701 B2 | 10/2021 | Reyes et al. |
| 11,154,702 B2 | 10/2021 | Kadrolkar et al. |
| 11,160,970 B2 | 11/2021 | Muller et al. |
| 11,167,124 B2 | 11/2021 | Pfeffer et al. |
| 11,173,297 B2 | 11/2021 | Muller |
| 11,179,557 B2 | 11/2021 | Georges et al. |
| 11,185,678 B2 | 11/2021 | Smith et al. |
| 11,185,680 B2 | 11/2021 | Tuval et al. |
| 11,185,682 B2 | 11/2021 | Farnan |
| 11,191,944 B2 | 12/2021 | Tuval et al. |
| 11,191,945 B2 | 12/2021 | Siess et al. |
| 11,197,618 B2 | 12/2021 | Edelman et al. |
| 11,197,989 B2 | 12/2021 | Arslan et al. |
| 11,202,901 B2 | 12/2021 | Barry |
| 11,217,344 B2 | 1/2022 | Agnello |
| 11,219,756 B2 | 1/2022 | Tanner et al. |
| 11,229,786 B2 | 1/2022 | Zeng et al. |
| 11,235,138 B2 | 2/2022 | Gross-Hardt et al. |

(56) References Cited

U.S. PATENT DOCUMENTS

| 11,235,139 B2 | 2/2022 | Kudlik |
| 11,235,140 B2 | 2/2022 | Siess et al. |
| 11,241,568 B2 | 2/2022 | Keenan et al. |
| 11,241,569 B2 | 2/2022 | Delgado, III |
| 11,241,572 B2 | 2/2022 | Dague et al. |
| 11,253,693 B2 | 2/2022 | Pfeffer et al. |
| 11,260,212 B2 | 3/2022 | Tuval et al. |
| 11,260,213 B2 | 3/2022 | Zeng et al. |
| 11,260,215 B2 | 3/2022 | Scheckel et al. |
| 11,273,299 B2 | 3/2022 | Wolman et al. |
| 11,273,300 B2 | 3/2022 | Schafir |
| 11,273,301 B2 | 3/2022 | Pfeffer et al. |
| 11,278,711 B2 | 3/2022 | Liebing |
| 11,280,345 B2 | 3/2022 | Bredenbreuker et al. |
| 11,285,309 B2 | 3/2022 | Tuval et al. |
| 11,285,310 B2 | 3/2022 | Curran et al. |
| 11,285,311 B2 | 3/2022 | Siess et al. |
| 11,291,824 B2 | 4/2022 | Schwammenthal et al. |
| 11,291,825 B2 | 4/2022 | Tuval et al. |
| 11,291,826 B2 | 4/2022 | Tuval et al. |
| 11,298,519 B2 | 4/2022 | Josephy et al. |
| 11,298,520 B2 | 4/2022 | Schwammenthal et al. |
| 11,298,521 B2 | 4/2022 | Schwammenthal et al. |
| 11,298,523 B2 | 4/2022 | Tuval et al. |
| 11,298,524 B2 | 4/2022 | El Katerji et al. |
| 11,298,525 B2 | 4/2022 | Jahangir |
| 11,305,103 B2 | 4/2022 | Larose et al. |
| 11,305,105 B2 | 4/2022 | Corbett et al. |
| 11,311,711 B2 | 4/2022 | Casas et al. |
| 11,311,712 B2 | 4/2022 | Zeng et al. |
| 11,313,228 B2 | 4/2022 | Schumacher et al. |
| 11,316,679 B2 | 4/2022 | Agnello |
| D951,435 S | 5/2022 | Motomura et al. |
| 11,318,295 B2 | 5/2022 | Reyes et al. |
| 11,320,382 B2 | 5/2022 | Aikawa |
| 11,324,395 B2 | 5/2022 | Banik et al. |
| 11,324,940 B2 | 5/2022 | Earles et al. |
| 11,324,941 B2 | 5/2022 | Xu et al. |
| 11,331,082 B2 | 5/2022 | Itoh et al. |
| 11,331,465 B2 | 5/2022 | Epple |
| 11,331,466 B2 | 5/2022 | Keen et al. |
| 11,331,467 B2 | 5/2022 | King et al. |
| 11,331,470 B2 | 5/2022 | Muller et al. |
| 11,337,724 B2 | 5/2022 | Masubuchi et al. |
| 11,338,124 B2 | 5/2022 | Pfeffer et al. |
| 11,338,125 B2 | 5/2022 | Liu et al. |
| 11,344,716 B2 | 5/2022 | Taskin |
| 11,344,717 B2 | 5/2022 | Kallenbach et al. |
| 11,351,356 B2 | 6/2022 | Mohl |
| 11,351,357 B2 | 6/2022 | Mohl |
| 11,351,358 B2 | 6/2022 | Nix et al. |
| 11,351,359 B2 | 6/2022 | Clifton et al. |
| 11,357,438 B2 | 6/2022 | Stewart et al. |
| 11,357,967 B2 | 6/2022 | Zeng et al. |
| 11,357,968 B2 | 6/2022 | El Katerji et al. |
| 11,364,373 B2 | 6/2022 | Corbett et al. |
| 11,368,081 B2 | 6/2022 | Vogt et al. |
| 11,369,785 B2 | 6/2022 | Callaway et al. |
| 11,369,786 B2 | 6/2022 | Menon et al. |
| 11,376,415 B2 | 7/2022 | Mohl |
| 11,376,419 B2 | 7/2022 | Reyes et al. |
| 11,389,639 B2 | 7/2022 | Casas |
| 11,389,641 B2 | 7/2022 | Nguyen et al. |
| 11,413,443 B2 | 8/2022 | Hodges et al. |
| 11,413,444 B2 | 8/2022 | Nix et al. |
| 11,413,445 B2 | 8/2022 | Brown et al. |
| 11,413,446 B2 | 8/2022 | Siess et al. |
| 11,415,150 B2 | 8/2022 | Richert et al. |
| 11,420,041 B2 | 8/2022 | Karch |
| 11,421,701 B2 | 8/2022 | Schumacher et al. |
| 11,428,236 B2 | 8/2022 | McBride et al. |
| 11,433,168 B2 | 9/2022 | Wu et al. |
| 11,434,921 B2 | 9/2022 | McBride et al. |
| 11,434,922 B2 | 9/2022 | Roehn |
| 11,439,806 B2 | 9/2022 | Kimball et al. |
| 11,446,481 B2 | 9/2022 | Wolman et al. |
| 11,446,482 B2 | 9/2022 | Kirchhoff et al. |
| 11,452,859 B2 | 9/2022 | Earles et al. |
| 11,460,030 B2 | 10/2022 | Shambaugh et al. |
| 11,471,662 B2 | 10/2022 | Akkerman et al. |
| 11,471,663 B2 | 10/2022 | Tuval et al. |
| 11,471,665 B2 | 10/2022 | Clifton et al. |
| 11,478,627 B2 | 10/2022 | Siess et al. |
| 11,478,628 B2 | 10/2022 | Muller et al. |
| 11,478,629 B2 | 10/2022 | Harjes et al. |
| 11,484,698 B2 | 11/2022 | Radman |
| 11,484,699 B2 | 11/2022 | Tuval et al. |
| 11,486,400 B2 | 11/2022 | Schumacher |
| 11,491,320 B2 | 11/2022 | Siess |
| 11,491,322 B2 | 11/2022 | Muller et al. |
| 11,497,896 B2 | 11/2022 | Tanner et al. |
| 11,497,906 B2 | 11/2022 | Grace et al. |
| 11,511,101 B2 | 11/2022 | Hastie et al. |
| 11,511,103 B2 | 11/2022 | Salahieh et al. |
| 11,511,104 B2 | 11/2022 | Dur et al. |
| 11,517,726 B2 | 12/2022 | Siess et al. |
| 11,517,736 B2 | 12/2022 | Earles et al. |
| 11,517,737 B2 | 12/2022 | Struthers et al. |
| 11,517,738 B2 | 12/2022 | Wisniewski |
| 11,517,739 B2 | 12/2022 | Toellner |
| 11,517,740 B2 | 12/2022 | Agarwa et al. |
| 11,521,723 B2 | 12/2022 | Liu et al. |
| 11,524,137 B2 | 12/2022 | Jahangir |
| 11,524,153 B2 | 12/2022 | Alexander et al. |
| 11,524,165 B2 | 12/2022 | Tan et al. |
| 11,527,322 B2 | 12/2022 | Agnello et al. |
| 11,529,062 B2 | 12/2022 | Moyer et al. |
| 11,534,596 B2 | 12/2022 | Schafir et al. |
| 11,554,260 B2 | 1/2023 | Reyes et al. |
| 11,565,103 B2 | 1/2023 | Farago et al. |
| 11,569,015 B2 | 1/2023 | Mourran et al. |
| 11,572,879 B2 | 2/2023 | Mohl |
| 11,574,741 B2 | 2/2023 | Tan et al. |
| 11,577,067 B2 | 2/2023 | Breidall et al. |
| 11,577,068 B2 | 2/2023 | Spence et al. |
| 11,581,083 B2 | 2/2023 | El Katerji et al. |
| 11,583,659 B2 | 2/2023 | Pfeffer et al. |
| 11,583,670 B2 | 2/2023 | Pfeifer et al. |
| 11,583,671 B2 | 2/2023 | Nguyen et al. |
| 11,583,672 B2 | 2/2023 | Weber et al. |
| 11,587,337 B2 | 2/2023 | Lemay et al. |
| 11,590,336 B2 | 2/2023 | Harjes et al. |
| 11,590,337 B2 | 2/2023 | Granegger et al. |
| 11,590,338 B2 | 2/2023 | Barry |
| 11,592,028 B2 | 2/2023 | Schumacher et al. |
| 11,596,727 B2 | 3/2023 | Siess et al. |
| 11,602,627 B2 | 3/2023 | Leonhardt |
| 11,617,876 B2 | 4/2023 | Scheckel et al. |
| 11,622,695 B1 | 4/2023 | Adriola et al. |
| 11,628,293 B2 | 4/2023 | Gandhi et al. |
| 11,632,015 B2 | 4/2023 | Sconzert et al. |
| 11,633,586 B2 | 4/2023 | Tanner et al. |
| 11,638,813 B2 | 5/2023 | West |
| 11,639,722 B2 | 5/2023 | Medvedev et al. |
| 11,642,511 B2 | 5/2023 | Delgado, III |
| 11,648,386 B2 | 5/2023 | Poirer |
| 11,648,387 B2 | 5/2023 | Schwammenthal et al. |
| 11,648,388 B2 | 5/2023 | Siess et al. |
| 11,648,389 B2 | 5/2023 | Wang et al. |
| 11,648,390 B2 | 5/2023 | Spanier et al. |
| 11,648,391 B2 | 5/2023 | Schwammenthal et al. |
| 11,648,392 B2 | 5/2023 | Tuval et al. |
| 11,648,393 B2 | 5/2023 | Taskin et al. |
| 11,653,841 B2 | 5/2023 | Reyes et al. |
| 11,654,273 B2 | 5/2023 | Granegger et al. |
| 11,654,275 B2 | 5/2023 | Brandt |
| 11,654,276 B2 | 5/2023 | Fitzgerald et al. |
| 11,660,441 B2 | 5/2023 | Fitzgerald et al. |
| 11,666,746 B2 | 6/2023 | Ferrari et al. |
| 11,666,747 B2 | 6/2023 | Tuval et al. |
| 11,666,748 B2 | 6/2023 | Kronstedt et al. |
| 11,668,321 B2 | 6/2023 | Richert et al. |
| 11,674,517 B2 | 6/2023 | Mohl |
| 11,676,718 B2 | 6/2023 | Agnello et al. |

(56) References Cited

U.S. PATENT DOCUMENTS

| | | |
|---|---|---|
| 11,679,234 B2 | 6/2023 | King et al. |
| 11,679,249 B2 | 6/2023 | Scheckel et al. |
| 11,679,250 B2 | 6/2023 | Alexander et al. |
| 11,684,275 B2 | 6/2023 | Tuval et al. |
| 11,684,276 B2 | 6/2023 | Cros et al. |
| 11,684,769 B2 | 6/2023 | Harjes et al. |
| 11,690,521 B2 | 7/2023 | Tuval et al. |
| 11,690,996 B2 | 7/2023 | Siess et al. |
| 11,694,539 B2 | 7/2023 | Kudlik et al. |
| 11,694,813 B2 | 7/2023 | El Katerji et al. |
| 11,696,782 B2 | 7/2023 | Carlson et al. |
| 11,697,016 B2 | 7/2023 | Epple |
| 11,701,510 B2 | 7/2023 | Demou |
| 11,702,938 B2 | 7/2023 | Schumacher et al. |
| 11,703,064 B2 | 7/2023 | Bredenbreuker et al. |
| 11,707,617 B2 | 7/2023 | Reyes et al. |
| 11,708,833 B2 | 7/2023 | McBride et al. |
| 11,712,167 B2 | 8/2023 | Medvedev et al. |
| 11,724,091 B2 | 8/2023 | Siess et al. |
| 11,744,987 B2 | 9/2023 | Siess et al. |
| 11,745,005 B2 | 9/2023 | Delgado, III |
| 11,746,906 B1 | 9/2023 | Balta et al. |
| 11,752,322 B2 | 9/2023 | Aboulhosn et al. |
| 11,752,323 B2 | 9/2023 | Edwards et al. |
| 11,754,075 B2 | 9/2023 | Schuelke et al. |
| 11,754,077 B1 | 9/2023 | Mohl |
| 11,759,612 B2 | 9/2023 | Tanner et al. |
| 11,759,622 B2 | 9/2023 | Siess et al. |
| 11,766,555 B2 | 9/2023 | Matthes et al. |
| D1,001,145 S | 10/2023 | Lussier et al. |
| D1,001,146 S | 10/2023 | Lussier et al. |
| 11,771,884 B2 | 10/2023 | Siess et al. |
| 11,771,885 B2 | 10/2023 | Liu et al. |
| 11,779,234 B2 | 10/2023 | Harjes et al. |
| 11,779,751 B2 | 10/2023 | Earles et al. |
| 11,781,550 B2 | 10/2023 | Siess et al. |
| 11,786,386 B2 | 10/2023 | Brady et al. |
| 11,786,700 B2 | 10/2023 | Pfeffer et al. |
| 11,786,720 B2 | 10/2023 | Muller |
| 11,790,487 B2 | 10/2023 | Barbato et al. |
| 11,793,994 B2 | 10/2023 | Josephy et al. |
| 11,804,767 B2 | 10/2023 | Vogt et al. |
| 11,806,116 B2 | 11/2023 | Tuval et al. |
| 11,806,117 B2 | 11/2023 | Tuval et al. |
| 11,806,517 B2 | 11/2023 | Petersen |
| 11,806,518 B2 | 11/2023 | Michelena et al. |
| 11,813,079 B2 | 11/2023 | Lau et al. |
| 11,813,443 B2 | 11/2023 | Hanson et al. |
| 11,813,444 B2 | 11/2023 | Siess et al. |
| 11,813,445 B2 | 11/2023 | Alexander et al. |
| 11,818,782 B2 | 11/2023 | Doudian et al. |
| 11,819,678 B2 | 11/2023 | Siess et al. |
| 11,824,381 B2 | 11/2023 | Conyers et al. |
| 11,826,127 B2 | 11/2023 | Casas |
| 11,832,793 B2 | 12/2023 | McWeeney et al. |
| 11,832,868 B2 | 12/2023 | Smail et al. |
| 11,833,278 B2 | 12/2023 | Siess et al. |
| 11,833,342 B2 | 12/2023 | Tanner et al. |
| 11,837,364 B2 | 12/2023 | Lee et al. |
| 11,839,754 B2 | 12/2023 | Tuval et al. |
| 11,844,592 B2 | 12/2023 | Tuval et al. |
| 11,844,940 B2 | 12/2023 | D'Ambrosio et al. |
| 11,850,073 B2 | 12/2023 | Wright et al. |
| 11,850,412 B2 | 12/2023 | Grauwinkel et al. |
| 11,850,413 B2 | 12/2023 | Zeng et al. |
| 11,850,414 B2 | 12/2023 | Schenck et al. |
| 11,850,415 B2 | 12/2023 | Schwammenthal et al. |
| D1,012,284 S | 1/2024 | Glaser et al. |
| 11,857,345 B2 | 1/2024 | Hanson et al. |
| 11,857,743 B2 | 1/2024 | Fantuzzi et al. |
| 11,857,777 B2 | 1/2024 | Earles et al. |
| 11,864,878 B2 | 1/2024 | Duval et al. |
| 11,865,238 B2 | 1/2024 | Siess et al. |
| 11,872,384 B2 | 1/2024 | Cotter |
| 11,883,005 B2 | 1/2024 | Golden et al. |
| 11,883,207 B2 | 1/2024 | El Katerji et al. |
| 11,883,310 B2 | 1/2024 | Nolan et al. |
| 11,883,641 B2 | 1/2024 | Dur et al. |
| D1,014,552 S | 2/2024 | Lussier et al. |
| 11,890,082 B2 | 2/2024 | Cros et al. |
| 11,890,212 B2 | 2/2024 | Gilmartin et al. |
| 11,896,199 B2 | 2/2024 | Lent et al. |
| 11,896,482 B2 | 2/2024 | Delaloye et al. |
| 11,898,642 B2 | 2/2024 | Stanton et al. |
| 11,900,660 B2 | 2/2024 | Saito et al. |
| 11,903,657 B2 | 2/2024 | Geric et al. |
| 11,904,104 B2 | 2/2024 | Jahangir |
| 11,906,411 B2 | 2/2024 | Graichen et al. |
| 11,911,550 B2 | 2/2024 | Itamochi et al. |
| 11,911,579 B2 | 2/2024 | Tanner et al. |
| D1,017,634 S | 3/2024 | Lussier et al. |
| D1,017,699 S | 3/2024 | Moore et al. |
| 11,918,470 B2 | 3/2024 | Jarral et al. |
| 11,918,496 B2 | 3/2024 | Folan |
| 11,918,726 B2 | 3/2024 | Siess et al. |
| 11,918,800 B2 | 3/2024 | Muller et al. |
| 11,923,078 B2 | 3/2024 | Fallen et al. |
| 11,923,093 B2 | 3/2024 | Moffitt et al. |
| 11,925,356 B2 | 3/2024 | Anderson et al. |
| 11,925,570 B2 | 3/2024 | Lydecker et al. |
| 11,925,794 B2 | 3/2024 | Malkin et al. |
| 11,925,795 B2 | 3/2024 | Muller et al. |
| 11,925,796 B2 | 3/2024 | Tanner et al. |
| 11,925,797 B2 | 3/2024 | Tanner et al. |
| 11,931,073 B2 | 3/2024 | Walsh et al. |
| 11,931,528 B2 | 3/2024 | Rohl et al. |
| 11,931,588 B2 | 3/2024 | Aghassian |
| 11,938,311 B2 | 3/2024 | Corbett et al. |
| 11,944,805 B2 | 4/2024 | Stotz |
| 11,957,892 B2 | 4/2024 | Siess et al. |
| 11,980,385 B2 | 5/2024 | Haselman |
| 11,986,274 B2 | 5/2024 | Edelman |
| 11,986,604 B2 | 5/2024 | Siess |
| 12,005,248 B2 | 6/2024 | Vogt et al. |
| 12,011,583 B2 | 6/2024 | Wang |
| 12,017,058 B2 | 6/2024 | Kerkhoffs et al. |
| 12,017,076 B2 | 6/2024 | Tan et al. |
| 12,023,476 B2 | 7/2024 | Tuval et al. |
| 12,023,477 B2 | 7/2024 | Siess |
| 12,029,891 B2 | 7/2024 | Siess et al. |
| 12,053,624 B2 | 8/2024 | Alexander et al. |
| 12,059,559 B2 | 8/2024 | Muller et al. |
| 12,064,120 B2 | 8/2024 | Hajjar et al. |
| 12,064,611 B2 | 8/2024 | D'Ambrosio et al. |
| 12,064,614 B2 | 8/2024 | Agah et al. |
| 12,064,615 B2 | 8/2024 | Stotz et al. |
| 12,064,616 B2 | 8/2024 | Spanier et al. |
| D1,043,730 S | 9/2024 | Lussier et al. |
| D1,043,731 S | 9/2024 | Lussier et al. |
| 12,076,544 B2 | 9/2024 | Siess et al. |
| 12,076,549 B2 | 9/2024 | Stotz et al. |
| 12,076,550 B2 | 9/2024 | Edwards et al. |
| 12,090,310 B2 | 9/2024 | Alexander et al. |
| 12,090,314 B2 | 9/2024 | Tuval et al. |
| 12,092,114 B2 | 9/2024 | Siess |
| 12,097,016 B2 | 9/2024 | Goldvasser |
| 12,102,815 B2 | 10/2024 | Dhaliwal et al. |
| 12,104,600 B2 | 10/2024 | Mohl |
| 12,107,474 B2 | 10/2024 | Vollmer |
| 12,117,007 B1 | 10/2024 | Mohl |
| 12,121,713 B2 | 10/2024 | Calomeni et al. |
| 12,133,976 B2 | 11/2024 | Malone et al. |
| 12,138,438 B2 | 11/2024 | Alexander et al. |
| 12,144,650 B2 | 11/2024 | Spanier et al. |
| 12,144,936 B2 | 11/2024 | Tao et al. |
| 12,144,976 B2 | 11/2024 | Baumbach et al. |
| 12,151,092 B2 | 11/2024 | Alexander et al. |
| 12,161,854 B2 | 12/2024 | Earles et al. |
| 12,161,855 B2 | 12/2024 | Hastie et al. |
| 12,161,857 B2 | 12/2024 | Saul et al. |
| 12,171,993 B2 | 12/2024 | Higgins et al. |
| 12,178,554 B2 | 12/2024 | Stotz et al. |
| 12,179,009 B2 | 12/2024 | El Katerji et al. |
| 12,183,459 B2 | 12/2024 | Agnello et al. |

(56)     References Cited

U.S. PATENT DOCUMENTS

| | | |
|---|---|---|
| 12,194,287 B2 | 1/2025 | Kassel et al. |
| 12,196,210 B2 | 1/2025 | Siess et al. |
| 12,201,821 B2 | 1/2025 | Schlebusch et al. |
| 12,201,823 B2 | 1/2025 | Baumbach et al. |
| 12,207,906 B2 | 1/2025 | Tuval et al. |
| 12,211,615 B2 | 1/2025 | Nix et al. |
| D1,060,379 S | 2/2025 | Lussier et al. |
| 12,213,771 B2 | 2/2025 | Curran et al. |
| 12,217,850 B2 | 2/2025 | Agnello |
| 12,222,267 B2 | 2/2025 | Stotz et al. |
| 12,233,251 B2 | 2/2025 | Siess et al. |
| 12,241,480 B2 | 3/2025 | Corbett et al. |
| 12,251,551 B2 | 3/2025 | Liu et al. |
| 12,257,424 B2 | 3/2025 | Schlebusch et al. |
| 12,263,330 B2 | 4/2025 | D'Ambrosio et al. |
| 12,263,333 B2 | 4/2025 | Stotz et al. |
| 12,263,334 B2 | 4/2025 | Corbett et al. |
| 12,268,861 B2 | 4/2025 | D'Ambrosio et al. |
| 12,290,673 B2 | 5/2025 | Jahangir |
| 12,290,676 B2 | 5/2025 | Farago et al. |
| 12,296,158 B2 | 5/2025 | Higgins et al. |
| 12,296,159 B2 | 5/2025 | Schilling et al. |
| 12,303,678 B2 | 5/2025 | Kerkhoffs et al. |
| 12,303,680 B2 | 5/2025 | Siess et al. |
| 12,310,621 B2 | 5/2025 | Murphy |
| 12,310,708 B2 | 5/2025 | Schlebusch et al. |
| 12,311,160 B2 | 5/2025 | Schlebusch et al. |
| 12,318,551 B2 | 6/2025 | Jahangir |
| 12,324,906 B2 | 6/2025 | Baumbach et al. |
| 12,329,501 B2 | 6/2025 | Moyer et al. |
| 12,329,956 B2 | 6/2025 | Sunagawa |
| 12,329,958 B2 | 6/2025 | Siess et al. |
| 12,329,959 B2 | 6/2025 | Hassan et al. |
| 12,337,163 B2 | 6/2025 | Radman |
| 12,343,516 B2 | 7/2025 | Cook |
| 12,343,518 B2 | 7/2025 | Tuval et al. |
| 12,343,519 B2 | 7/2025 | Siess et al. |
| 12,364,799 B2 | 7/2025 | Siess et al. |
| 12,364,850 B2 | 7/2025 | Siess et al. |
| 12,364,854 B2 | 7/2025 | Wang |
| D1,090,610 S | 8/2025 | Kroeker et al. |
| 12,377,256 B2 | 8/2025 | Stotz et al. |
| 12,383,704 B2 | 8/2025 | Ship et al. |
| 12,383,724 B2 | 8/2025 | Kirchoff et al. |
| 12,383,727 B2 | 8/2025 | Kassel et al. |
| 12,390,168 B2 | 8/2025 | Katerji et al. |
| 12,390,633 B2 | 8/2025 | Stotz et al. |
| 12,397,099 B2 | 8/2025 | Germain et al. |
| 12,397,146 B2 | 8/2025 | Hart et al. |
| 12,397,147 B2 | 8/2025 | Siess et al. |
| D1,092,492 S | 9/2025 | Lussier et al. |
| D1,092,716 S | 9/2025 | Bernazani |
| 12,409,311 B2 | 9/2025 | Jahangir et al. |
| 12,409,313 B2 | 9/2025 | Eggen et al. |
| 12,415,056 B2 | 9/2025 | Siess et al. |
| 12,420,076 B2 | 9/2025 | Spanier et al. |
| 12,420,079 B2 | 9/2025 | Das et al. |
| 12,424,306 B2 | 9/2025 | Liu et al. |
| 12,424,315 B2 | 9/2025 | Nix et al. |
| 12,434,060 B2 | 10/2025 | Tan et al. |
| 12,440,663 B2 | 10/2025 | Tuval et al. |
| 12,440,665 B2 | 10/2025 | Tuval et al. |
| 12,445,278 B2 | 10/2025 | Agnello |
| 12,447,309 B2 | 10/2025 | Siess et al. |
| 12,447,327 B2 | 10/2025 | Stotz |
| 12,451,230 B2 | 10/2025 | El Katerji et al. |
| 12,453,847 B2 | 10/2025 | Scheffler et al. |
| 12,453,848 B2 | 10/2025 | Tuval et al. |
| 12,453,849 B2 | 10/2025 | VanCamp et al. |
| D1,101,157 S | 11/2025 | Qi et al. |
| 12,458,792 B2 | 11/2025 | Zarins |
| 12,465,744 B2 | 11/2025 | Schuelke et al. |
| 12,476,002 B2 | 11/2025 | El Katerji et al. |
| 12,478,266 B2 | 11/2025 | Edelman et al. |
| 12,478,267 B2 | 11/2025 | Schlebusch et al. |
| 12,478,775 B2 | 11/2025 | Schlebusch et al. |
| 12,478,776 B2 | 11/2025 | Stotz |
| 12,491,357 B2 | 12/2025 | Baumbach et al. |
| 2001/0009645 A1 | 7/2001 | Noda |
| 2001/0016686 A1 | 8/2001 | Okada et al. |
| 2001/0037093 A1 | 11/2001 | Benkowski et al. |
| 2001/0039828 A1 | 11/2001 | Shin et al. |
| 2001/0041934 A1 | 11/2001 | Yamazaki et al. |
| 2002/0022785 A1 | 2/2002 | Romano |
| 2002/0076322 A1 | 6/2002 | Maeda et al. |
| 2002/0082585 A1 | 6/2002 | Carroll et al. |
| 2002/0093412 A1 | 7/2002 | Morrison |
| 2002/0147495 A1 | 10/2002 | Petroff |
| 2002/0151761 A1 | 10/2002 | Viole et al. |
| 2002/0153664 A1 | 10/2002 | Schroeder |
| 2003/0060685 A1 | 3/2003 | Houser |
| 2003/0069465 A1 | 4/2003 | Benkowski et al. |
| 2003/0091450 A1 | 5/2003 | Davis et al. |
| 2003/0100816 A1 | 5/2003 | Siess |
| 2003/0111800 A1 | 6/2003 | Kreutzer |
| 2003/0130581 A1 | 7/2003 | Salo et al. |
| 2003/0139643 A1 | 7/2003 | Smith et al. |
| 2003/0167002 A1 | 9/2003 | Nagar et al. |
| 2003/0191357 A1 | 10/2003 | Frazier |
| 2003/0199727 A1 | 10/2003 | Burke |
| 2004/0022640 A1 | 2/2004 | Siess et al. |
| 2004/0044266 A1* | 3/2004 | Siess ............... A61M 60/216 |
| | | 600/16 |
| 2004/0065143 A1 | 4/2004 | Husher |
| 2004/0102674 A1 | 5/2004 | Zadini et al. |
| 2004/0115038 A1 | 6/2004 | Nuesser et al. |
| 2004/0124979 A1 | 7/2004 | Medema |
| 2004/0130009 A1 | 7/2004 | Tangpuz |
| 2004/0167376 A1 | 8/2004 | Peters et al. |
| 2004/0167410 A1 | 8/2004 | Hettrick |
| 2004/0225177 A1 | 11/2004 | Coleman et al. |
| 2004/0234391 A1 | 11/2004 | Izraelev |
| 2004/0241019 A1 | 12/2004 | Goldowsky |
| 2004/0260346 A1 | 12/2004 | Overall et al. |
| 2005/0001324 A1 | 1/2005 | Dunn |
| 2005/0006083 A1 | 1/2005 | Chen et al. |
| 2005/0008509 A1 | 1/2005 | Chang |
| 2005/0019167 A1 | 1/2005 | Nusser et al. |
| 2005/0046044 A1 | 3/2005 | Theuss |
| 2005/0085683 A1 | 4/2005 | Bolling et al. |
| 2005/0107658 A1 | 5/2005 | Brockway |
| 2005/0126268 A1 | 6/2005 | Ouriev et al. |
| 2005/0220636 A1 | 10/2005 | Henein et al. |
| 2005/0254976 A1 | 11/2005 | Carrier et al. |
| 2005/0267322 A1 | 12/2005 | LaRose |
| 2006/0030809 A1 | 2/2006 | Barzilay et al. |
| 2006/0062672 A1 | 3/2006 | McBride et al. |
| 2006/0108697 A1 | 5/2006 | Wang |
| 2006/0108901 A1 | 5/2006 | Baba et al. |
| 2006/0122583 A1 | 6/2006 | Pesach et al. |
| 2006/0155158 A1 | 7/2006 | Aboul-Hosn |
| 2006/0196277 A1 | 9/2006 | Allen et al. |
| 2006/0224110 A1 | 10/2006 | Scott et al. |
| 2006/0229488 A1 | 10/2006 | Ayre et al. |
| 2006/0276682 A1 | 12/2006 | Bolling et al. |
| 2006/0287600 A1 | 12/2006 | McEowen |
| 2006/0287604 A1 | 12/2006 | Hickey |
| 2007/0004959 A1 | 1/2007 | Carrier et al. |
| 2007/0060787 A1 | 3/2007 | Peters et al. |
| 2007/0069354 A1 | 3/2007 | Dangelmaier |
| 2007/0073352 A1 | 3/2007 | Euler et al. |
| 2007/0088214 A1 | 4/2007 | Shuros et al. |
| 2007/0142696 A1 | 6/2007 | Crosby et al. |
| 2007/0156006 A1 | 7/2007 | Smith et al. |
| 2007/0255352 A1 | 11/2007 | Roline et al. |
| 2007/0266778 A1 | 11/2007 | Corey et al. |
| 2007/0282209 A1 | 12/2007 | Lui et al. |
| 2007/0299325 A1 | 12/2007 | Farrell et al. |
| 2008/0015517 A1 | 1/2008 | Geistert et al. |
| 2008/0058925 A1 | 3/2008 | Cohen |
| 2008/0082005 A1 | 4/2008 | Stern et al. |
| 2008/0086027 A1 | 4/2008 | Siess et al. |
| 2008/0091239 A1 | 4/2008 | Johansson et al. |
| 2008/0097595 A1 | 4/2008 | Gabbay |

(56)　　　　　References Cited

U.S. PATENT DOCUMENTS

| | | |
|---|---|---|
| 2008/0102096 A1 | 5/2008 | Molin et al. |
| 2008/0108901 A1 | 5/2008 | Baba et al. |
| 2008/0108930 A1 | 5/2008 | Weitzel et al. |
| 2008/0114339 A1 | 5/2008 | McBride et al. |
| 2008/0133006 A1 | 6/2008 | Crosby et al. |
| 2008/0146996 A1 | 6/2008 | Smisson |
| 2008/0210016 A1 | 9/2008 | Zwirn et al. |
| 2008/0248614 A1 | 10/2008 | Yang |
| 2008/0262289 A1 | 10/2008 | Goldowsky |
| 2008/0262361 A1 | 10/2008 | Gutfinger et al. |
| 2008/0269822 A1 | 10/2008 | Ljungstrom et al. |
| 2008/0275339 A1 | 11/2008 | Thiemann et al. |
| 2008/0287799 A1 | 11/2008 | Hall |
| 2008/0292478 A1 | 11/2008 | Baykut et al. |
| 2008/0306328 A1* | 12/2008 | Ercolani ............. A61M 60/857 |
| | | 600/16 |
| 2009/0004037 A1 | 1/2009 | Ito |
| 2009/0024042 A1 | 1/2009 | Nunez et al. |
| 2009/0025459 A1 | 1/2009 | Zhang et al. |
| 2009/0064755 A1 | 3/2009 | Fleischli et al. |
| 2009/0105799 A1 | 4/2009 | Hekmat et al. |
| 2009/0112312 A1 | 4/2009 | Larose et al. |
| 2009/0131765 A1 | 5/2009 | Roschak et al. |
| 2009/0203957 A1 | 8/2009 | LaRose et al. |
| 2009/0204163 A1 | 8/2009 | Shuros et al. |
| 2009/0204205 A1 | 8/2009 | Larose et al. |
| 2009/0226328 A1 | 9/2009 | Morello |
| 2009/0312650 A1 | 12/2009 | Maile et al. |
| 2010/0010354 A1 | 1/2010 | Skerl et al. |
| 2010/0041939 A1 | 2/2010 | Siess |
| 2010/0082099 A1 | 4/2010 | Vodermayer et al. |
| 2010/0087742 A1 | 4/2010 | Bishop et al. |
| 2010/0160801 A1 | 6/2010 | Takatani et al. |
| 2010/0191035 A1 | 7/2010 | Kang et al. |
| 2010/0219967 A1 | 9/2010 | Kaufmann |
| 2010/0222632 A1 | 9/2010 | Poirier |
| 2010/0222633 A1 | 9/2010 | Poirier |
| 2010/0222635 A1 | 9/2010 | Poirier |
| 2010/0222878 A1 | 9/2010 | Poirier |
| 2010/0268017 A1* | 10/2010 | Siess ................... A61M 60/857 |
| | | 600/16 |
| 2010/0298625 A1* | 11/2010 | Reichenbach .... A61M 25/0032 |
| | | 600/16 |
| 2010/0324378 A1 | 12/2010 | Tran et al. |
| 2011/0004075 A1 | 1/2011 | Stahmann et al. |
| 2011/0022057 A1 | 1/2011 | Eigler et al. |
| 2011/0071336 A1 | 3/2011 | Yomtov |
| 2011/0144744 A1 | 6/2011 | Wampler |
| 2011/0160516 A1 | 6/2011 | Dague |
| 2011/0172505 A1 | 7/2011 | Kim |
| 2011/0184224 A1 | 7/2011 | Garrigue |
| 2011/0184301 A1 | 7/2011 | Holmstrom |
| 2011/0186943 A1 | 8/2011 | Pahl |
| 2011/0218435 A1 | 9/2011 | Srinivasan et al. |
| 2011/0230068 A1 | 9/2011 | Pahl |
| 2011/0230821 A1 | 9/2011 | Babic |
| 2011/0237863 A1 | 9/2011 | Ricci et al. |
| 2011/0238172 A1 | 9/2011 | Akdis |
| 2012/0022645 A1 | 1/2012 | Burke |
| 2012/0029265 A1 | 2/2012 | LaRose |
| 2012/0029408 A1 | 2/2012 | Beaudin |
| 2012/0035645 A1 | 2/2012 | Gross |
| 2012/0084024 A1 | 4/2012 | Norcross, Jr. |
| 2012/0088954 A1 | 4/2012 | Foster |
| 2012/0093628 A1 | 4/2012 | Liebing |
| 2012/0134793 A1 | 5/2012 | Wu et al. |
| 2012/0150089 A1 | 6/2012 | Penka et al. |
| 2012/0150291 A1 | 6/2012 | Aber |
| 2012/0172655 A1 | 7/2012 | Campbell et al. |
| 2012/0178986 A1 | 7/2012 | Campbell et al. |
| 2012/0197141 A1 | 8/2012 | Vanney |
| 2012/0203476 A1 | 8/2012 | Dam |
| 2012/0245404 A1 | 9/2012 | Smith |
| 2012/0247200 A1 | 10/2012 | Ahonen et al. |
| 2012/0283506 A1 | 11/2012 | Meister et al. |
| 2012/0310036 A1 | 12/2012 | Peters et al. |
| 2012/0310037 A1 | 12/2012 | Choi et al. |
| 2012/0330214 A1 | 12/2012 | Peters et al. |
| 2013/0041204 A1 | 2/2013 | Heilman et al. |
| 2013/0046129 A1 | 2/2013 | Medvedev et al. |
| 2013/0053623 A1 | 2/2013 | Evans |
| 2013/0066141 A1 | 3/2013 | Doerr et al. |
| 2013/0066142 A1 | 3/2013 | Doerr et al. |
| 2013/0072846 A1 | 3/2013 | Heide et al. |
| 2013/0085318 A1 | 4/2013 | Toellner |
| 2013/0116575 A1 | 5/2013 | Mickle et al. |
| 2013/0144379 A1 | 6/2013 | Najafi et al. |
| 2013/0209292 A1 | 8/2013 | Baykut et al. |
| 2013/0281761 A1 | 10/2013 | Kapur |
| 2013/0289334 A1 | 10/2013 | Badstibner |
| 2013/0289376 A1 | 10/2013 | Lang |
| 2013/0303830 A1 | 11/2013 | Zeng et al. |
| 2013/0303831 A1* | 11/2013 | Evans ................ A61M 60/865 |
| | | 600/16 |
| 2013/0303832 A1 | 11/2013 | Wampler |
| 2013/0304404 A1 | 11/2013 | Dam |
| 2013/0330219 A1 | 12/2013 | LaRose et al. |
| 2014/0005467 A1 | 1/2014 | Farnan et al. |
| 2014/0013852 A1 | 1/2014 | Brown et al. |
| 2014/0030122 A1 | 1/2014 | Ozaki |
| 2014/0051908 A1 | 2/2014 | Khanal et al. |
| 2014/0079557 A1 | 3/2014 | LaRose et al. |
| 2014/0100414 A1 | 4/2014 | Tamez et al. |
| 2014/0107399 A1 | 4/2014 | Spence |
| 2014/0114202 A1 | 4/2014 | Hein et al. |
| 2014/0128659 A1 | 5/2014 | Heuring et al. |
| 2014/0167545 A1 | 6/2014 | Bremner et al. |
| 2014/0194717 A1 | 7/2014 | Wildhirt et al. |
| 2014/0200389 A1 | 7/2014 | Yanai et al. |
| 2014/0207232 A1 | 7/2014 | Garrigue |
| 2014/0243688 A1 | 8/2014 | Caron et al. |
| 2014/0275720 A1 | 9/2014 | Ferrari |
| 2014/0275721 A1 | 9/2014 | Yanai et al. |
| 2014/0275727 A1 | 9/2014 | Bonde |
| 2014/0296677 A1 | 10/2014 | McEowen |
| 2014/0303426 A1 | 10/2014 | Kerkhoffs et al. |
| 2014/0330069 A1 | 11/2014 | Hastings et al. |
| 2014/0341726 A1 | 11/2014 | Wu et al. |
| 2014/0342203 A1 | 11/2014 | Elian |
| 2014/0368942 A1 | 12/2014 | Harrell |
| 2015/0027224 A1 | 1/2015 | Schiffer |
| 2015/0031936 A1 | 1/2015 | LaRose et al. |
| 2015/0032007 A1 | 1/2015 | Ottevanger et al. |
| 2015/0051435 A1 | 2/2015 | Siess et al. |
| 2015/0051438 A1 | 2/2015 | Taskin |
| 2015/0080743 A1 | 3/2015 | Siess |
| 2015/0099923 A1 | 4/2015 | Magovern et al. |
| 2015/0141832 A1 | 5/2015 | Yu et al. |
| 2015/0141842 A1 | 5/2015 | Spanier et al. |
| 2015/0157216 A1 | 6/2015 | Stigall et al. |
| 2015/0171694 A1 | 6/2015 | Dallas |
| 2015/0174307 A1 | 6/2015 | Eckman et al. |
| 2015/0190092 A1 | 7/2015 | Mori |
| 2015/0196076 A1 | 7/2015 | Billingslea |
| 2015/0201900 A1 | 7/2015 | Syed |
| 2015/0250935 A1 | 9/2015 | Anderson et al. |
| 2015/0273184 A1 | 10/2015 | Scott et al. |
| 2015/0290372 A1 | 10/2015 | Muller et al. |
| 2015/0290373 A1 | 10/2015 | Rudser et al. |
| 2015/0306290 A1 | 10/2015 | Rosenberg et al. |
| 2015/0306291 A1 | 10/2015 | Bonde et al. |
| 2015/0307344 A1 | 10/2015 | Ernst |
| 2015/0327921 A1 | 11/2015 | Govari |
| 2015/0335804 A1 | 11/2015 | Marseille et al. |
| 2015/0343179 A1 | 12/2015 | Schumacher et al. |
| 2015/0362017 A1 | 12/2015 | Bell |
| 2015/0365738 A1 | 12/2015 | Purvis et al. |
| 2016/0000983 A1 | 1/2016 | Mohl et al. |
| 2016/0008531 A1 | 1/2016 | Wang et al. |
| 2016/0022889 A1 | 1/2016 | Bluvshtein et al. |
| 2016/0022890 A1 | 1/2016 | Schwammenthal et al. |
| 2016/0030649 A1 | 2/2016 | Zeng |
| 2016/0038663 A1 | 2/2016 | Taskin et al. |
| 2016/0045165 A1 | 2/2016 | Braido et al. |

(56)  References Cited

U.S. PATENT DOCUMENTS

| | | |
|---|---|---|
| 2016/0045654 A1 | 2/2016 | Connor |
| 2016/0067395 A1 | 3/2016 | Jimenez et al. |
| 2016/0095968 A1 | 4/2016 | Rudser |
| 2016/0101224 A1 | 4/2016 | Akkerman |
| 2016/0101230 A1 | 4/2016 | Ochsner et al. |
| 2016/0144089 A1 | 5/2016 | Woo et al. |
| 2016/0144166 A1 | 5/2016 | Decréet al. |
| 2016/0151553 A1 | 6/2016 | Bonde |
| 2016/0166747 A1 | 6/2016 | Frazier et al. |
| 2016/0184499 A1 | 6/2016 | Ricci |
| 2016/0213828 A1 | 7/2016 | Sievers |
| 2016/0223086 A1 | 8/2016 | Balsells et al. |
| 2016/0250399 A1 | 9/2016 | Tiller et al. |
| 2016/0256620 A1 | 9/2016 | Scheckel et al. |
| 2016/0278856 A1 | 9/2016 | Panescu |
| 2016/0279311 A1 | 9/2016 | Cecere et al. |
| 2016/0302672 A1 | 10/2016 | Kuri |
| 2016/0303299 A1 | 10/2016 | Muller |
| 2016/0317043 A1 | 11/2016 | Campo |
| 2016/0338629 A1 | 11/2016 | Doerr |
| 2016/0367739 A1 | 12/2016 | Wiesener et al. |
| 2016/0375187 A1 | 12/2016 | Lee et al. |
| 2017/0010144 A1 | 1/2017 | Lenner et al. |
| 2017/0021069 A1 | 1/2017 | Hodges |
| 2017/0021070 A1 | 1/2017 | Petersen |
| 2017/0021074 A1 | 1/2017 | Opfermann et al. |
| 2017/0035952 A1 | 2/2017 | Muller |
| 2017/0043074 A1 | 2/2017 | Siess |
| 2017/0049945 A1 | 2/2017 | Halvorsen et al. |
| 2017/0049947 A1 | 2/2017 | Corbett et al. |
| 2017/0080136 A1 | 3/2017 | Janeczek et al. |
| 2017/0086780 A1 | 3/2017 | Sokulin et al. |
| 2017/0087286 A1 | 3/2017 | Spanier et al. |
| 2017/0087288 A1 | 3/2017 | Groß-Hardt et al. |
| 2017/0098491 A1 | 4/2017 | Ziaie et al. |
| 2017/0112985 A1 | 4/2017 | Yomtov |
| 2017/0128644 A1 | 5/2017 | Foster |
| 2017/0128646 A1 | 5/2017 | Karch |
| 2017/0136164 A1 | 5/2017 | Yeatts |
| 2017/0136225 A1 | 5/2017 | Siess et al. |
| 2017/0143952 A1 | 5/2017 | Siess et al. |
| 2017/0157309 A1 | 6/2017 | Begg et al. |
| 2017/0202575 A1 | 7/2017 | Stanfield et al. |
| 2017/0209633 A1 | 7/2017 | Cohen |
| 2017/0224279 A1 | 8/2017 | Cahan et al. |
| 2017/0232169 A1 | 8/2017 | Muller |
| 2017/0239407 A1 | 8/2017 | Hayward |
| 2017/0258980 A1 | 9/2017 | Katsuki et al. |
| 2017/0274128 A1 | 9/2017 | Tamburino et al. |
| 2017/0317573 A1 | 11/2017 | Mueller et al. |
| 2017/0333607 A1 | 11/2017 | Zarins |
| 2017/0333608 A1 | 11/2017 | Zeng |
| 2017/0340787 A1 | 11/2017 | Corbett et al. |
| 2017/0340788 A1 | 11/2017 | Korakianitis et al. |
| 2017/0340789 A1 | 11/2017 | Bonde et al. |
| 2017/0343043 A1 | 11/2017 | Walsh et al. |
| 2017/0347229 A1 | 11/2017 | Kwon |
| 2017/0348470 A1 | 12/2017 | D'Ambrosio et al. |
| 2017/0354812 A1 | 12/2017 | Callaghan et al. |
| 2018/0015214 A1 | 1/2018 | Lynch |
| 2018/0021494 A1 | 1/2018 | Muller et al. |
| 2018/0021495 A1 | 1/2018 | Muller et al. |
| 2018/0050141 A1 | 2/2018 | Corbett et al. |
| 2018/0055979 A1 | 3/2018 | Corbett et al. |
| 2018/0064860 A1 | 3/2018 | Nunez et al. |
| 2018/0078159 A1 | 3/2018 | Edelman et al. |
| 2018/0093070 A1* | 4/2018 | Cottone ............ A61M 25/0054 |
| 2018/0099076 A1 | 4/2018 | LaRose |
| 2018/0110907 A1 | 4/2018 | Keenan et al. |
| 2018/0110910 A1 | 4/2018 | Rodemerk et al. |
| 2018/0126053 A1 | 5/2018 | Zilbershlag et al. |
| 2018/0133379 A1 | 5/2018 | Farnan et al. |
| 2018/0154058 A1 | 6/2018 | Menon et al. |
| 2018/0169312 A1 | 6/2018 | Barry |
| 2018/0169313 A1 | 6/2018 | Schwammenthal et al. |
| 2018/0199635 A1 | 7/2018 | Longinotti-Buitoni et al. |
| 2018/0207336 A1 | 7/2018 | Solem |
| 2018/0219452 A1 | 8/2018 | Boisclair |
| 2018/0221551 A1 | 8/2018 | Tanner et al. |
| 2018/0221553 A1 | 8/2018 | Taskin |
| 2018/0228950 A1 | 8/2018 | Janeczek et al. |
| 2018/0228953 A1 | 8/2018 | Siess et al. |
| 2018/0243004 A1 | 8/2018 | von Segesser et al. |
| 2018/0243489 A1 | 8/2018 | Haddadi |
| 2018/0250456 A1 | 9/2018 | Nitzan et al. |
| 2018/0250457 A1 | 9/2018 | Morello et al. |
| 2018/0256796 A1 | 9/2018 | Hansen |
| 2018/0256797 A1 | 9/2018 | Schenck et al. |
| 2018/0256800 A1 | 9/2018 | Conyers et al. |
| 2018/0264182 A1 | 9/2018 | Spanier et al. |
| 2018/0280598 A1 | 10/2018 | Curran et al. |
| 2018/0289877 A1 | 10/2018 | Schumacher et al. |
| 2018/0303990 A1 | 10/2018 | Siess et al. |
| 2018/0303991 A1 | 10/2018 | Nüsser et al. |
| 2018/0311421 A1 | 11/2018 | Tuseth |
| 2018/0311423 A1 | 11/2018 | Zeng et al. |
| 2018/0316209 A1 | 11/2018 | Gliner |
| 2018/0318483 A1 | 11/2018 | Dague et al. |
| 2018/0318547 A1 | 11/2018 | Yokoyama |
| 2018/0326131 A1 | 11/2018 | Muller et al. |
| 2018/0326132 A1 | 11/2018 | Maimon et al. |
| 2018/0333059 A1 | 11/2018 | Casas |
| 2018/0335037 A1 | 11/2018 | Shambaugh et al. |
| 2018/0345028 A1 | 12/2018 | Aboud et al. |
| 2018/0353667 A1 | 12/2018 | Moyer et al. |
| 2018/0361042 A1 | 12/2018 | Fitzgerald et al. |
| 2018/0369469 A1 | 12/2018 | Le Duc De Lillers et al. |
| 2019/0001034 A1 | 1/2019 | Taskin et al. |
| 2019/0001038 A1 | 1/2019 | Yomtov et al. |
| 2019/0004037 A1 | 1/2019 | Zhang et al. |
| 2019/0030228 A1 | 1/2019 | Keenan et al. |
| 2019/0046702 A1 | 2/2019 | Siess et al. |
| 2019/0046703 A1 | 2/2019 | Shambaugh et al. |
| 2019/0054223 A1 | 2/2019 | Frazier et al. |
| 2019/0060539 A1 | 2/2019 | Siess et al. |
| 2019/0060543 A1 | 2/2019 | Khanal et al. |
| 2019/0076167 A1 | 3/2019 | Fantuzzi et al. |
| 2019/0083690 A1 | 3/2019 | Siess et al. |
| 2019/0099532 A1 | 4/2019 | Er |
| 2019/0101130 A1 | 4/2019 | Bredenbreuker et al. |
| 2019/0105437 A1 | 4/2019 | Siess et al. |
| 2019/0117865 A1 | 4/2019 | Walters et al. |
| 2019/0125948 A1 | 5/2019 | Stanfield et al. |
| 2019/0143016 A1 | 5/2019 | Corbett et al. |
| 2019/0143018 A1 | 5/2019 | Salahieh et al. |
| 2019/0154053 A1 | 5/2019 | McBride et al. |
| 2019/0167122 A1 | 6/2019 | Obermiller et al. |
| 2019/0167875 A1 | 6/2019 | Simon et al. |
| 2019/0167878 A1 | 6/2019 | Rowe |
| 2019/0170153 A1 | 6/2019 | Scheckel |
| 2019/0175806 A1 | 6/2019 | Tuval et al. |
| 2019/0184078 A1 | 6/2019 | Zilbershlag et al. |
| 2019/0184080 A1 | 6/2019 | Mohl |
| 2019/0192752 A1 | 6/2019 | Tiller et al. |
| 2019/0192753 A1 | 6/2019 | Liu et al. |
| 2019/0199165 A1 | 6/2019 | Carson |
| 2019/0201603 A1 | 7/2019 | Siess et al. |
| 2019/0209755 A1 | 7/2019 | Nix et al. |
| 2019/0209758 A1 | 7/2019 | Tuval et al. |
| 2019/0211836 A1 | 7/2019 | Schumacher et al. |
| 2019/0211846 A1 | 7/2019 | Liebing |
| 2019/0211847 A1 | 7/2019 | Walsh et al. |
| 2019/0216995 A1 | 7/2019 | Kapur et al. |
| 2019/0217002 A1 | 7/2019 | Urakabe |
| 2019/0223877 A1 | 7/2019 | Nitzen et al. |
| 2019/0240680 A1 | 8/2019 | Hayakawa |
| 2019/0254543 A1 | 8/2019 | Hartholt et al. |
| 2019/0269840 A1 | 9/2019 | Tuval et al. |
| 2019/0275224 A1 | 9/2019 | Hanson et al. |
| 2019/0282741 A1* | 9/2019 | Franano ............ A61M 60/816 |
| 2019/0282744 A1 | 9/2019 | D'Ambrosio et al. |
| 2019/0282746 A1 | 9/2019 | Judisch |
| 2019/0290817 A1 | 9/2019 | Guo et al. |
| 2019/0298902 A1 | 10/2019 | Siess et al. |

(56) References Cited

U.S. PATENT DOCUMENTS

| | | |
|---|---|---|
| 2019/0316591 A1 | 10/2019 | Toellner |
| 2019/0321527 A1 | 10/2019 | King et al. |
| 2019/0321529 A1 | 10/2019 | Korakianitis et al. |
| 2019/0321531 A1 | 10/2019 | Cambronne et al. |
| 2019/0336664 A1 | 11/2019 | Liebing |
| 2019/0344000 A1 | 11/2019 | Kushwaha et al. |
| 2019/0344001 A1 | 11/2019 | Salahieh et al. |
| 2019/0351117 A1 | 11/2019 | Cambronne et al. |
| 2019/0351118 A1 | 11/2019 | Graichen et al. |
| 2019/0351119 A1 | 11/2019 | Cambronne et al. |
| 2019/0351120 A1 | 11/2019 | Kushwaha et al. |
| 2019/0358378 A1 | 11/2019 | Schumacher |
| 2019/0358379 A1 | 11/2019 | Wiessler et al. |
| 2019/0358384 A1 | 11/2019 | Epple |
| 2019/0365975 A1 | 12/2019 | Muller et al. |
| 2019/0383298 A1 | 12/2019 | Toellner |
| 2020/0016309 A1 | 1/2020 | Kallenbach et al. |
| 2020/0023109 A1 | 1/2020 | Epple |
| 2020/0028376 A1 | 1/2020 | Ha |
| 2020/0030507 A1 | 1/2020 | Higgins et al. |
| 2020/0030509 A1 | 1/2020 | Siess et al. |
| 2020/0030510 A1 | 1/2020 | Higgins |
| 2020/0030511 A1 | 1/2020 | Higgins |
| 2020/0030512 A1 | 1/2020 | Higgins et al. |
| 2020/0038567 A1 | 2/2020 | Siess et al. |
| 2020/0038568 A1 | 2/2020 | Higgins et al. |
| 2020/0038571 A1 | 2/2020 | Jahangir |
| 2020/0060559 A1 | 2/2020 | Edelman et al. |
| 2020/0069857 A1 | 3/2020 | Schwammenthal et al. |
| 2020/0088207 A1 | 3/2020 | Schumacher et al. |
| 2020/0114053 A1 | 4/2020 | Salahieh et al. |
| 2020/0129684 A1 | 4/2020 | Pfeffer et al. |
| 2020/0139028 A1 | 5/2020 | Scheckel et al. |
| 2020/0139029 A1 | 5/2020 | Scheckel et al. |
| 2020/0147283 A1 | 5/2020 | Tanner et al. |
| 2020/0164125 A1 | 5/2020 | Muller et al. |
| 2020/0164126 A1 | 5/2020 | Muller |
| 2020/0253583 A1 | 8/2020 | Brisken et al. |
| 2020/0261633 A1 | 8/2020 | Spanier |
| 2020/0312450 A1 | 10/2020 | Agnello et al. |
| 2020/0345337 A1 | 11/2020 | Muller et al. |
| 2020/0350812 A1 | 11/2020 | Vogt et al. |
| 2021/0052793 A1 | 2/2021 | Struthers et al. |
| 2021/0236803 A1 | 8/2021 | Stotz |
| 2021/0290087 A1 | 9/2021 | Schlebusch |
| 2021/0290929 A1 | 9/2021 | Stotz |
| 2021/0290930 A1 | 9/2021 | Kasel |
| 2021/0290932 A1 | 9/2021 | Stotz |
| 2021/0290933 A1 | 9/2021 | Stotz |
| 2021/0290937 A1 | 9/2021 | Baumbach |
| 2021/0313869 A1 | 10/2021 | Strasswiemer et al. |
| 2021/0316133 A1 | 10/2021 | Kassel et al. |
| 2021/0322756 A1 | 10/2021 | Vollmer et al. |
| 2021/0330958 A1 | 10/2021 | Stotz et al. |
| 2021/0338999 A1 | 11/2021 | Stotz et al. |
| 2021/0339002 A1 | 11/2021 | Schlebusch et al. |
| 2021/0339004 A1 | 11/2021 | Schlebusch et al. |
| 2021/0339005 A1 | 11/2021 | Stotz et al. |
| 2021/0346674 A1 | 11/2021 | Baumbach et al. |
| 2021/0346675 A1 | 11/2021 | Schlebusch et al. |
| 2021/0346676 A1 | 11/2021 | Schlebusch et al. |
| 2021/0346677 A1 | 11/2021 | Baumbach et al. |
| 2021/0346678 A1 | 11/2021 | Baumbach et al. |
| 2021/0346680 A1 | 11/2021 | Vogt et al. |
| 2021/0378523 A1 | 12/2021 | Budde |
| 2021/0379352 A1 | 12/2021 | Schlebusch et al. |
| 2021/0379355 A1 | 12/2021 | Schuelke et al. |
| 2021/0379358 A1 | 12/2021 | Schuelke et al. |
| 2021/0379359 A1 | 12/2021 | Schellenberg |
| 2021/0379360 A1 | 12/2021 | Schellenberg |
| 2021/0384812 A1 | 12/2021 | Vollmer et al. |
| 2021/0393944 A1 | 12/2021 | Wenning |
| 2022/0008714 A1 | 1/2022 | Stotz |
| 2022/0016411 A1 | 1/2022 | Winterwerber |
| 2022/0032032 A1 | 2/2022 | Schlebusch et al. |
| 2022/0032036 A1 | 2/2022 | Baumbach et al. |
| 2022/0039669 A1 | 2/2022 | Schlebusch et al. |
| 2022/0047173 A1 | 2/2022 | Stotz et al. |
| 2022/0050037 A1 | 2/2022 | Stotz et al. |
| 2022/0072296 A1 | 3/2022 | Mori |
| 2022/0072297 A1 | 3/2022 | Tuval et al. |
| 2022/0072298 A1 | 3/2022 | Spanier et al. |
| 2022/0076807 A1 | 3/2022 | Agnello |
| 2022/0079457 A1 | 3/2022 | Tuval et al. |
| 2022/0080178 A1 | 3/2022 | Salahieh et al. |
| 2022/0080180 A1 | 3/2022 | Siess et al. |
| 2022/0080182 A1 | 3/2022 | Earles et al. |
| 2022/0080183 A1 | 3/2022 | Earles et al. |
| 2022/0080184 A1 | 3/2022 | Clifton et al. |
| 2022/0080185 A1 | 3/2022 | Clifton et al. |
| 2022/0105337 A1 | 4/2022 | Salahieh et al. |
| 2022/0105339 A1 | 4/2022 | Nix et al. |
| 2022/0126083 A1 | 4/2022 | Grauwinkel et al. |
| 2022/0126085 A1 | 4/2022 | Farnan |
| 2022/0126086 A1 | 4/2022 | Schlebusch et al. |
| 2022/0142462 A1 | 5/2022 | Douk et al. |
| 2022/0161018 A1 | 5/2022 | Mitze et al. |
| 2022/0161019 A1 | 5/2022 | Mitze et al. |
| 2022/0161021 A1 | 5/2022 | Mitze et al. |
| 2022/0241580 A1 | 8/2022 | Stotz et al. |
| 2022/0249829 A1 | 8/2022 | Edwards et al. |
| 2022/0323742 A1 | 10/2022 | Grauwinkel et al. |
| 2022/0361762 A1 | 11/2022 | Lalancette |
| 2022/0407403 A1 | 12/2022 | Vogt et al. |
| 2023/0001178 A1 | 1/2023 | Corbett et al. |
| 2023/0063798 A1 | 3/2023 | Edwards et al. |
| 2023/0079625 A1 | 3/2023 | Theran et al. |
| 2023/0105131 A1 | 4/2023 | Kerkhoffs et al. |
| 2023/0125439 A1 | 4/2023 | Malone et al. |
| 2023/0128328 A1 | 4/2023 | Malone et al. |
| 2023/0130285 A1 | 4/2023 | Malone et al. |
| 2023/0149691 A1 | 5/2023 | VanCamp et al. |
| 2023/0149692 A1 | 5/2023 | Larsen et al. |
| 2023/0158289 A1 | 5/2023 | Breidall et al. |
| 2023/0173250 A1 | 6/2023 | Stigloher |
| 2023/0191141 A1 | 6/2023 | Wenning et al. |
| 2023/0233834 A1 | 7/2023 | Alexander et al. |
| 2023/0277833 A1 | 9/2023 | Sharma et al. |
| 2023/0277836 A1 | 9/2023 | Schellenberg et al. |
| 2023/0293878 A1 | 9/2023 | Christof et al. |
| 2023/0364411 A1 | 11/2023 | Bette |
| 2023/0381492 A1 | 11/2023 | Alexander et al. |
| 2024/0011808 A1 | 1/2024 | Winzer et al. |
| 2024/0074828 A1 | 3/2024 | Wenning |
| 2024/0075277 A1 | 3/2024 | Schellenberg |
| 2024/0102475 A1 | 3/2024 | Schuelke et al. |
| 2024/0198084 A1 | 6/2024 | Stotz |
| 2024/0245902 A1 | 7/2024 | Schlebusch et al. |
| 2024/0269459 A1 | 8/2024 | Schellenberg et al. |
| 2024/0277998 A1 | 8/2024 | Vogt et al. |
| 2024/0285935 A1 | 8/2024 | Popov et al. |
| 2024/0335651 A1 | 10/2024 | Mitze et al. |
| 2024/0399135 A1 | 12/2024 | Stotz et al. |
| 2025/0032773 A1 | 1/2025 | Baumbach et al. |
| 2025/0121177 A1 | 4/2025 | West |
| 2025/0143587 A1 | 5/2025 | Stotz |
| 2025/0144397 A1 | 5/2025 | Kassel et al. |
| 2025/0161660 A1 | 5/2025 | Baumbach et al. |
| 2025/0170388 A1 | 5/2025 | Kerkhoffs et al. |
| 2025/0222247 A1 | 7/2025 | Schlebusch |
| 2025/0235687 A1 | 7/2025 | Schlebusch et al. |
| 2025/0251330 A1 | 8/2025 | Stotz |
| 2025/0281060 A1 | 9/2025 | Schlebusch et al. |
| 2025/0319299 A1 | 10/2025 | Stotz et al. |
| 2025/0339669 A1 | 11/2025 | Stotz et al. |
| 2025/0345590 A1 | 11/2025 | Schlebusch et al. |
| 2025/0367431 A1 | 12/2025 | Baumbach et al. |

FOREIGN PATENT DOCUMENTS

| | | |
|---|---|---|
| AU | 2012261669 | 1/2013 |
| AU | 2013203301 | 5/2013 |
| AU | 2013273663 | 1/2014 |
| BR | PI0904483-3 | 7/2011 |

(56) References Cited

FOREIGN PATENT DOCUMENTS

| CA | 2 026 692 | 4/1992 |
|---|---|---|
| CA | 2 026 693 | 4/1992 |
| CA | 2 292 432 | 5/1998 |
| CA | 2 664 835 | 2/2008 |
| CA | 2 796 357 | 10/2011 |
| CA | 3 122 415 | 7/2020 |
| CA | 2 947 984 | 11/2022 |
| CN | 1192351 A | 9/1998 |
| CN | 1222862 A | 7/1999 |
| CN | 1254598 A | 5/2000 |
| CN | 1376523 A | 10/2002 |
| CN | 2535055 | 2/2003 |
| CN | 1118304 C | 8/2003 |
| CN | 2616217 | 5/2004 |
| CN | 1202871 C | 5/2005 |
| CN | 1661338 A | 8/2005 |
| CN | 1833736 A | 9/2006 |
| CN | 200977306 | 11/2007 |
| CN | 101112628 | 1/2008 |
| CN | 101128168 | 2/2008 |
| CN | 101208045 | 6/2008 |
| CN | 101214158 | 7/2008 |
| CN | 201150675 | 11/2008 |
| CN | 101351237 | 1/2009 |
| CN | 101448535 | 6/2009 |
| CN | 101460094 | 6/2009 |
| CN | 101579233 | 11/2009 |
| CN | 101677812 | 3/2010 |
| CN | 201437016 | 4/2010 |
| CN | 101711683 | 5/2010 |
| CN | 201618200 | 11/2010 |
| CN | 201658687 | 12/2010 |
| CN | 201710717 | 1/2011 |
| CN | 201894758 | 7/2011 |
| CN | 102421372 | 4/2012 |
| CN | 102475923 | 5/2012 |
| CN | 102545538 | 7/2012 |
| CN | 202314596 | 7/2012 |
| CN | 102743801 | 10/2012 |
| CN | 102803923 | 11/2012 |
| CN | 103143072 | 6/2013 |
| CN | 103328018 | 9/2013 |
| CN | 103845766 | 6/2014 |
| CN | 103857326 | 6/2014 |
| CN | 103861162 | 6/2014 |
| CN | 103915980 | 7/2014 |
| CN | 103957957 | 7/2014 |
| CN | 203809157 | 9/2014 |
| CN | 203842087 | 9/2014 |
| CN | 104105449 | 10/2014 |
| CN | 104188687 | 12/2014 |
| CN | 104208763 | 12/2014 |
| CN | 104208764 | 12/2014 |
| CN | 203971004 | 12/2014 |
| CN | 104274873 | 1/2015 |
| CN | 204106671 | 1/2015 |
| CN | 204219479 | 3/2015 |
| CN | 103877630 | 2/2016 |
| CN | 205215814 | 5/2016 |
| CN | 103977464 | 8/2016 |
| CN | 104162192 | 9/2016 |
| CN | 106104229 | 11/2016 |
| CN | 106333707 | 1/2017 |
| CN | 104888293 | 3/2017 |
| CN | 106512117 | 3/2017 |
| CN | 206007680 | 3/2017 |
| CN | 104225696 | 6/2017 |
| CN | 107019824 | 8/2017 |
| CN | 206443963 | 8/2017 |
| CN | 107281567 | 10/2017 |
| CN | 104707194 | 11/2017 |
| CN | 107530479 | 1/2018 |
| CN | 107632167 | 1/2018 |
| CN | 107921187 | 4/2018 |
| CN | 105498002 | 6/2018 |
| CN | 106310410 | 7/2018 |
| CN | 109939282 | 6/2019 |
| CN | 106902404 | 8/2019 |
| CN | 209790495 | 12/2019 |
| CN | 110665079 | 1/2020 |
| CN | 210020563 | 2/2020 |
| CN | 111166948 | 5/2020 |
| CN | 111166949 | 5/2020 |
| CN | 215841206 | 2/2022 |
| CN | 217828630 | 11/2022 |
| CN | 218922664 | 4/2023 |
| CN | 116077106 | 5/2023 |
| CN | 116365757 | 6/2023 |
| CN | 219250364 | 6/2023 |
| CN | 116785582 | 9/2023 |
| CN | 116531654 | 11/2023 |
| CN | 116440404 | 3/2024 |
| CN | 117018427 | 3/2024 |
| CN | 117482377 | 4/2024 |
| CN | 118320293 | 7/2024 |
| CN | 118320294 | 7/2024 |
| CN | 113769260 | 9/2024 |
| CN | 118142074 | 9/2024 |
| CN | 118681125 | 9/2024 |
| CN | 118899971 | 11/2024 |
| CN | 118920928 | 11/2024 |
| DE | 1 001 642 | 1/1957 |
| DE | 1 165 144 | 3/1964 |
| DE | 27 07 951 | 9/1977 |
| DE | 26 24 058 | 12/1977 |
| DE | 3 545 214 | 7/1986 |
| DE | 41 05 278 | 8/1992 |
| DE | 195 20 920 | 12/1995 |
| DE | 195 46 336 | 5/1997 |
| DE | 695 01 834 | 10/1998 |
| DE | 198 54 724 | 5/1999 |
| DE | 198 21 307 | 10/1999 |
| DE | 199 10 872 | 10/1999 |
| DE | 199 56 380 | 11/1999 |
| DE | 100 59 714 | 5/2002 |
| DE | 100 60 275 | 6/2002 |
| DE | 101 44 269 | 3/2003 |
| DE | 102 26 305 | 10/2003 |
| DE | 103 45 694 | 4/2005 |
| DE | 697 31 709 | 4/2005 |
| DE | 101 55 011 | 11/2005 |
| DE | 601 19 592 | 9/2006 |
| DE | 11 2004 001 809 | 11/2006 |
| DE | 20 2005 020 288 | 6/2007 |
| DE | 10 2006 001 180 | 9/2007 |
| DE | 10 2006 019 206 | 10/2007 |
| DE | 10 2006 036 948 | 2/2008 |
| DE | 10 2008 060 357 | 6/2010 |
| DE | 10 2009 007 216 | 8/2010 |
| DE | 10 2009 011 726 | 9/2010 |
| DE | 10 2009 025 464 | 1/2011 |
| DE | 10 2009 039 658 | 3/2011 |
| DE | 10 2009 047 845 | 3/2011 |
| DE | 20 2009 018 416 | 8/2011 |
| DE | 10 2010 041 995 | 4/2012 |
| DE | 10 2011 106 142 | 12/2012 |
| DE | 20 2011 110 389 | 9/2013 |
| DE | 10 2012 022 456 | 5/2014 |
| DE | 10 2013 007 562 | 11/2014 |
| DE | 10 2015 004 177 | 10/2015 |
| DE | 10 2014 210 299 | 12/2015 |
| DE | 10 2014 212 323 | 12/2015 |
| DE | 11 2014 001 418 | 12/2015 |
| DE | 10 2014 224 151 | 6/2016 |
| DE | 10 2015 216 050 | 2/2017 |
| DE | 10 2015 219 263 | 4/2017 |
| DE | 10 2015 222 199 | 5/2017 |
| DE | 20 2015 009 422 | 7/2017 |
| DE | 10 2012 207 042 | 9/2017 |
| DE | 10 2016 013 334 | 4/2018 |
| DE | 10 2017 209 917 | 12/2018 |
| DE | 10 2017 212 193 | 1/2019 |
| DE | 10 2018 207 564 | 11/2019 |
| DE | 10 2018 207 578 | 11/2019 |

(56) References Cited

FOREIGN PATENT DOCUMENTS

| | | |
|---|---|---|
| DE | 10 2018 207 585 | 11/2019 |
| DE | 10 2018 207 591 | 11/2019 |
| DE | 10 2018 207 594 | 11/2019 |
| DE | 10 2018 207 611 | 11/2019 |
| DE | 10 2018 207 622 | 11/2019 |
| DE | 10 2018 208 536 | 12/2019 |
| DE | 10 2018 208 540 | 12/2019 |
| DE | 10 2018 208 541 | 12/2019 |
| DE | 10 2018 208 550 | 12/2019 |
| DE | 10 2018 208 862 | 12/2019 |
| DE | 10 2018 208 916 | 12/2019 |
| DE | 10 2018 208 927 | 12/2019 |
| DE | 10 2018 208 945 | 12/2019 |
| DE | 10 2018 210 076 | 12/2019 |
| DE | 10 2018 207 624 | 1/2020 |
| DE | 10 2018 211 327 | 1/2020 |
| DE | 10 2018 211 328 | 1/2020 |
| DE | 10 2018 212 153 | 1/2020 |
| DE | 10 2018 213 151 | 2/2020 |
| DE | 10 2018 213 350 | 2/2020 |
| DE | 10 2018 220 658 | 6/2020 |
| DE | 10 2018 222 505 | 6/2020 |
| DE | 10 2020 102 473 | 8/2021 |
| DE | 11 2020 003 063 | 3/2022 |
| DE | 11 2020 003 151 | 3/2022 |
| DE | 11 2020 004 148 | 6/2022 |
| EP | 0 050 814 | 5/1982 |
| EP | 0 629 412 | 12/1994 |
| EP | 0 764 448 | 3/1997 |
| EP | 0 794 411 | 9/1997 |
| EP | 0 855 515 | 7/1998 |
| EP | 0 890 179 | 1/1999 |
| EP | 0 916 359 | 5/1999 |
| EP | 1 013 294 | 6/2000 |
| EP | 1 062 959 | 12/2000 |
| EP | 1 339 443 | 11/2001 |
| EP | 1 186 873 | 3/2002 |
| EP | 1 011 803 | 9/2004 |
| EP | 1 475 880 | 11/2004 |
| EP | 1 169 072 | 5/2005 |
| EP | 1 176 999 | 7/2005 |
| EP | 1 354 606 | 6/2006 |
| EP | 1 801 420 | 6/2007 |
| EP | 2 009 233 | 12/2008 |
| EP | 2 098 746 | 9/2009 |
| EP | 2 143 385 | 1/2010 |
| EP | 2 175 770 | 4/2010 |
| EP | 2 047 872 | 9/2010 |
| EP | 2 403 109 | 1/2012 |
| EP | 2 187 807 | 6/2012 |
| EP | 2 330 724 | 8/2012 |
| EP | 2 570 143 | 3/2013 |
| EP | 2 401 003 | 10/2013 |
| EP | 3 326 567 | 10/2014 |
| EP | 1 871 441 | 11/2014 |
| EP | 1 898 971 | 3/2015 |
| EP | 2 859 911 | 4/2015 |
| EP | 2 519 273 | 8/2015 |
| EP | 2 217 302 | 9/2015 |
| EP | 2 438 936 | 10/2015 |
| EP | 2 438 937 | 10/2015 |
| EP | 2 960 515 | 12/2015 |
| EP | 2 968 718 | 1/2016 |
| EP | 1 996 252 | 5/2016 |
| EP | 2 475 415 | 6/2016 |
| EP | 2 906 265 | 7/2016 |
| EP | 2 213 227 | 8/2016 |
| EP | 2 835 141 | 8/2016 |
| EP | 3 069 739 | 9/2016 |
| EP | 3 088 016 | 11/2016 |
| EP | 1 931 403 | 1/2017 |
| EP | 3 127 562 | 2/2017 |
| EP | 2 585 129 | 3/2017 |
| EP | 2 646 068 | 3/2017 |
| EP | 3 187 210 | 7/2017 |
| EP | 3 222 301 | 9/2017 |
| EP | 3 222 302 | 9/2017 |
| EP | 2 945 661 | 11/2017 |
| EP | 2 136 861 | 12/2017 |
| EP | 3 020 426 | 12/2017 |
| EP | 3 038 669 | 1/2018 |
| EP | 3 062 730 | 1/2018 |
| EP | 3 180 050 | 2/2018 |
| EP | 3 287 154 | 2/2018 |
| EP | 1 789 129 | 6/2018 |
| EP | 2 366 412 | 8/2018 |
| EP | 3 205 359 | 8/2018 |
| EP | 3 205 360 | 8/2018 |
| EP | 3 378 421 | 9/2018 |
| EP | 3 131 599 | 2/2019 |
| EP | 3 456 367 | 3/2019 |
| EP | 3 119 451 | 6/2019 |
| EP | 3 389 738 | 8/2019 |
| EP | 3 536 360 | 9/2019 |
| EP | 3 542 835 | 9/2019 |
| EP | 3 542 836 | 9/2019 |
| EP | 2 505 090 | 12/2019 |
| EP | 3 062 877 | 12/2019 |
| EP | 3 189 862 | 2/2020 |
| EP | 3 668 560 | 6/2020 |
| EP | 3 711 785 | 9/2020 |
| EP | 3 711 786 | 9/2020 |
| EP | 3 711 787 | 9/2020 |
| EP | 3 720 520 | 10/2020 |
| EP | 3 069 738 | 12/2020 |
| EP | 3 069 740 | 12/2020 |
| EP | 3 131 597 | 12/2020 |
| EP | 3 142 722 | 12/2020 |
| EP | 3 579 894 | 12/2020 |
| EP | 3 753 594 | 12/2020 |
| EP | 3 188 769 | 1/2021 |
| EP | 3 357 523 | 1/2021 |
| EP | 3 490 122 | 1/2021 |
| EP | 2 869 866 | 2/2021 |
| EP | 3 398 626 | 2/2021 |
| EP | 3 487 549 | 2/2021 |
| EP | 3 490 628 | 2/2021 |
| EP | 3 113 806 | 3/2021 |
| EP | 3 487 548 | 3/2021 |
| EP | 3 509 661 | 3/2021 |
| EP | 3 515 523 | 3/2021 |
| EP | 3 528 863 | 3/2021 |
| EP | 3 615 103 | 3/2021 |
| EP | 3 794 720 | 3/2021 |
| EP | 4 271 461 | 3/2021 |
| EP | 2 344 218 | 4/2021 |
| EP | 3 436 104 | 4/2021 |
| EP | 3 749 383 | 4/2021 |
| EP | 3 808 404 | 4/2021 |
| EP | 3 821 938 | 5/2021 |
| EP | 3 131 600 | 6/2021 |
| EP | 3 131 615 | 6/2021 |
| EP | 3 338 825 | 6/2021 |
| EP | 3 432 944 | 6/2021 |
| EP | 3 684 439 | 7/2021 |
| EP | 2 582 414 | 8/2021 |
| EP | 3 407 930 | 8/2021 |
| EP | 3 782 665 | 8/2021 |
| EP | 3 782 666 | 8/2021 |
| EP | 3 782 668 | 8/2021 |
| EP | 3 858 397 | 8/2021 |
| EP | 3 216 467 | 9/2021 |
| EP | 3 463 505 | 9/2021 |
| EP | 3 884 968 | 9/2021 |
| EP | 3 884 969 | 9/2021 |
| EP | 3 884 970 | 9/2021 |
| EP | 2 599 510 | 10/2021 |
| EP | 3 003 421 | 10/2021 |
| EP | 3 027 241 | 10/2021 |
| EP | 3 668 561 | 10/2021 |
| EP | 3 579 904 | 11/2021 |
| EP | 2 628 493 | 12/2021 |
| EP | 3 164 168 | 12/2021 |
| EP | 3 344 129 | 12/2021 |

(56) References Cited

FOREIGN PATENT DOCUMENTS

| | | |
|----|-----------|---------|
| EP | 3 914 330 | 12/2021 |
| EP | 3 928 825 | 12/2021 |
| EP | 3 556 409 | 1/2022  |
| EP | 3 624 868 | 1/2022  |
| EP | 3 955 985 | 2/2022  |
| EP | 3 624 867 | 3/2022  |
| EP | 3 651 822 | 3/2022  |
| EP | 3 689 389 | 3/2022  |
| EP | 3 697 464 | 3/2022  |
| EP | 3 737 436 | 3/2022  |
| EP | 3 972 661 | 3/2022  |
| EP | 2 967 630 | 4/2022  |
| EP | 3 142 721 | 4/2022  |
| EP | 3 520 834 | 4/2022  |
| EP | 3 586 887 | 4/2022  |
| EP | 3 638 336 | 4/2022  |
| EP | 3 689 388 | 4/2022  |
| EP | 3 765 110 | 4/2022  |
| EP | 3 782 667 | 4/2022  |
| EP | 3 829 673 | 4/2022  |
| EP | 3 976 129 | 4/2022  |
| EP | 3 984 589 | 4/2022  |
| EP | 3 986 528 | 4/2022  |
| EP | 3 649 926 | 5/2022  |
| EP | 3 653 113 | 5/2022  |
| EP | 3 654 006 | 5/2022  |
| EP | 3 735 280 | 5/2022  |
| EP | 3 897 814 | 5/2022  |
| EP | 3 990 047 | 5/2022  |
| EP | 3 219 339 | 6/2022  |
| EP | 3 737 310 | 7/2022  |
| EP | 2 999 400 | 8/2022  |
| EP | 3 711 788 | 8/2022  |
| EP | 3 899 994 | 8/2022  |
| EP | 4 039 320 | 8/2022  |
| EP | 3 487 550 | 9/2022  |
| EP | 3 606 575 | 9/2022  |
| EP | 3 694 573 | 9/2022  |
| EP | 3 834 876 | 9/2022  |
| EP | 3 000 492 | 10/2022 |
| EP | 3 600 477 | 10/2022 |
| EP | 3 897 768 | 10/2022 |
| EP | 3 914 310 | 10/2022 |
| EP | 3 914 311 | 10/2022 |
| EP | 3 000 493 | 11/2022 |
| EP | 3 858 422 | 11/2022 |
| EP | 3 866 876 | 11/2022 |
| EP | 3 941 546 | 11/2022 |
| EP | 2 892 583 | 1/2023  |
| EP | 3 370 797 | 1/2023  |
| EP | 3 393 542 | 1/2023  |
| EP | 3 597 231 | 1/2023  |
| EP | 3 656 292 | 1/2023  |
| EP | 3 668 562 | 1/2023  |
| EP | 3 768 345 | 1/2023  |
| EP | 3 856 275 | 1/2023  |
| EP | 2 868 332 | 2/2023  |
| EP | 3 003 420 | 2/2023  |
| EP | 3 397 299 | 2/2023  |
| EP | 3 539 585 | 2/2023  |
| EP | 3 956 010 | 2/2023  |
| EP | 4 137 193 | 2/2023  |
| EP | 3 046 594 | 3/2023  |
| EP | 3 127 563 | 3/2023  |
| EP | 3 256 186 | 3/2023  |
| EP | 3 288 609 | 3/2023  |
| EP | 3 538 173 | 3/2023  |
| EP | 3 606 576 | 3/2023  |
| EP | 3 927 390 | 3/2023  |
| EP | 3 384 940 | 4/2023  |
| EP | 3 441 616 | 4/2023  |
| EP | 3 938 005 | 4/2023  |
| EP | 3 946 511 | 4/2023  |
| EP | 3 685 562 | 5/2023  |
| EP | 3 544 649 | 6/2023  |
| EP | 3 634 528 | 6/2023  |
| EP | 3 397 298 | 7/2023  |
| EP | 3 809 959 | 7/2023  |
| EP | 3 912 673 | 7/2023  |
| EP | 4 218 897 | 8/2023  |
| EP | 4 218 898 | 8/2023  |
| EP | 4 218 899 | 8/2023  |
| EP | 2 072 150 | 9/2023  |
| EP | 2 961 984 | 9/2023  |
| EP | 3 352 808 | 9/2023  |
| EP | 3 768 156 | 9/2023  |
| EP | 3 554 576 | 10/2023 |
| EP | 3 615 102 | 10/2023 |
| EP | 3 737 435 | 10/2023 |
| EP | 3 795 208 | 10/2023 |
| EP | 4 052 754 | 10/2023 |
| EP | 4 149 606 | 10/2023 |
| EP | 3 157 596 | 11/2023 |
| EP | 3 515 525 | 11/2023 |
| EP | 3 621 669 | 11/2023 |
| EP | 3 744 362 | 11/2023 |
| EP | 3 766 428 | 11/2023 |
| EP | 3 781 027 | 11/2023 |
| EP | 3 808 390 | 11/2023 |
| EP | 4 061 470 | 11/2023 |
| EP | 4 070 720 | 11/2023 |
| EP | 3 449 958 | 12/2023 |
| EP | 3 687 596 | 12/2023 |
| EP | 3 710 076 | 12/2023 |
| EP | 3 768 340 | 12/2023 |
| EP | 3 787 707 | 12/2023 |
| EP | 3 926 194 | 12/2023 |
| EP | 3 784 305 | 1/2024  |
| EP | 3 801 675 | 1/2024  |
| EP | 3 925 659 | 1/2024  |
| EP | 4 115 919 | 1/2024  |
| EP | 3 566 636 | 2/2024  |
| EP | 3 634 526 | 2/2024  |
| EP | 3 768 342 | 2/2024  |
| EP | 3 768 347 | 2/2024  |
| EP | 3 769 799 | 2/2024  |
| EP | 3 790 606 | 2/2024  |
| EP | 3 930 780 | 2/2024  |
| EP | 3 397 147 | 3/2024  |
| EP | 3 782 695 | 3/2024  |
| EP | 3 854 448 | 3/2024  |
| EP | 4 140 532 | 5/2024  |
| EP | 3 693 038 | 6/2024  |
| EP | 3 768 344 | 7/2024  |
| EP | 3 970 765 | 7/2024  |
| EP | 4 419 042 | 8/2024  |
| EP | 3 854 444 | 9/2024  |
| EP | 4 384 259 | 9/2024  |
| EP | 4 429 750 | 9/2024  |
| EP | 3 534 985 | 10/2024 |
| EP | 3 793 674 | 10/2024 |
| EP | 3 893 957 | 10/2024 |
| EP | 3 914 334 | 10/2024 |
| EP | 3 618 885 | 11/2024 |
| EP | 4 034 221 | 11/2024 |
| EP | 4 087 641 | 11/2024 |
| EP | 3 809 960 | 12/2024 |
| EP | 4 039 289 | 12/2024 |
| EP | 4 084 856 | 1/2025  |
| EP | 3 522 947 | 2/2025  |
| EP | 3 854 446 | 2/2025  |
| EP | 4 429 754 | 2/2025  |
| EP | 3 970 785 | 3/2025  |
| EP | 3 998 102 | 3/2025  |
| EP | 4 429 751 | 3/2025  |
| EP | 4 429 752 | 3/2025  |
| EP | 4 429 753 | 3/2025  |
| EP | 4 023 282 | 4/2025  |
| EP | 3 950 043 | 5/2025  |
| EP | 3 955 986 | 5/2025  |
| EP | 3 958 921 | 5/2025  |
| EP | 4 218 900 | 5/2025  |
| EP | 4 429 755 | 5/2025  |
| EP | 2 830 675 | 6/2025  |

(56)                References Cited

FOREIGN PATENT DOCUMENTS

| | | |
|---|---|---|
| EP | 3 899 964 | 6/2025 |
| EP | 3 948 888 | 6/2025 |
| EP | 3 965 845 | 6/2025 |
| EP | 4 039 319 | 6/2025 |
| EP | 3 668 558 | 7/2025 |
| EP | 3 780 041 | 7/2025 |
| EP | 4 095 872 | 7/2025 |
| EP | 4 297 672 | 7/2025 |
| EP | 3 668 559 | 8/2025 |
| EP | 3 746 149 | 8/2025 |
| EP | 3 823 687 | 8/2025 |
| EP | 3 848 088 | 8/2025 |
| EP | 4 119 184 | 9/2025 |
| EP | 4 218 556 | 9/2025 |
| EP | 4 046 678 | 10/2025 |
| ES | 2 913 485 | 6/2022 |
| FR | 1458525 | 3/1966 |
| FR | 2 768 056 | 3/1999 |
| GB | 0 648 739 | 1/1951 |
| GB | 2 213 541 | 8/1989 |
| GB | 2 345 387 | 7/2000 |
| GB | 2 451 161 | 12/2011 |
| GB | 2 504 177 | 1/2014 |
| GB | 2 545 062 | 6/2017 |
| GB | 2 545 750 | 6/2017 |
| JP | S59-080229 | 5/1984 |
| JP | 59-119788 | 8/1984 |
| JP | S61-500059 | 1/1986 |
| JP | S61-125329 | 6/1986 |
| JP | S62-113555 | 7/1987 |
| JP | S62-204733 | 9/1987 |
| JP | S62-282284 | 12/1987 |
| JP | S64-68236 | 3/1989 |
| JP | H02-055886 | 2/1990 |
| JP | 2-79738 | 3/1990 |
| JP | H02-234750 | 9/1990 |
| JP | H04-176471 | 6/1992 |
| JP | H04-108384 | 9/1992 |
| JP | H05-079875 | 3/1993 |
| JP | H06-218044 | 8/1994 |
| JP | H07-047025 | 5/1995 |
| JP | H08-057042 | 3/1996 |
| JP | H08-066398 | 3/1996 |
| JP | H08-504621 | 5/1996 |
| JP | H08-327527 | 12/1996 |
| JP | H10-052489 | 2/1998 |
| JP | H10-505766 | 6/1998 |
| JP | 2888609 | 5/1999 |
| JP | 2889384 | 5/1999 |
| JP | H11-239617 | 9/1999 |
| JP | 2000-512191 | 9/2000 |
| JP | 2001-037728 | 2/2001 |
| JP | 2001037728 A  * | 2/2001 |
| JP | 2001-506140 | 5/2001 |
| JP | 2001-515374 | 9/2001 |
| JP | 2001-515375 | 9/2001 |
| JP | 2001-276213 | 10/2001 |
| JP | 2002-525175 | 8/2002 |
| JP | 2003-019197 | 1/2003 |
| JP | 2003-047656 | 2/2003 |
| JP | 2003-062065 | 3/2003 |
| JP | 2003-525438 | 8/2003 |
| JP | 2003-528697 | 9/2003 |
| JP | 2004-019468 | 1/2004 |
| JP | 2004-515278 | 5/2004 |
| JP | 2004-278375 | 10/2004 |
| JP | 2005-028137 | 2/2005 |
| JP | 2005-507039 | 3/2005 |
| JP | 2005-192687 | 7/2005 |
| JP | 2006-528006 | 12/2006 |
| JP | 2007-222644 | 9/2007 |
| JP | 2008-511414 | 4/2008 |
| JP | 2008-516654 | 5/2008 |
| JP | 2006-518249 | 8/2008 |
| JP | 2008-178690 | 8/2008 |

| | | | |
|---|---|---|---|
| JP | 2009-504290 | | 2/2009 |
| JP | 2009-240348 | | 10/2009 |
| JP | 2010-503495 | | 2/2010 |
| JP | 2010-518907 | | 6/2010 |
| JP | 2010-258181 | | 11/2010 |
| JP | 2010-534080 | | 11/2010 |
| JP | 2012-520157 | | 9/2012 |
| JP | 2013-013216 | | 1/2013 |
| JP | 2013-519497 | | 5/2013 |
| JP | 2013-128792 | | 7/2013 |
| JP | 2014-004303 | | 1/2014 |
| JP | 2014-524274 | | 9/2014 |
| JP | 2015-514529 | | 5/2015 |
| JP | 2015-514531 | | 5/2015 |
| JP | 2015-515429 | | 5/2015 |
| JP | 2015-122448 | | 7/2015 |
| JP | 2015-527172 | | 9/2015 |
| JP | 2015-181800 | | 10/2015 |
| JP | 2016-002466 | | 1/2016 |
| JP | 2016-509950 | | 4/2016 |
| JP | 2016-532500 | | 10/2016 |
| JP | 2017-500932 | | 1/2017 |
| JP | 6063151 | | 1/2017 |
| JP | 2017-176719 | | 10/2017 |
| JP | 2017-532084 | | 11/2017 |
| JP | 6267625 | | 1/2018 |
| JP | 2018-057878 | | 4/2018 |
| JP | 2019-508128 | | 3/2019 |
| JP | 2019-516458 | | 6/2019 |
| JP | 2019-523110 | | 8/2019 |
| JP | 6572056 | | 9/2019 |
| JP | 2020-072985 | | 5/2020 |
| JP | 2020-523090 | | 8/2020 |
| JP | 2018-510708 | | 3/2021 |
| JP | 2019-509141 | | 2/2022 |
| KR | 10-2011-0098192 | | 9/2011 |
| RO | 131676 | | 2/2017 |
| RU | 2 051 695 | | 1/1996 |
| TW | 374317 | | 11/1999 |
| UA | 97202 | C2 | 1/2012 |
| WO | WO 89/006513 | | 1/1989 |
| WO | WO 92/015239 | | 9/1992 |
| WO | WO 94/009835 | | 5/1994 |
| WO | WO 97/037696 | | 10/1997 |
| WO | WO 97/039785 | | 10/1997 |
| WO | WO 98/043688 | | 10/1998 |
| WO | WO 99/049912 | | 10/1999 |
| WO | WO 00/033047 | | 6/2000 |
| WO | WO 00/033446 | | 6/2000 |
| WO | WO 02/022200 | | 3/2002 |
| WO | WO 02/041935 | | 5/2002 |
| WO | WO 02/070039 | | 9/2002 |
| WO | WO 03/075981 | | 9/2003 |
| WO | WO 03/103745 | | 12/2003 |
| WO | WO 2005/020848 | | 3/2005 |
| WO | WO 2005/028014 | | 3/2005 |
| WO | WO 2005/037345 | | 4/2005 |
| WO | WO 2006/122001 | | 11/2006 |
| WO | WO 2007/033933 | | 3/2007 |
| WO | WO 2007/105842 | | 9/2007 |
| WO | WO 2008/017289 | | 2/2008 |
| WO | WO 2008/081783 | | 7/2008 |
| WO | WO 2009/010888 | | 1/2009 |
| WO | WO 2009/046789 | | 4/2009 |
| WO | WO 2009/046790 | | 4/2009 |
| WO | WO 2009/073037 | | 6/2009 |
| WO | WO 2010/119267 | | 10/2010 |
| WO | WO 2010/142286 | | 12/2010 |
| WO | WO 2010/143272 | | 12/2010 |
| WO | WO 2011/003043 | | 1/2011 |
| WO | WO 2011/081626 | | 7/2011 |
| WO | WO 2011/160858 | | 12/2011 |
| WO | WO 2012/018917 | * | 2/2012 |
| WO | WO 2012/047540 | | 4/2012 |
| WO | WO 2012/112129 | | 8/2012 |
| WO | WO 2012/112378 | | 8/2012 |
| WO | WO 2013/037380 | | 3/2013 |
| WO | WO 2013/120957 | | 8/2013 |
| WO | WO 2013/160443 | | 10/2013 |

(56) References Cited

FOREIGN PATENT DOCUMENTS

| | | |
|---|---|---|
| WO | WO 2013/167432 | 11/2013 |
| WO | WO 2013/173239 | 11/2013 |
| WO | WO 2014/042925 | 3/2014 |
| WO | WO 2014/141284 | 9/2014 |
| WO | WO 2014/165635 | 10/2014 |
| WO | WO 2015/039605 | 3/2015 |
| WO | WO 2015/063281 | 5/2015 |
| WO | WO 2015/085076 | 6/2015 |
| WO | WO 2015/085220 | 6/2015 |
| WO | WO 2015/109028 | 7/2015 |
| WO | WO 2015/172173 | 11/2015 |
| WO | WO 2015/175718 | 11/2015 |
| WO | WO 2016/001284 | 1/2016 |
| WO | WO 2016/028644 | 2/2016 |
| WO | WO 2016/066180 | 5/2016 |
| WO | WO 2016/137743 | 9/2016 |
| WO | WO 2016/146661 | 9/2016 |
| WO | WO 2016/146663 | 9/2016 |
| WO | WO 2017/004175 | 1/2017 |
| WO | WO 2017/015764 | 2/2017 |
| WO | WO 2017/021465 | 2/2017 |
| WO | WO 2017/032751 | 3/2017 |
| WO | WO 2017/053988 | 3/2017 |
| WO | WO 2017/060257 | 4/2017 |
| WO | WO 2017/066257 | 4/2017 |
| WO | WO 2017/106190 | 6/2017 |
| WO | WO 2017/112695 | 6/2017 |
| WO | WO 2017/112698 | 6/2017 |
| WO | WO 2017/147291 | 8/2017 |
| WO | WO 2017/159849 | 9/2017 |
| WO | WO 2017/162619 | 9/2017 |
| WO | WO 2017/205909 | 12/2017 |
| WO | WO 2017/214118 | 12/2017 |
| WO | WO 2018/005228 | 1/2018 |
| WO | WO 2018/007120 | 1/2018 |
| WO | WO 2018/036927 | 3/2018 |
| WO | WO 2018/039479 | 3/2018 |
| WO | WO 2018/048800 | 3/2018 |
| WO | WO 2018/088939 | 3/2018 |
| WO | WO 2018/081040 | 5/2018 |
| WO | WO 2018/089970 | 5/2018 |
| WO | WO 2018/109038 | 6/2018 |
| WO | WO 2018/139508 | 8/2018 |
| WO | WO 2018/197306 | 11/2018 |
| WO | WO 2018/213089 | 11/2018 |
| WO | WO 2019/013794 | 1/2019 |
| WO | WO 2019/034670 | 2/2019 |
| WO | WO 2019/034775 | 2/2019 |
| WO | WO 2019/035804 | 2/2019 |
| WO | WO 2019/038343 | 2/2019 |
| WO | WO 2019/057636 | 3/2019 |
| WO | WO 2019/067233 | 4/2019 |
| WO | WO 2019/078723 | 4/2019 |
| WO | WO 2019/126721 | 6/2019 |
| WO | WO 2019/135767 | 7/2019 |
| WO | WO 2019/137911 | 7/2019 |
| WO | WO 2019/138350 | 7/2019 |
| WO | WO 2019/145253 | 8/2019 |
| WO | WO 2019/158996 | 8/2019 |
| WO | WO 2019/161245 | 8/2019 |
| WO | WO 2019/180104 | 9/2019 |
| WO | WO 2019/180179 | 9/2019 |
| WO | WO 2019/180181 | 9/2019 |
| WO | WO 2019/191245 | 10/2019 |
| WO | WO 2019/193604 | 10/2019 |
| WO | WO 2018/135477 | 11/2019 |
| WO | WO 2018/135478 | 11/2019 |
| WO | WO 2019/211410 | 11/2019 |
| WO | WO 2019/219868 | 11/2019 |
| WO | WO 2019/219871 | 11/2019 |
| WO | WO 2019/219872 | 11/2019 |
| WO | WO 2019/219874 | 11/2019 |
| WO | WO 2019/219876 | 11/2019 |
| WO | WO 2019/219881 | 11/2019 |
| WO | WO 2019/219882 | 11/2019 |
| WO | WO 2019/219883 | 11/2019 |
| WO | WO 2019/219884 | 11/2019 |
| WO | WO 2019/219885 | 11/2019 |
| WO | WO 2019/229210 | 12/2019 |
| WO | WO 2019/229211 | 12/2019 |
| WO | WO 2019/229214 | 12/2019 |
| WO | WO 2019/229220 | 12/2019 |
| WO | WO 2019/229221 | 12/2019 |
| WO | WO 2019/229222 | 12/2019 |
| WO | WO 2019/229223 | 12/2019 |
| WO | WO 2019/229224 | 12/2019 |
| WO | WO 2019/234145 | 12/2019 |
| WO | WO 2019/234146 | 12/2019 |
| WO | WO 2019/234148 | 12/2019 |
| WO | WO 2019/234149 | 12/2019 |
| WO | WO 2019/234151 | 12/2019 |
| WO | WO 2019/234152 | 12/2019 |
| WO | WO 2019/234153 | 12/2019 |
| WO | WO 2019/234161 | 12/2019 |
| WO | WO 2019/234162 | 12/2019 |
| WO | WO 2019/234163 | 12/2019 |
| WO | WO 2019/234164 | 12/2019 |
| WO | WO 2019/234166 | 12/2019 |
| WO | WO 2019/234167 | 12/2019 |
| WO | WO 2019/234169 | 12/2019 |
| WO | WO 2019/239259 | 12/2019 |
| WO | WO 2019/241556 | 12/2019 |
| WO | WO 2019/243582 | 12/2019 |
| WO | WO 2019/243588 | 12/2019 |
| WO | WO 2020/003110 | 1/2020 |
| WO | WO 2020/011760 | 1/2020 |
| WO | WO 2020/011795 | 1/2020 |
| WO | WO 2020/011797 | 1/2020 |
| WO | WO 2020/016438 | 1/2020 |
| WO | WO 2020/028312 | 2/2020 |
| WO | WO 2020/028537 | 2/2020 |
| WO | WO 2020/030686 | 2/2020 |
| WO | WO 2020/030700 | 2/2020 |
| WO | WO 2020/030706 | 2/2020 |
| WO | WO 2020/064707 | 4/2020 |
| WO | WO 2020/064911 | 4/2020 |
| WO | WO 2020/073047 | 4/2020 |
| WO | WO 2020/089429 | 5/2020 |
| WO | WO 2020/132211 | 6/2020 |
| WO | WO 2020/176236 | 9/2020 |
| WO | WO 2020/187797 | 9/2020 |
| WO | WO 2020/198280 | 10/2020 |
| WO | WO 2020/219430 | 10/2020 |
| WO | WO 2020/234785 | 11/2020 |
| WO | WO 2020/242881 | 12/2020 |
| WO | WO 2020/243756 | 12/2020 |
| WO | WO 2020/264174 | 12/2020 |
| WO | WO 2021/046275 | 3/2021 |
| WO | WO 2021/062265 | 4/2021 |
| WO | WO 2021/067691 | 4/2021 |
| WO | WO 2021/119478 | 6/2021 |
| WO | WO 2021/150777 | 7/2021 |
| WO | WO 2021/152013 | 8/2021 |
| WO | WO 2021/191106 | 9/2021 |
| WO | WO 2023/040546 | 12/2021 |
| WO | WO 2022/056542 | 3/2022 |
| WO | WO 2022/063650 | 3/2022 |
| WO | WO 2022/072944 | 4/2022 |
| WO | WO 2022/074136 | 4/2022 |
| WO | WO 2022/076862 | 4/2022 |
| WO | WO 2022/076948 | 4/2022 |
| WO | WO 2022/109589 | 5/2022 |
| WO | WO 2022/109590 | 5/2022 |
| WO | WO 2022/109591 | 5/2022 |
| WO | WO 2022/173970 | 8/2022 |
| WO | WO 2022/173977 | 8/2022 |
| WO | WO 2022/174249 | 8/2022 |
| WO | WO 2023/226779 | 9/2022 |
| WO | WO 2023/278599 | 1/2023 |
| WO | WO 2023/014742 | 2/2023 |
| WO | WO 2023/049813 | 3/2023 |
| WO | WO 2024/160098 | 4/2023 |
| WO | WO 2023/076461 | 5/2023 |
| WO | WO 2023/076869 | 5/2023 |

(56) References Cited

FOREIGN PATENT DOCUMENTS

| WO | WO 2023/230157 | 11/2023 |
| WO | WO 2024/104184 | 5/2024 |
| WO | WO 2024/243154 | 11/2024 |
| WO | WO 2025/226734 | 10/2025 |

OTHER PUBLICATIONS

International Search Report and Written Opinion received in PCT Application No. PCT/EP2019/064136 , dated Sep. 6, 2019 in 21 pages.
International Preliminary Report on Patentability and Written Opinion received in PCT Application No. PCT/EP2019/064136, dated Dec. 10, 2020 in 17 pages.
Kong et al., "A Stein Equation Approach for Solutions to the Diophantine Equations," 2010 Chinese Control and Decision Conference, Xuzhou, May 26, 2010, pp. 3024-3028.
Koseli et al., "Online Viscosity Measurement of Complex Solutions Using Ultrasound Doppler Velocimetry", Turk J Chem, Jan. 2006, vol. 30, pp. 297-305.
McCormick et al., "Resolution of a 2/spl pi/ Ambiguity Problem in Multiple Frequency Spectral Estimation," in IEEE Transactions on Aerospace and Electronic Systems, Jan. 1995, vol. 31, No. 1, pp. 2-8.
Syrmos et al., "A Generalized Bezout Equation in Output Feedback Design," Proceedings of the 31st IEEE Conference on Decision and Control, Tucson, AZ, USA, Dec. 1992, vol. 4, pp. 3590-3594.
Udesen et al., "A Simple Method to Reduce Aliasing Artifacts in Color Flow Mode Imaging", IEEE Ultrasonics Symposium, 2005, Rotterdam, The Netherlands, Sep. 18-21, 2005, pp. 1352-1355.
"ABMD—Taking a Closer Look at Impella ECP as the Pivotal Trial Gets Underway", Guggenheim, Press Release, Mar. 29, 2022, pp. 4.
Vollkron et al., "Advanced Suction Detection for an Axial Flow Pump", Artificial Organs, 2006, vol. 30, No. 9, pp. 665-670.
Vollkron et al., "Development of a Suction Detection System for Axial Blood Pumps", Artificial Organs, 2004, vol. 28, No. 8, pp. 709-716.
Lombardi et al., "Flow Rate Profiler: an instrument to measure blood velocity profiles", Ultrasonics, 2001, vol. 39, pp. 143-150.
Mushi et al., "Identification of Fluidic Element Models to Simulate the Short-Term Baroreflex", Proceedings of the 45th IEEE Conference on Decision & Control, San Diego, CA, Dec. 13-15, 2006, pp. 6.
"Understanding Hot-Wire Anemometry", Advanced Thermal Solutions, Inc., 2007, pp. 13-17.
Yuanyuan et al., "Characteristics Analysis for Doppler Ultrasound Blood Flow Signals", China Medical Device Information, 5(1), Feb. 28, 1999, pp. 36-42.
Atkinson et al., "Pulse-Doppler Ultrasound and Its Clinical Application", The Yale Journal of Biology and Medicine, 1977, vol. 50, pp. 367-373.
Leguy et al., "Assessment of Blood Volume Flow in Slightly Curved Arteries from a Single Velocity Profile", Journal of Biomechanics, 2009, pp. 1664-1672.
Sinha et al., "Effect of Mechanical Assistance of the Systemic Ventricle in Single Ventricle Circulation with Cavopulmonary Connection", The Journal of Thoracic and Cardiovascular Surgery, Apr. 2014, vol. 147, No. 4, pp. 1271-1275.
Vieli, A., "Doppler Flow Determination", BJA: British Journal of Anaesthesia, 1988, vol. 60, pp. 107S-112S.
Zhang, Dabiao et al., "Design of Microwave Velocity and Distance Monitor System", Instrument Technique and Sensor, Hebei Normal University, Apr. 25, 2004, pp. 3.
Escudeiro et al., "Tribological behavior of uncoated and DLC-coated CoCr and Ti-alloys in contact with UHMWPE and PEEK counterbodies;" Tribology International, vol. 89, 2015, pp. 97-104.
Hinkel et al., "Pump Reliability and Efficiency Increase Maintenance Program—Utilizing High Performance Thermoplastics;" Proceedings of the 16th International Pump Users Symposium, Texas A&M University. Turbomachinery Laboratories; 1999, pp. 115-120.
Murali, Akila, "Design of Inductive Coils for Wireless Power Transfer to Pediatric Implants", A graduate project submitted in partial fulfillment of the requirements for the degree of Master of Science in Electrical Engineering, California State University, Northridge, May 2018, pp. 37.
Neale, Michael J., "The Tribology Handbook;" 1999, Butterworth-Heinemann, Second Edition, pp. 582. (3 PARTS).
Park et al., "A Novel Electrical Potential Sensing Method for in Vitro Stent Fracture Monitoring and Detection", Jan. 1, 2011, vol. 21, No. 4, pp. 213-222.
Sak et al., "Influence of polyetheretherketone coatings on the Ti—13Nb—13Zr titanium alloy's bio-tribological properties and corrosion resistance;" Materials Science and Engineering: C, vol. 63, 2016, pp. 52-61.
Ai, X. (2013). Radial Bearings. In: Wang, Q.J., Chung, YW. (eds) Encyclopedia of Tribology. Springer, Boston, MA https://doi.org/10.1007/978-0-387-92897-5_334, accessed Oct. 18, 2024, pp. 4.
"Edwards SAPIEN 3 Kit—Transapical and Transaortic", Edwards Lifesciences, Released Nov. 8, 2016, pp. 11. chrome-extension://efaidnbmnnnibpcajpcglclefindmkaj/https://edwardsprod.blob.core.windows.net/media/De/sapien3/doc-0045537b%20-%20certitude.pdf.
GGB by Timken Bearings FAQ; "What is a Slide Bearing ?;" https://www.ggbearings.com/en/why-choose-ggb/faq/bearings-faq/what-slide-bearing; accessed Oct. 10, 2024, pp. 1.
Google.com, "Spider Bearing—Search Results;" https://www.google.com/search?q=spider+bearing&rlz=X1C1GCEA_enUS1059US1059&oq=spider+beari&gs_lcrp=EgZjaHJvbWUqCQgAEEUYOxiABDIJCAAQRRg7GIAEMgYIARBFGDkyBwgCEAAYgAQyBwgDEAAYgAQyBwgEEAAYgAQyBwgFEAAYgAQyBwgGEAAYgAQyBggHEEUYPKgCALACAA&sourceid=chrome&ie=UTF-8, accessed Oct. 18, 2024, pp. 4.
Gopinath, Divya, "A System for Impedance Characterization of Coronary Stents", University of Strathclyde Engineering, Thesis, Aug. 2015, pp. 77.
HeartMate 3™ Left Ventricular Assist System, Instructions for Use, Thoratec Corporation, Aug. 2017, pp. 536. [Uploaded in 3 parts].
McMaster-Carr Online Catalog, "Bearings search results;" https://www.mcmaster.com/products/bearings/; accessed Oct. 18, 2024, pp. 5.
McMaster-Carr Online Catalog, "Slide Bearings search results;" https://www.mcmaster.com/products/slide-bearings/; accessed Oct. 18, 2024, pp. 21.
RBCBearings.com, "RBC Bearings Incorporated—Products;" https://www.rbcbearings.com/Products; accessed Oct. 18, 2024, pp. 2.
SKF.com; "Products: Bearings;" https://www.skf.com/us/products/bearings; accessed Oct. 18, 2024, pp. 8.
Wikipedia, "Plain Bearing," https://en.wikipedia.org/wiki/Plain_bearing; accessed Oct. 18, 2024, pp. 10.
Chung et al., "Improved Efficiency Characteristics of Wireless Power Charging System for Superconducting MAGLEV Train Using Inserted Permanent Magnets," 2018 IEEE International Symposium on Electromagnetic Compatibility, 2018, pp. 564-567.
"ECG Electrodes product comparison chart," 3m.com, 2018, https://multimedia.3m.com/mws/media/14908830/red-dot-ecg-electrodes-comparison-chart.pdf, accessed May 18, 2025, 1 page.
Eeckhout, MD, PhD, et al., "Handbook of Complications During Percutaneous Cardiovascular Interventions", 2007 Informa UK Ltd., Ch. 12, pp. 167-177.
"FDA Approves Abiomed's Heart Pump Impella, Shares Rise", Reuters 2008 press release, Jun. 2, 2008, https://jp.reuters.com/article/us-abiomed/fda-approves-abiomeds-heart-pump-impella-shares-rise-idUSBNG131420080602/, 1 page.
Mack-Haynes, Robin, "Fasteners Made Easy," New Mexico State University, https://pubs.nmsu.edu/_c/C232.pdf, accessed May 18, 2025, p. 8.
Tan et al., "Surface Engineering and Patterning Using Parylene for Biological Applications." Materials, Mar. 15, 2010, vol. 3, No. 3, pp. 1803-1832.
Vincent, MD, PhD, et al., "Textbook of Critical Care", Elsevier, 7th Edition, Ch. 78, 2017, pp. 520-531.e3.

(56) References Cited

OTHER PUBLICATIONS

Delgado et al., "Interventional Treatment of Advanced Ischemic Heart Disease", Percutaneous Mechanical Assist Devices, Ch. 6, Springer, 2009, pp. 85-91.

Delgado et al., "Interventional Treatment of Advanced Ischemic Heart Disease", The Future of Treatment of Advanced Ischemic Heart Disease, Ch. 8, Springer, 2009, pp. 129-142.

Lake et al., "Pediatric Cardiac Anesthesia", 4th Edition, 2005, Ch. 15, pp. 291-303.

Machiraju, Venkat R., "Redo Cardiac Surgery in Adults", Practical Approaches to the Current "On-Pump" Redo Coronary Artery Bypass Surgery, Ch. 2, Springer, 2012, pp. 7-19.

Machiraju, Venkat R., "Redo Cardiac Surgery in Adults", Options for Advanced Mechanical Support for Cardiogenic Shock Complicating Cardiac Reoperations, Ch. 9, Springer, 2012, pp. 67-80.

Machiraju, Venkat R., "Redo Cardiac Surgery in Adults", Percutaneous Approaches to Valvular Heart Disease After Previous Cardiac Surgery, Ch. 21, Springer, 2012, pp. 195-200.

Mullins, Charles E., MD, "Cardiac Catheterization in Congenital Heart Disease: Pediatric and Adult", Blackwell Futura, 2006, Chapters 3, 4 and 32, pp. 101.

New Hampshire Ball Bearings, Inc., "Engineering Reference, Rod End & Spherical Bearings", https://www.nhbb.com/index.php/knowledge-center/engineering-reference/rod-end-spherical-bearings/self-lubricating-liner-systems, 2021, p. 13.

Parrillo et al., "Critical Care Medicine", Principles of Diagnosis and Management in the Adult, Elsevier, 4th Edition, 2014, Chapters 4 & 29, pp. 47-58.e1 and 442-469.e4.

Radiologyinfo.org, "Subcutaneous Port," Definition, https://www.radiologyinfo.org/en/glossary?id=ezNFREEzNEFFLTI5OTAtNDVFNy04MkVBLTA1RDVGMDdBMzNFRHO=&i=1&b=0&modal=1, accessed Sep. 2, 2025, 1 page.

Schmitz-Rode, T, Graf, J, Pfeffer, J. et al. "An Expandable Percutaneous Catheter Pump for Left Ventricular Support: Proof of Concept", JACC. Jun. 2005, 45 (11) 1856-1861.

Sigg et al., "Cardiac Electophysiology Methods and Models", Springer, Clinical Perspective: Electrophysiology in the Young and Patients with Congenital Heart Disease, Ch. 23, 2010, pp. 457-477.

Vincent, MD, PhD, et al., "Textbook of Critical Care", Mechanical Support in Cardiogenic Shock, Elsevier, 7th Edition, Ch. 91, 2017, pp. 637-648.e3.

Walser, Eric, "Venous access ports: indications, implantation technique, follow-up, and complications;" Cardiovasc Intervent Radial, Aug. 2012; vol. 35, No. 4, pp. 751-764. (Abstract Only).

* cited by examiner

LINE DEVICE FOR CONDUCTING A BLOOD FLOW FOR A HEART SUPPORT SYSTEM, AND PRODUCTION AND ASSEMBLY METHOD

BACKGROUND

Field

The invention relates to cardiac support systems, devices, and methods.

Description of the Related Art

Cardiac support systems, in particular left ventricular support systems, can be differentiated in terms of their position on the heart and their access to the blood stream. Long-term support systems can be positioned at the apex of the heart (transapically) and bypass the left ventricle by pumping blood from the apex of the heart through a hose directly into the aorta. Another type of access can be used in particular for short-term support of the heart. For example, the cardiac support system can be a ventricular support system as a bridging measure; as a bridge to a transplant (bridge to decision, bridge to transplant). The natural aortic valve can be used to create a connection between the pump inlet and the pump outlet. With such an arrangement of the cardiac support system, the aorta can be used as an access route (transaortic) in the context of a minimally invasive surgical procedure and a sternotomy can be avoided.

SUMMARY

An underlying object of the invention is to specify an improved line device for a cardiac support system, in particular with long-lasting connection reliability and suitable flexibility, as well as a method for the production and assembly of said device.

With that in mind, the approach presented here proposes a line device for conducting a blood flow for a cardiac support system, a method for producing a line device and a method for assembling a cardiac support system according to the main claims. Advantageous further developments and improvements of the device specified in the independent claim are possible using the measures listed in the dependent claims.

This approach presents a line device for conducting a blood flow for a cardiac support system, for example a left ventricular cardiac support system. The line device can be used as a flow channel, in which the blood flow can be conducted from the pump inlet in a left ventricle to the pump outlet inside an aorta. A head unit of the cardiac support system can be attached to the line device at one end, and a further component of the cardiac support system, for example an impeller housing, can be attached at another end. The attachment can be realized by means of a form-locking connection. Additionally or alternatively, the connection can also be realized in a force-locking manner. The line device can advantageously be configured to enable a transfemoral surgical procedure (access via the groin) to implant the cardiac support system. This can in particular be achieved via the ratio of flexibility and stiffness of the line device.

A line device for conducting a blood flow for a cardiac support system is presented. The line device comprises a main body, wherein the main body comprises a proximal (first) attachment section at a first end, upstream, for attaching the line device to a head unit of the cardiac support system and comprises a distal (second) attachment section at a second end, downstream, for attaching the line device to an outlet unit of the cardiac support system. The attachment sections are formed to be connectable in a form-locking and additionally or alternatively force-locking manner. The main body further comprises a structural section having at least one stiffening recess between the attachment sections, wherein the at least one stiffening recess is formed to change the stiffness of the main body.

The line device can be made of a biocompatible material and can be understood to be a flow channel for flexibly connecting components of a cardiac support system for conducting a blood flow between the ventricle and the blood vessel. The line device can be used as a suction hose for the cardiac support system to initiate blood flow and to conduct it to an outlet section of the cardiac support system. The cardiac support system can, for example, be understood to be a left ventricular support system (LVAD, left ventricular assist device) or other ventricular support system (VAD, ventricular assist device). The main body of the line device can be configured as a hollow cylinder, for example, and substantially have a tubular geometry. The proximal attachment section at a first end of the main body can be understood to be a first attachment section and can be disposed in the left ventricle, for example, as a left ventricular support system when the cardiac support system is implanted. The distal attachment section at a second end of the main body can be understood to be a second attachment section and can be disposed in the aorta, for example, when the left ventricular support system is implanted. A head unit of the cardiac support system, for example a sensor assembly, can be attached to the proximal attachment section. The structural section can, for example, be a main body section having a predefined sectional contour for changing the stiffness of the line device, for example to enable the use of the line device during a transfemoral surgical procedure. The stiffness can be changed via the configuration of the sectional contour of the structural section, in particular a number and shape of the at least one stiffening recess. The at least one stiffening recess can have a spiral shape or a wave shape, for example. The inlet section can, for example, be realized by a multi-part window in the main body. The inlet section can be configured to enable the initiation of blood flow into the main body of the line device.

According to one embodiment, at least one of the attachment sections can comprise at least one connection element for form-locking connection. The connection element can be, for example, a recess or an elevation, for example a knob, or a threaded element. The connection element as a recess or as a knob can, for example, be round, oval, triangular, polygonal or star-shaped. It is also possible for each of the attachment sections to comprise a plurality of connection elements, wherein the connection elements can also be formed differently. Depending on the shape of the attachment sections, the correspondingly formed engaging or gripping connection partner of the connection element can be realized for connecting the line device to the head unit and additionally or alternatively to the outlet unit of the cardiac support system.

According to a particularly advantageous embodiment, the main body can comprise an inlet section between the structural section and the proximal or first attachment section, wherein the inlet section is formed to allow initiation of the blood flow. This makes it possible to achieve a very advantageous guidance of a blood flow, i.e. make advantageous use of the structural section.

Furthermore, according to one embodiment, at least one portion of the main body can be made of a shape memory material according to an embodiment. The shape memory material can be a biocompatible shape memory polymer, or a biocompatible shape memory alloy, such as Nitinol for example. It is also possible for the entire main body to be made of the shape memory material. The use of Nitinol as a shape memory material is advantageous, because the Nitinol material is a proven material in the field of medicine, in particular in the field of cardiovascular medicine, for example for heart valve prostheses, stents and vascular prostheses, and, due to its biocompatibility and the shape memory property, makes it possible to realize even complex structures in a small installation space.

According to one embodiment, the line device can also comprise a cable groove. The cable groove can be configured to guide a cable along the main body. The cable groove can in particular be configured to extend helically around the structural section. The cable can be a cable for signal transmission, for example, and additionally or alternatively for power transmission. If, for example, the head unit attached to the line device comprises a sensor, the cable held by the cable groove can be configured to take sensor data from the head unit at a pump tip inside the heart valve and transmit it to a control device. The cable groove can advantageously help prevent the cable from breaking during operational movements of the cardiac support system.

According to one embodiment, the structural section of the line device can extend over at least half of the main body. This is advantageous with regard to implantation of the line device, in particular in the case of transfemoral access, for enabling a predefined ratio of flexibility and stiffness of the line device via the configuration of the structural section. The flexibility of the line device can be advantageous, for example when being pushed through an aortic arch, and the stiffness can advantageously prevent the line device from bending when being pushed through a blood vessel.

The structural section can also comprise a plurality of slotted holes as the at least one stiffening recess. The longitudinal holes can be evenly spaced and be configured to extend obliquely transverse to the longitudinal axis of the structural section. The plurality of slotted holes can also be configured to extend helically around the structural section. The use of a plurality of slotted holes as the at least one stiffening recess is advantageous, for example, for adjusting the flexibility of the line device via the spacing of the individual slotted holes.

According to one embodiment, the line device can also comprise a sealing layer. The sealing layer can be disposed on the structural section and configured to seal the at least one stiffening recess in a fluid-tight manner. The fluid-tight sealing of the at least one stiffening recess by means of the sealing layer is advantageous for conducting the blood flow to be able to conduct the blood flow to the outlet unit without loss. The sealing section can be realized, for example, by potting or overmolding the structural section with a flexible plastic, such as polyurethane or silicone.

According to one embodiment, the main body can also comprise a bending point, wherein the bending point is disposed between the inlet section and the distal attachment section. The main body can have a first longitudinal axis between the distal attachment section and the bending point, and the main body can have a second longitudinal axis oblique to the first longitudinal axis between the bending point and the proximal attachment section, whereby the main body is curved in a region of the bending point. The bending point can be configured to give the main body a curved shape corresponding to the human anatomy, for example, to enable a positioning of the inlet section in the center of a ventricle to advantageously avoid suctioning of the inlet unit to a ventricular wall.

According to one embodiment, an inner diameter of the main body can furthermore change from the proximal attachment section to the distal attachment section. For example, a cross-section of the inner diameter can taper in the direction of the distal attachment section. The change in the inner diameter of the main body can advantageously improve the flow properties of the initiated blood flow.

According to one embodiment, the inlet section can comprise at least one inlet opening cut into the main body. The inlet opening can be rectangular, for example, or shaped as a rectangle with a circular arc in the direction of the structural section. The inlet section can also comprise a plurality of inlet openings, for example three inlet openings. In this case, the inlet openings can be evenly spaced, for example, whereby a narrow web can connect the proximal attachment section to the structural section between two adjacent inlet openings, for example. By forming at least one inlet opening, which can be cut into the main body, there is advantageously no need for an additional structural element for initiating the blood flow, which is advantageous with regard to a compact design.

According to one embodiment, the distal attachment section can comprise a lead-out opening for leading out a guide wire for positioning the cardiac support system. The guide wire can be inserted at the proximal attachment section, for example, and led out through the lead-out opening. This is advantageous to enable a positioning of the line device along the guide wire and also to prevent damage to the guide wire or pump components.

A cardiac support system is presented as well. The cardiac support system can comprise a head unit, an outlet unit and an embodiment of the aforementioned line device. The line device can be disposed between the head unit and the outlet unit and connected to the head unit and the outlet unit.

A method for producing a line device for conducting a blood flow for a cardiac support system is presented as well. The method includes the following steps:

forming a main body from a semi-finished product made of a shape memory material, wherein the main body comprises a proximal attachment section at a first end for attaching the line device to a head unit of the cardiac support system and comprises a distal attachment section at a second end for attaching the line device to an outlet unit of the cardiac support system, wherein the attachment sections are formed to be connectable in a form-locking and/or force-locking manner, wherein the main body comprises a structural section having at least one stiffening recess between the attachment sections, wherein the at least one stiffening recess is formed to change the stiffness of the main body, and heat treating the formed main body in order to emboss a predetermined shape on the main body.

An embodiment of the aforementioned line device can advantageously be produced by carrying out the aforementioned method.

A method for assembling an embodiment of the aforementioned cardiac support system is presented as well. The method includes the following step:

producing a form-locking and/or force-locking connection of the head unit and the outlet unit to the line device to assemble the cardiac support system.

BRIEF DESCRIPTION OF THE DRAWINGS

Design examples of the invention presented here are shown schematically in the drawings and explained in more detail in the following description. The figures show.

DETAILED DESCRIPTION

In the following description of favorable design examples of the present invention, the same or similar reference signs are used for the elements shown in the various figures, which have a similar effect, whereby a repeated description of these elements is omitted.

Figure 1:
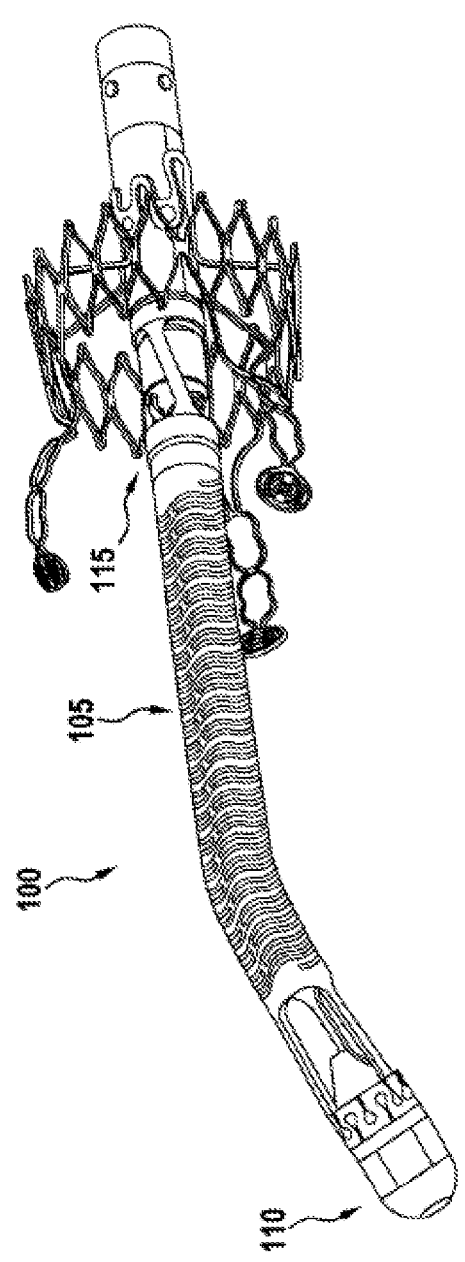
FIG. 1 a perspective illustration of a cardiac support system with a line device for conducting a blood flow.

FIG. 1 shows a cardiac support system 100 with a hose-like line device 105 for conducting a blood flow according to a design example. The figure shows a view of the cardiac support system 100 as an overall system which, as an example, is configured here as a left ventricular support system. The cardiac support system 100 comprises a head unit 110, an outlet unit 115 and the line device 105. The line device 105 is disposed between the head unit 110 and the outlet unit 115 and connected to the head unit 110 and the outlet unit 115. The line device 105 can also be referred to as a suction hose, which, in the implanted state of the cardiac support system 100, connects a pump inlet inside a ventricle to an outlet inside the aorta.

The cardiac support system 100 has a cylindrical, elongated structure with a substantially constant outer diameter and rounded, tapering ends for easy placement in a blood vessel, such as the aorta, by means of a catheter. The cardiac support system 100 is furthermore bent in the direction of the head unit 110, whereby the bend is configured, for example, as an obtuse angle with respect to a longitudinal axis of the cardiac support system 100.

Figures 2, 3:
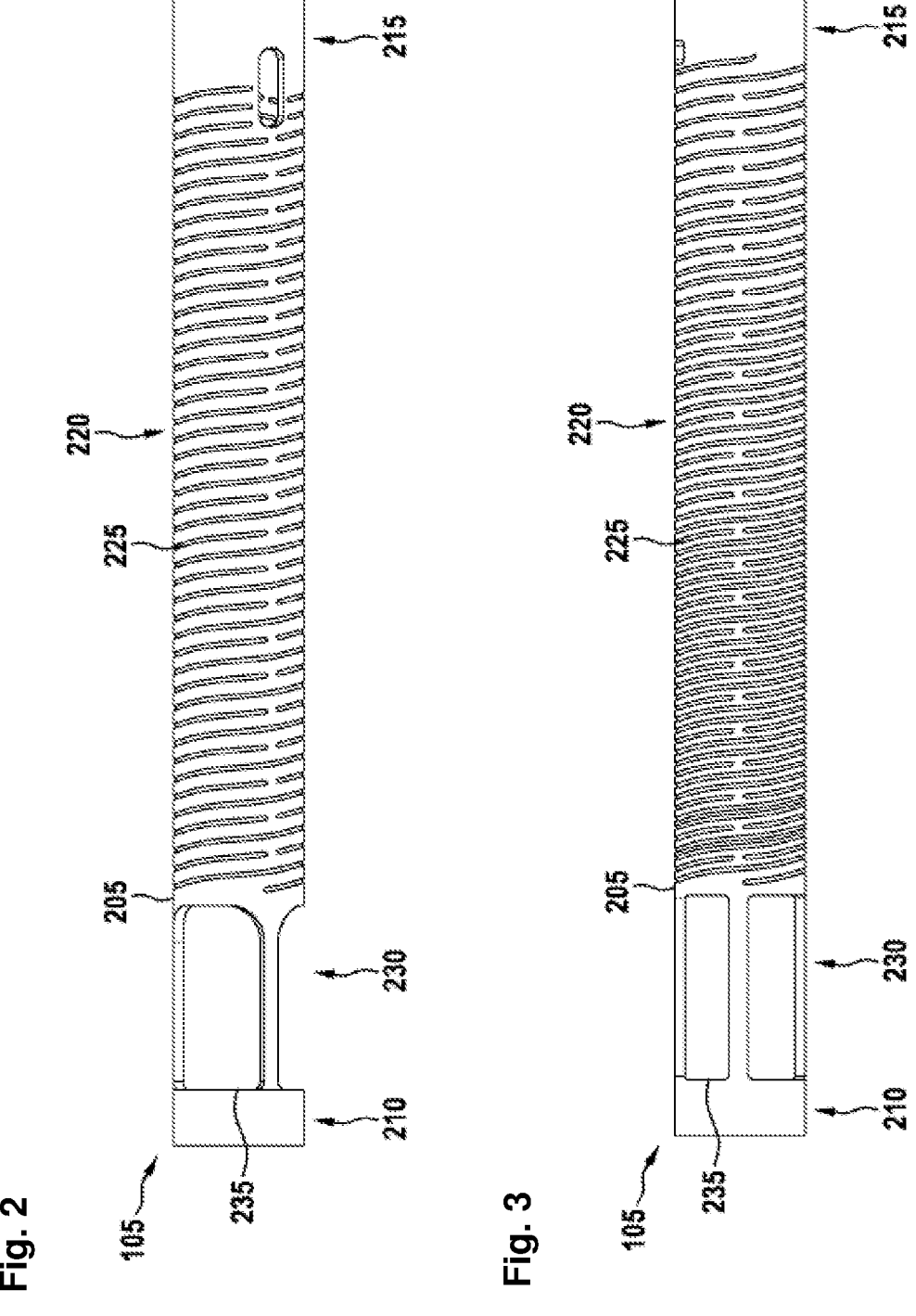
FIG. 2 a side view of a line device for conducting a blood flow for a cardiac support system.
FIG. 3 a side view of a further line device for conducting a blood flow.

FIG. 2 shows a schematic illustration of a line device 105 for conducting a blood flow for a cardiac support system according to a design example in a side view. The line device 105 can also be referred to as a laser-cut suction hose. The line device 105 comprises a main body 205. The main body 205 is tube-shaped for example. The main body 205 comprises a proximal attachment section 210 at a first end for attaching the line device 105 to a head unit of the cardiac support system and comprises a distal attachment section 215 at a second end for attaching the line device 105 to an outlet unit of the cardiac support system. The attachment sections 210 and 215 are formed to be connectable in a form-locking and/or force-locking manner. The main body 105 further comprises a structural section 220 having at least one stiffening recess 225 between the attachment sections 210, 215, wherein the at least one stiffening recess 225 is formed to change the stiffness of the main body 205. The main body 205 also comprises an inlet section 230 between the structural section 220 and the proximal attachment section 205, wherein the inlet section 230 is formed to allow initiation of the blood flow.

The structural section 220 extends over at least half of the main body 205 as shown here according to design examples. According to the design example shown here, the structural section 220 comprises a plurality of slotted holes as the stiffening recess 225. The stiffening recesses 225 extend over the entire structural section 220, for example, and are disposed helically around said section.

According to the design example shown here, the inlet section 230 comprises at least one inlet opening 235 cut into the main body 205. As an example, the inlet opening 235 here is realized as a multi-part window. There is therefore no need for an additional structural element for the inflow of blood initiated by the inlet section 230. According to the design example shown here, the inlet section 230 comprises three rectangular inlet openings 235, which are rounded in the direction of the structural section 220 in the form of a circular arc.

FIG. 3 shows a schematic illustration of a line device 105 for conducting a blood flow for a cardiac support system according to a design example. The depicted line device 105 is the same as or similar to the line device of FIG. 2 described above, except for the distance between the plurality of slotted holes as the stiffening recess 225. The structural section 220 shown here has a finer sectional contour than the coarser sectional contour shown in FIG. 2. Adjacent slotted holes are therefore closer to one another here in FIG. 3. The ratio of flexibility and stiffness of the line device 105 can be set via the laser-cut structure, for example. This is of great importance with respect to transfemoral access during a surgical procedure to implant the cardiac support system with the line device 105, because the support system, also referred to as the pump, has to be flexible enough to be pushed through the aortic arch and also requires a certain amount of stiffness to be pushed through the narrow blood vessels in axial direction by an acting force without bending.

Another difference to the already described design example of the line device 105 is the configuration of the inlet section 230. In FIG. 3, the inlet section 230 also comprises three inlet openings 235. The inlet openings 235 here are rectangular in shape, as an example, whereby the sides of each inlet opening 235 that are opposite to one another along the longitudinal axis of the line device 105 are longer than the sides that are opposite to another transverse to the longitudinal axis. The proximal attachment section 210 and the distal attachment section 215 correspond to the design example described in FIG. 2 above.

Figure 4:
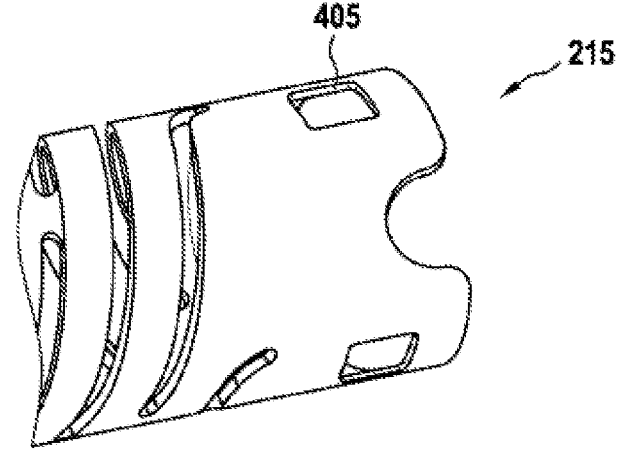
FIG. 4 a broken off perspective illustration of a distal attachment section of a line device.

FIG. 4 shows a schematic illustration of a distal attachment section 215 of a line device according to a design example. The line device is the same as or similar to the line device of one of the figures described above. The distal attachment section 215 comprises at least one connection element 405 for form-locking connection. The connection element 405 is shown here as an example as a rectangular recess. The connection element 405 can alternatively also be realized as an elevation, such as the connection element shown in the following FIG. 5. The proximal attachment section optionally comprises a corresponding or similar connection element 405 as the connection element 405 shown here for form-locking connection. The connection element 405 is implemented with the aid of a laser-cut contour, for example, to realize the connection in a fatigue endurable and reliable manner using a key-and-lock principle. Such a laser-cut distal attachment section 215 based on the key-and-lock principle is shown here as an example. The connection element 405, which is rectangular here, can also have a different geometric shape. For example, the connection element 405 can be realized as a circle, as an oval, as a triangle, as a polygon or as a star. If the connection element 405 has an elevation, the elevation can have a flattened section as described with reference to FIG. 7.

Figure 5:
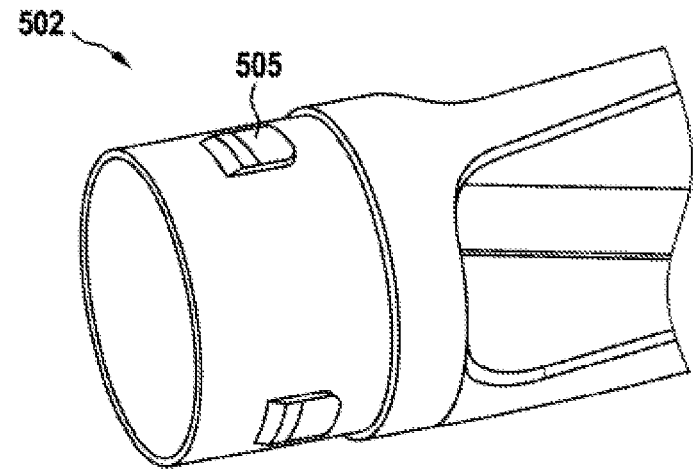
FIG. 5 a broken off perspective illustration of an impeller housing of a cardiac support system.

FIG. 5 shows a schematic illustration of an impeller housing 502 of a cardiac support system. The impeller housing 502 can correspond to the outlet unit of the cardiac support system described with reference to FIG. 1 or be part of the outlet unit. In a side view of the impeller housing 502, a rectangular connection element 505 is shown as a knob on the impeller housing 505. The counterpart, and therefore connection partner of the recess described with reference to FIG. 4, is shown here as an example as the connection element. The connection element shown here has a flattened side to facilitate the assembly process, i.e. the form-locking connection of the impeller housing 505 to the line device. The connection element for the form-locking connection of one of the attachment sections can be configured like the connection element 505 shown here and realized on one of the attachment sections.

Figure 6:
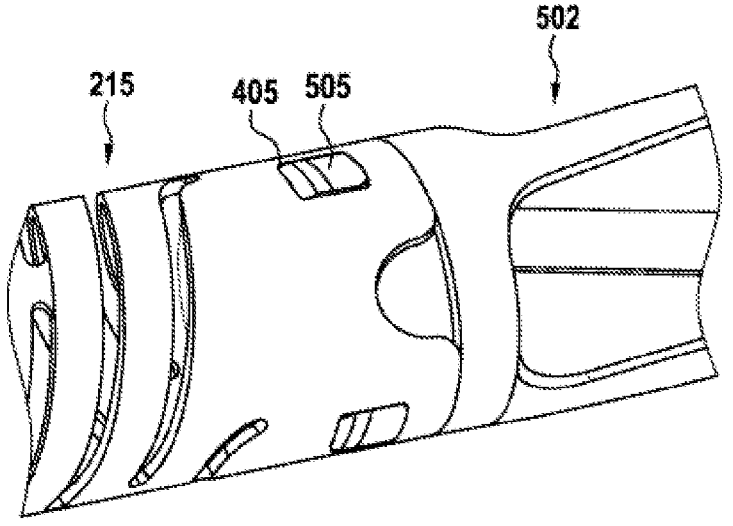
FIG. 6 a broken off perspective view of a distal attachment section of a line device connected to the impeller housing.

FIG. 6 shows a schematic illustration of a distal attachment section 215 of a line device according to a design example connected to the impeller housing 502. The distal attachment section 215, as described with reference to FIG. 4 above, and the impeller housing, as described with reference to FIG. 5, are shown in the connected, i.e. assembled state. An assembled form-locking attachment point between the line device in the form of the distal attachment section 215 and the adjacent structural element, the impeller housing 502, is accordingly shown here as an example. As an example, the connection element 505 here has a projecting shape with a flattened side to facilitate the form-locking connection when gripping the connection element 405. The distal attachment section 215 is configured as a part of the line device, which is realized as a Nitinol tube as an example.

Figure 7:
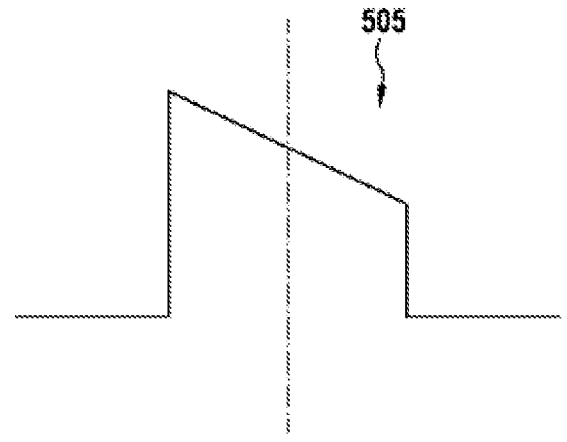
FIG. 7 a schematic illustration of a connection element.

FIG. 7 shows a schematic illustration of a connection element 505 according to a design example. The figure shows a cross-section of the connection element 505, which here has a flattened section. The shown connection element 505 is the same as or similar to the connection element as described with reference to FIG. 5 and FIG. 6 above.

Figure 8:
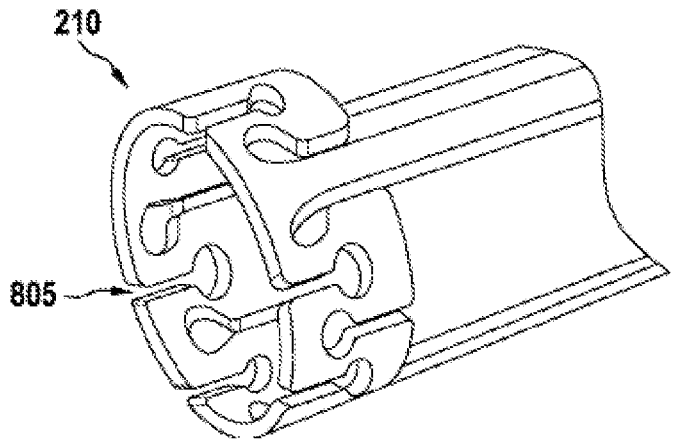
FIG. 8 a broken off perspective illustration of a proximal attachment section of a line device.

FIG. 8 shows a schematic illustration of a proximal attachment section 210 of a line device according to a design example. The line device is the same as or similar to the line device of one of the figures described above. The figure shows a laser cut at the proximal end of the line device as the proximal attachment section 210. The shape of the proximal attachment section 210 shown here allows widening and thus a force-locking press fit. According to the design example shown here, the head unit of the cardiac support system is connected to the proximal attachment section 210 in a force-locking manner. As an example, the proximal attachment section 210 comprises labyrinth recesses 805 to enable widening of the proximal attachment section 210 and to be able to create a force-locking connection to a corresponding counterpart. The labyrinth recesses 805 are realized circumferentially on the attachment section. Along the longitudinal axis of the line device, each labyrinth recess 805 has a slit-shaped opening that widens in a circular manner, whereby the slit-shaped openings of two adjacent labyrinth recesses 805 are opposite to one another.

Figure 9:
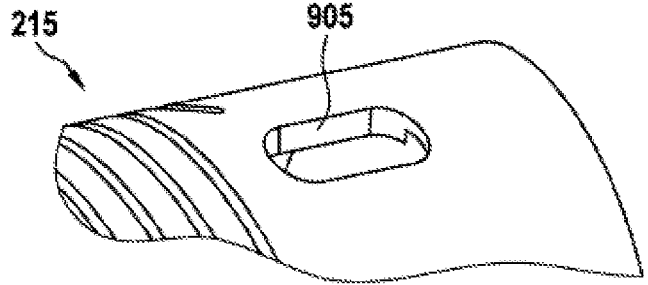
FIG. 9 a cut-out perspective illustration of a distal attachment section of a line device.

FIG. 9 shows a schematic illustration of a distal attachment section 215 of a line device according to a design example. The line device is the same as or similar to the line device of one of the figures described above. The distal attachment section 215 here comprises a lead-out opening 905 for leading out a guide wire for positioning the cardiac support system. The lead-out opening 905 has an elongated shape for example. The elongated shape of the lead-out opening 905 allows the guide wire to be led out and forwarded at a shallow angle. The guide wire is inserted through an opening in the proximal tip of the pump, i.e. the cardiac support system, and passed out through the lead-out opening 905. This allows the cardiac support system to be positioned along the guide wire without the guide wire touching or damaging the impeller.

Figure 10:
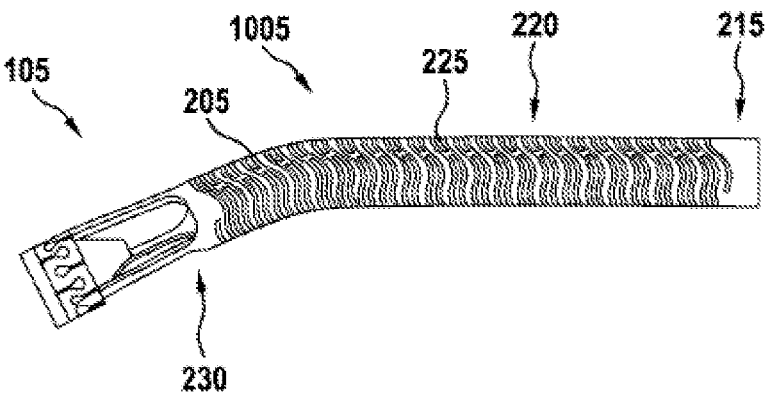
FIG. 10 a perspective illustration of a bending point of a line device.

FIG. 10 shows a schematic illustration of a bending point 1005 of a line device 105 according to a design example. The line device 105 is the same as or similar to the line device of one of the figures described above. The main body 205 comprises the bending point 1005, wherein the bending point 1005 is disposed between the inlet section 230 and the distal attachment section 215. As an example, the bending point 1005 is configured here to enable the positioning of the inlet section 230 in the center of the ventricle when implanting the cardiac support system with the line device 105. The line device 105 is bent at an obtuse angle along a first longitudinal axis by the bending point 1005. The line device accordingly has a first longitudinal axis, and a second longitudinal axis extends obliquely to the first longitudinal axis after the bending point 1005 to shape the main body 205 in a curved manner in the direction of the inlet section 230.

The main body 205 comprises a first longitudinal axis between the distal attachment section 215 and the bending point 1005. Between the bending point 1005 and the proximal attachment section 210, the main body 205 has a second longitudinal axis at an angle to the first longitudinal axis. The second longitudinal axis is at an obtuse angle to the first longitudinal axis. The main body 205 is curved in the region of the bending point 1005.

According to a design example, at least one portion of the main body 205 can be made of a shape memory material. In the design example shown here, the entire main body 205 is made of one material, for example Nitinol. Due to the shape memory properties of the Nitinol, a curved shape corresponding to the anatomy can be imparted after laser cutting the main body 205 from a Nitinol tube to be able to position the inlet section 230 in the center of the ventricle in order to avoid suctioning of the hose opening of the line device 105, i.e. the inlet section 230, to a ventricular wall. The Nitinol material is a proven material in the field of medicine, in particular in the field of cardiovascular medicine, for example for heart valve prostheses, stents and vascular prostheses. Nitinol combines the advantages of biocompatibility and the shape memory property that makes it possible to realize even complex structures in a small installation space. In the design example shown here, the main body 205 of the line device 105 is made of an elastic material, of Nitinol. A tubular geometry is a suitable semi-finished product for the machining of the main body 205. The semi-finished product can have a wall thickness of 0.25 to 0.5 millimeters, for example. The contour of the main body 205 shown here is realized by methods for material removal, for example laser cutting, by removing pipe volume at some locations. Punching and erosion methods or machining are alternatively possible as well. It is thus possible to impart a helix or wave shape into the tube of the main body 205. The spacing of the individual sections of the structural section 220 can also be varied. The distance between the individual sections can be 0.5 millimeters, for example. The dimensions of the stiffening recess 225 and the spacing of the stiffening recesses 225 changes the flexibility and stiffness of the line device 105. The larger the stiffening recess 225 and the smaller the spacing of the cuts, the more flexible the tube of the line device 105 becomes. The laser-cut contour can be given a specific shape as part of a heat treatment, for example, (e.g. with a temperature T of at least 500 degrees Celsius), e.g. with a bend of the main body 205 in the form of the bending point, or with different diameters, as described with reference to the following FIG. 11. The embossing process of the shape of the main body 205 is a plastic deformation without the occurrence of material failure.

Figure 11:
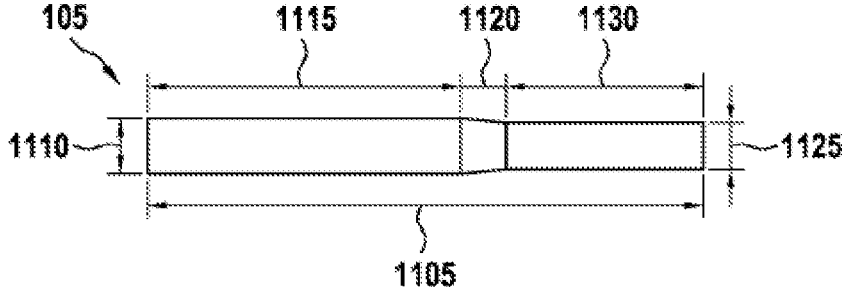
FIG. 11 a schematic side view of a line device.

FIG. 11 shows a schematic illustration of a line device 105 according to a design example. The line device 105 is the same as or similar to the line device of one of the figures described above. The figure shows a change in an inner diameter of the main body of the line device 105, which is illustrated using exemplary dimensions of the line device 105. The main body of the line device has a length of 62 millimeters illustrated by the label 1105. According to the design example shown here, an inner diameter of the main body changes from the proximal attachment section to the distal attachment section. The cross-section of the proximal attachment section has a diameter of 6 millimeters, as indicated by the label 1110. The label 1115 indicates a length of 35 millimeters of a section of the main body with the proximal attachment section having a continuous inner diameter of 6 millimeters. In the section marked by the label 1120, which has a length of 5 millimeters and adjoins the section of the label 1115, the inner diameter of the line device 105 tapers from 6 millimeters to 5.49 millimeters, as indicated by the label 1125. Over the remaining length of 22 millimeters of the main body of the line device 105 shown here, indicated by the label 1130, the inner diameter remains constant at 5.49 millimeters. The change in the inner diameter of the main body shown here can improve the flow properties of the blood flow. For this purpose, different diameters can be imposed on the line device 105 in axial direction as shown here. The inner diameter can in particular be larger in the region with the proximal attachment section indicated as an example by the label 1115 than in the region with the distal attachment section indicated by the label 1130. In the region corresponding to the label 1115, for example, a larger installation space can be available than in the region indicated by the label 1130, for example if the region 1130 is enclosed by a further structural element, for example a sleeve, during implantation of the cardiac support system for insertion of the cardiac support system into a catheter, as shown in the following FIG. 12.

Figure 12:
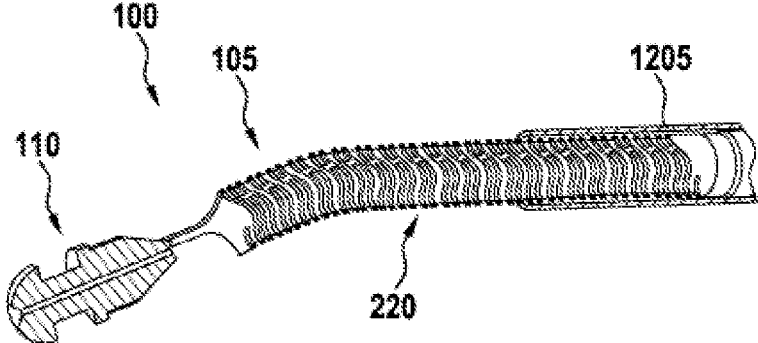
FIG. 12 a perspective, partially cross-sectional illustration of a part of a cardiac support system.

FIG. 12 shows a schematic illustration of a part of a cardiac support system 100 according to a design example. The cardiac support system 100 is the same as or similar to the cardiac support system of FIG. 1. The figure shows a longitudinal section of the part of the cardiac support system 100 in the assembled state of the cardiac support system 100, which comprises the head unit 110 and the line device 105. The cardiac support system 100 also comprises a sleeve 1205. The sleeve 1205 encloses a part of the cardiac support system opposite to the head unit 110, wherein the sleeve 1205 encloses about half of the structural section 220 and the distal attachment section of the line device 105. The sleeve 1205 is shown here only allusively to illustrate an insertion situation of the cardiac support system with a line device 105 in terms of the configuration of the line device 105. Due to the arrangement of the sleeve 1205, the region of the line device 105 not enclosed by the sleeve 1205 has a larger usable installation space than the region enclosed by the sleeve 1205.

Figure 13:
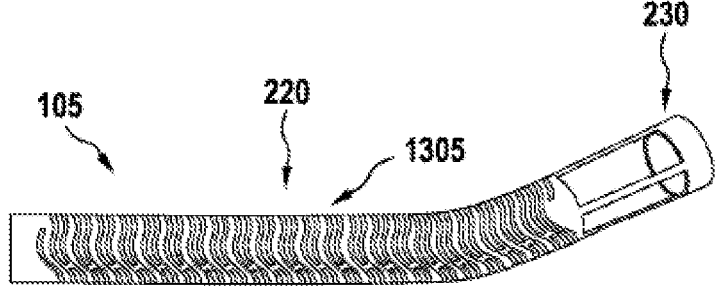
FIG. 13 a perspective illustration of a line device.

FIG. 13 shows a schematic illustration of a line device 105 according to a design example. The line device 105 is the same as or similar to the line device of one of the figures described above. The figure shows a plan view onto the line device 105. According to the design example shown here, the line device comprises a sealing layer 1305. The sealing layer 1305 is disposed on or in the structural section 220 and configured to seal the at least one stiffening recess in a fluid-tight manner. The sealing layer 1305 can be formed by potting or overmolding the structural section 220 with a biocompatible plastic. The sealing layer 1305 seals the structural section 220 in a fluid-tight manner so that the blood flow can be drawn into the inlet section 230 and pumped through the line device 105, along the structural section 220, into the outlet unit and thus into the aorta without loss. The sealing layer 1305 is made of a plastic that is still soft enough after curing to withstand the movements of the line device 105 during operation of the cardiac support system, e.g. polyurethane or silicone. When the cardiac support system, in particular the line device 105, is pushed through the aortic arch during a surgical procedure, cracking of the plastic of the sealing layer 1305 is avoided by the use of an appropriately selected material of the sealing layer 1305. The applied plastic can also be used as a fastener and as mechanical protection for a sensor cable integrated into the line device.

Figure 14:
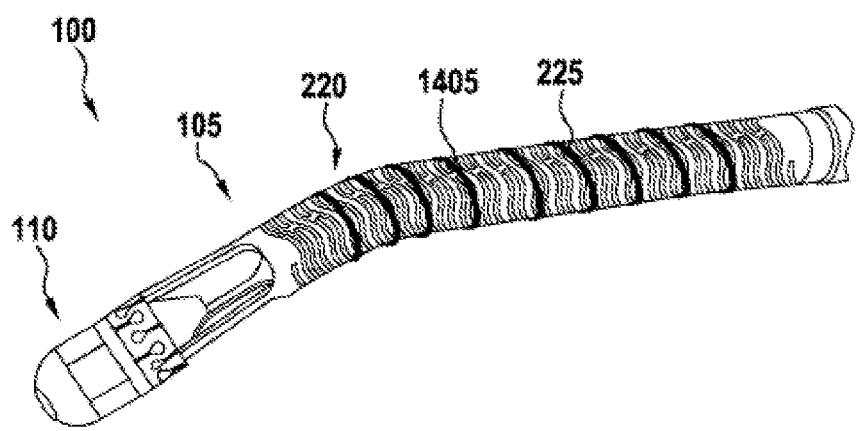
FIG. 14 a perspective illustration of a part of a cardiac support system.

FIG. 14 shows a schematic illustration of a part of a cardiac support system 100 according to a design example. The cardiac support system 100 is the same as or similar to the cardiac support system of one of the figures described above. The figure shows a side view of the section of the cardiac support system 100 with the head unit 110 and the line device 105. As an example, the head unit 110 here is configured as a sensor assembly. From the head unit 110, a sensor cable 1405 is guided along the inner side of the line device 105 on the inside from the proximal attachment section 210 through the inlet section 230 and to the outer side of the line device 105 through the stiffening recess 225 closest to the inlet section 230 resting on the structural section 220. The sensor cable 1405 continues along the longitudinal axis of the line device 105 wound helically around the structural section 220. Leaving a continuous helix makes it possible to secure the sensor cable 1405, which enables an electrical data and power connection from the sensor tip, i.e. the head unit 110, to the pump in a section of the cardiac support system disposed downstream of the outlet unit, in a break proof manner, for example by gluing, overmolding, or potting the sensor cable 1405. The regular movement of the line device 105 during operation of the cardiac support system 100, due to the pulse and movements of the patient, is thus not passed on to the cable.

Figure 15:
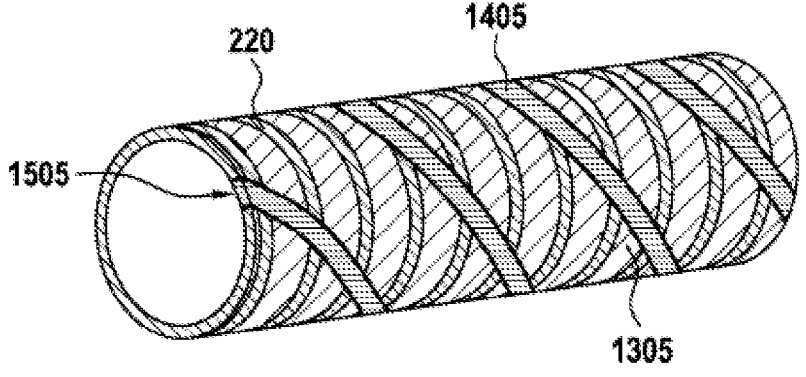
FIG. 15 a perspective illustration of a structural section of a line device.

FIG. 15 shows a schematic illustration of a structural section 220 of a line device according to a design example in a side view. The line device is the same as or similar to the line device of one of the figures described above. The structural section 220 here is made of Nitinol as an example, and comprises a continuous helix 1505 to which the sensor cable 1405 is fastened. The stiffening recesses of the structural section 220 are sealed with the sealing layer 1305. As an example, the sensor cable 1405 is configured as a flexible thin-film substrate and is largely decoupled from mechanical stresses by the continuous helix 1505 to prevent tensile stresses and cable breakage. The helix 1505 is slightly wider than the sensor cable 1405, e.g. by approx. 0.5 to 1 millimeter. When the structural section 220 bends, the spacing of the stiffening recesses on the outside of the bend of the structural section 220 increases, while the stiffening recesses on the inside of the bend are pushed together. The continuous helix 1505 is not or only slightly deformed by the bending of the structural section 220 and thus provides mechanical protection for the sensor cable 1405.

Figure 16:
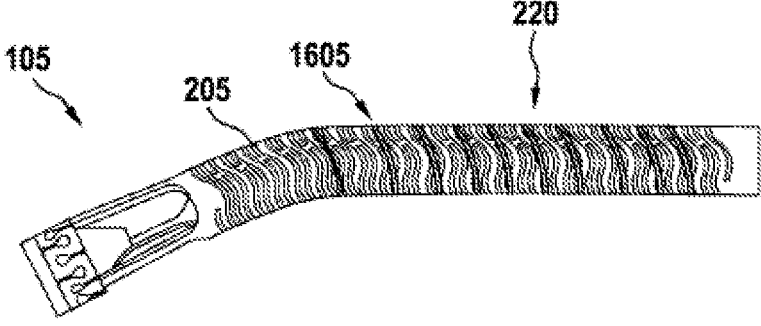
FIG. 16 a perspective illustration of a line device.

FIG. 16 shows a schematic illustration of a line device 105 according to a design example. The line device 105 is the same as or similar to the line device of one of the figures described above. According to the design example shown here, the line device 105 comprises a cable groove 1605, wherein the cable groove 1605 is formed to guide a cable along the main body 205, in particular wherein the cable groove 1605 is configured to extend helically around the structural section 220. The sensor cable, for example, can be accommodated in the cable groove 1605 as described with reference to the previous FIG. 14 and FIG. 15. In this case, the cable groove 1605 is formed to at least partially accommodate the sensor cable in order to provide additional mechanical protection for the sensor cable. The figure therefore shows a laser-cut design example of the line device 105 with an integrated cable groove 1605 to provide additional mechanical protection for an integrated cable.

Figure 17:
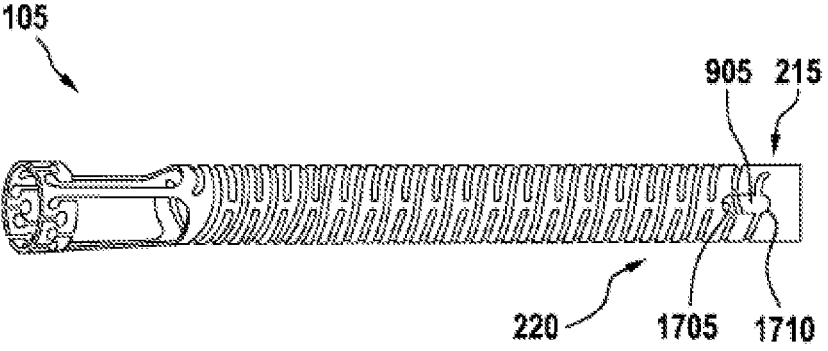
FIG. 17 a perspective illustration of a line device.

FIG. 17 shows a schematic illustration of a line device 105 according to a design example. The line device 105 is the same as or similar to the line device 105 of FIG. 10, with the exception of the lead-out opening 905. In the design example shown here, part of the lead-out opening 905 is disposed in the structural section 220 and the other part is disposed in the distal attachment section 215. Here too, the lead-out opening 905 for leading out the guide wire is cut into the main body of the line device 105 as an elongated recess. The lead-out opening is furthermore chamfered, for example, on both the inner side of the line device 105 and the outer side of the line device 105 and thus has an inner diameter chamfer 1705 and an outer diameter chamfer 1710.

Figure 18:
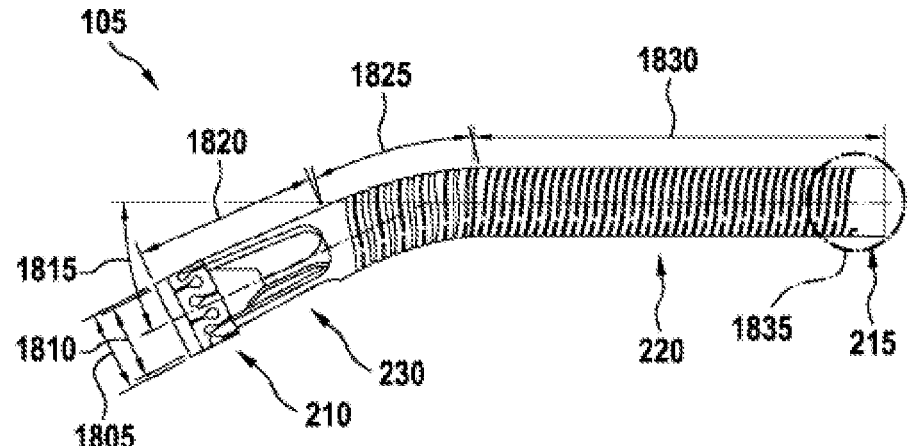
FIG. 18 a schematic illustration of a part of a line device.

FIG. 18 shows a schematic illustration of a line device 105 according to a design example. The shown line device 105 is the same as or similar to the line device 105 described with reference to FIG. 10, whereby the figure also includes labels to show exemplary dimensions of the line device 105. On the proximal attachment section 210, the line device 105 has an inner diameter of 6.5 millimeters indicated by the label 1805. The outer diameter in this region indicated by the label 1810 is 7 millimeters. The angle of the bending point indicated by the label 1815 is 26 degrees. The label 1820 indicates a length of 15 millimeters of a region of the line device 105, which comprises the proximal attachment section 210 and the inlet section 230, and a region of the structural section 220 with the stiffening recess closest to the inlet section 230. An adjoining, bent section of the structural section 220 that extends obliquely to the longitudinal axis of the line device 105 has a length of 14 millimeters, as indicated by the label 1825. The adjacent section of the line device 105 provided with the label 1830 comprises a remaining region of the structural section 220 and the distal attachment section 215, whereas the circular label 1835 indicates the region of the line device 105 with the distal attachment section 215, which is described in the following FIG. 19.

Figure 19:
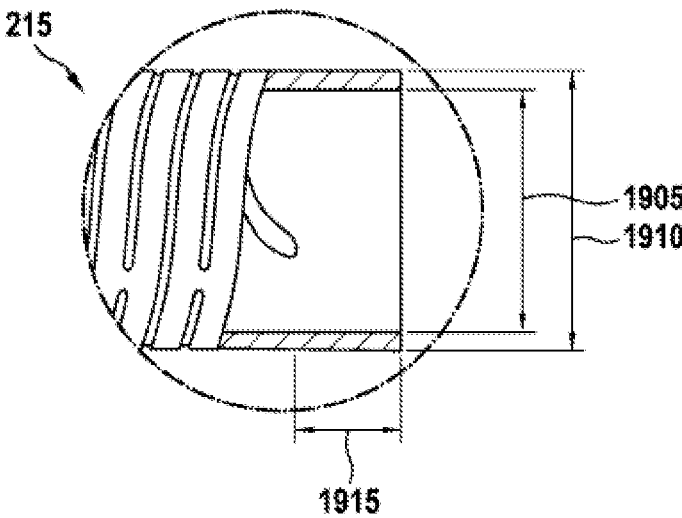
FIG. 19 a cut-out enlargement of the line device of FIG. 18.

FIG. 19 shows a schematic illustration of a part of a line device according to a design example. The figure shows the end section of the line device with the distal attachment section 215 marked in the previous FIG. 18 with labels illustrating exemplary dimensions. On the distal attachment section 215, the line device has an inner diameter of 5.5 millimeters indicated by the label 1905. The outer diameter indicated by the label 1910 in this region is 6 millimeters. The label 1915 indicates a section of the distal attachment section 215 with a length of 2.40 millimeters.

Figure 20:
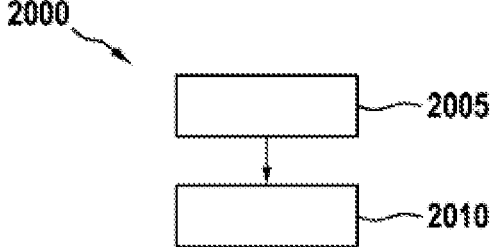
FIG. 20 a flow diagram of a production method.

FIG. 20 shows a flow diagram of a method 2000 for producing a line device for conducting a blood flow for a cardiac support system according to a design example. The method 2000 comprises a forming step 2005 and a heat treating step 2010. In the forming step 2005, a main body is formed from a semi-finished product made of a shape memory material. The main body comprises a proximal or first attachment section at a first end for attaching the line device to a head unit of the cardiac support system and comprises a distal or second attachment section at a second end for attaching the line device to an outlet unit of the cardiac support system. The attachment sections are formed to be connectable in a form-locking and/or force-locking manner. The main body further comprises a structural section having at least one stiffening recess between the attachment sections, wherein the at least one stiffening recess is formed to change the stiffness of the main body. The main body also optionally comprises an inlet section between the structural section and the proximal or first attachment section, wherein the inlet section is formed to allow initiation of the blood flow. In the heat treating step 2010, the main body formed in the forming step 2005 is heat treated to emboss a predetermined shape on the main body.

Figure 21:
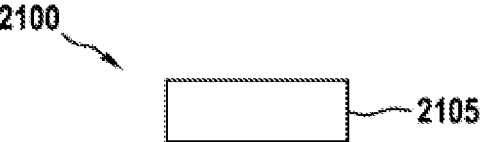
FIG. 21 a flow diagram of an assembly method.

FIG. 21 shows a flow diagram of a method 2100 for assembling a cardiac support system according to a design example. By carrying out the method 2100 for assembling, a cardiac support system that is the same as or similar to the cardiac support system of one of the figures described above can be assembled. The method 2100 comprises a step 2105 of producing a form-locking and/or force-locking connection of the head unit and the outlet unit to the line device to assemble the cardiac support system.

If a design example includes an "and/or" conjunction between a first feature and a second feature, this should be read to mean that the design example according to one embodiment comprises both the first feature and the second feature and, according to another embodiment, comprises either only the first feature or only the second feature.

The invention claimed is:
1. A line device for conducting a blood flow for a cardiac support system, comprising:

a main body, wherein the main body comprises:

a first attachment section at a first end configured to attach the line device to a head unit of the cardiac support system;

a second attachment section at a second end;

a structural section comprising a sidewall, the sidewall comprising:

a flexible section proximal to the first attachment section, the flexible section having a plurality of stiffening recesses between the first attachment section and the second attachment section; and a rigid section proximal to the flexible section, wherein the rigid section is free of stiffening recesses; and a lead-out opening extending from an outer surface of the structural section to a lumen of the line device, such that a guidewire can be advanced into the lumen through the first attachment section and out of the lumen through the lead-out opening, wherein the lead-out opening is an elongate opening configured to receive the guidewire, wherein the lead-out opening is at least partially disposed within the rigid section of the sidewall proximal to the flexible section;

wherein the second attachment section is coupled to an outlet unit, the outlet unit comprising an outlet opening, and wherein each individual stiffening recess of the plurality of stiffening recesses comprises a helical slot extending around the structural section from a first end of the helical slot to a second end of the helical slot, such that the plurality of stiffening recesses are discontinuous.

2. The line device according to claim 1, wherein the first attachment section is configured to attach the line device to the head unit of the cardiac support system in a form-locking and/or force-locking manner.

3. The line device according to claim 1, wherein the second attachment section comprises at least one connection element configured to establish a force-locking connection.

4. The line device according to claim 1, wherein the main body comprises an inlet section between the structural section and the first attachment section, wherein the inlet section is configured to allow initiation of the blood flow.

5. The line device according to claim 4, wherein the main body comprises a bending point disposed between the inlet section and the second attachment section, wherein the line device comprises a first longitudinal axis proximal to the bending point and a second longitudinal axis at an angle to the first longitudinal axis distal to the bending point.

6. The line device according to claim 4, wherein the inlet section comprises at least one inlet opening through the main body.

7. The line device according to claim 1, wherein at least one portion of the main body is made of a shape memory material.

8. The line device according to claim 7, wherein the shape memory material is nitinol.

9. The line device according to claim 1, further comprising a cable groove configured to guide a cable along the main body.

10. The line device according to claim 1, wherein the structural section extends over at least half of the main body.

11. The line device according to claim 1, wherein the plurality of stiffening recesses comprises a plurality of slotted holes.

12. The line device according to claim 1, further comprising a sealing layer, wherein the sealing layer is disposed on or in the structural section, wherein the sealing layer is configured to seal at least one stiffening recess in a fluid-tight manner.

13. The line device according to claim 1, wherein an inner diameter of the main body changes between the first attachment section and the second attachment section.

14. The line device according to claim 1, wherein the main body comprises a side opening configured to receive a guide wire.

15. The line device according to claim 1, wherein the second attachment section comprises a plurality of recesses.

16. A cardiac support system, comprising:

a head unit;

an outlet unit; and a line device disposed between the head unit and the outlet unit, the line device comprising a main body, wherein the main body comprises:

a first attachment section at a first end configured to attach the line device to the head unit;

a second attachment section at a second end;

a structural section comprising a sidewall, the sidewall comprising:

a flexible section proximal to the first attachment section, the flexible section having a plurality of stiffening recesses between the first attachment section and the second attachment section; and a rigid section proximal to the flexible section, wherein the rigid section is free of stiffening recesses; and a lead-out opening extending from an outer surface of the structural section to a lumen of the line device, such that a guidewire can be advanced into the lumen through the first attachment section and out of the lumen through the lead-out opening, wherein the lead-out opening is an elongate opening configured to receive the guidewire, wherein the lead-out opening is at least partially disposed within the rigid section of the sidewall proximal to the flexible section;

wherein the second attachment section is coupled to the outlet unit, the outlet unit comprising an outlet opening, and wherein each individual stiffening recess of the plurality of stiffening recesses comprises a helical slot extending around the structural section from a first end of the helical slot to a second end of the helical slot, such that the plurality of stiffening recesses are discontinuous.

17. The cardiac support system of claim 16, wherein the first attachment section is configured to attach the line device to the head unit of the cardiac support system in a form-locking and/or force-locking manner.

18. The cardiac support system of claim 16, further comprising a cable configured to extend helically around the structural section.

19. The cardiac support system of claim 18, wherein the main body further comprises a cable groove configured to guide the cable along the main body, wherein the cable groove extends helically around the main body.

20. The cardiac support system of claim 16, wherein the head unit comprises a sensor assembly.

21. The cardiac support system of claim 20, further comprising a cable coupled to the sensor assembly and extending along an outer wall of the line device.

22. A method for producing a line device for conducting a blood flow for a cardiac support system, the method comprising:

forming a main body from a semi-finished product made of a shape memory material, wherein the main body comprises:

a first attachment section at a first end configured to attach the line device to a head unit of the cardiac support system;

a second attachment section at a second end;

a structural section comprising a sidewall, the sidewall comprising:

a flexible section proximal to the first attachment section, the flexible section having a plurality of stiffening recesses between the first attachment section and the second attachment section; and a rigid section proximal to the flexible section, wherein the rigid section is free of stiffening recesses; and a lead-out opening extending from an outer surface of the structural section to a lumen of the line device, such that a guidewire can be advanced into the lumen through the first attachment section and out of the lumen through the lead-out opening, wherein the lead-out opening is an elongate opening configured to receive the guidewire, wherein the lead-out opening is at least partially disposed within the rigid section of the sidewall proximal to the flexible section;

wherein the second attachment section is coupled to an outlet unit, the outlet unit comprising an outlet opening, and wherein each individual stiffening recess of the plurality of stiffening recesses comprises a helical slot extending around the structural section from a first end of the helical slot to a second end of the helical slot, such that the plurality of stiffening recesses are discontinuous; and

heat treating the formed main body so as to emboss a predetermined shape on the main body.

23. The method according to claim 22, wherein the first attachment section is configured to attach the line device to a first unit of the cardiac support system in a form-locking and/or force-locking manner.

24. The method according to claim 22, further comprising producing a form-locking and/or force-locking connection of the outlet unit to the line device to assemble the cardiac support system.

25. The line device of claim 1, wherein the structural section comprises a lateral inlet opening between the first attachment section and the second attachment section, the lateral inlet opening in fluid communication with an interior of the structural section, and the lateral inlet opening integral with the structural section.

26. The line device of claim 1, wherein the structural section is curved at a bending point, and wherein the bending point is between a proximal straight portion and a distal straight portion of the structural section.

27. The line device of claim 1, wherein the first ends of at least some of the helical slots are aligned along an axis parallel to a longitudinal axis of the structural section.

28. The line device of claim 27, wherein at least some of the helical slots are aligned along a second axis parallel to a longitudinal axis of the structural section.

29. The line device of claim 1, wherein at least some of the helical slots are arranged in a repeating pattern.

30. The line device of claim 1, wherein the second attachment section is joined to the outlet unit in a form-locking or force-locking manner.

* * * * *